US010323232B2

(12) United States Patent
Singh et al.

(10) Patent No.: US 10,323,232 B2
(45) Date of Patent: Jun. 18, 2019

(54) METABOLICALLY ENGINEERED METHANOTROPHIC, PHOTOTROPHIC MICROORGANISMS

(71) Applicant: Mogene LC, St. Louis, MO (US)

(72) Inventors: Abhay Singh, Chesterfield, MO (US); Himadri Pakrasi, St. Louis, MO (US); Ganesh M. Kishore, Creve Coeur, MO (US)

(73) Assignee: MOgene LC, St. Louis, MO (US)

( * ) Notice: Subject to any disclaimer, the term of this patent is extended or adjusted under 35 U.S.C. 154(b) by 189 days.

(21) Appl. No.: 14/513,656

(22) Filed: Oct. 14, 2014

(65) Prior Publication Data
US 2015/0104854 A1 Apr. 16, 2015

Related U.S. Application Data

(60) Provisional application No. 61/891,032, filed on Oct. 15, 2013.

(51) Int. Cl.
C12N 1/20 (2006.01)
C12N 9/02 (2006.01)
C12N 9/04 (2006.01)
C12N 9/88 (2006.01)
C12N 9/90 (2006.01)
C12P 7/04 (2006.01)
C12P 7/16 (2006.01)
C12N 15/52 (2006.01)

(52) U.S. Cl.
CPC ............ C12N 9/0073 (2013.01); C12N 1/20 (2013.01); C12N 9/0006 (2013.01); C12N 9/0071 (2013.01); C12N 9/88 (2013.01); C12N 9/90 (2013.01); C12N 15/52 (2013.01); C12P 7/04 (2013.01); C12P 7/16 (2013.01); C12Y 101/01244 (2013.01); C12Y 401/02043 (2013.01); C12Y 503/01027 (2013.01); C12Y 114/13025 (2013.01); C12Y 114/18003 (2013.01); Y02E 50/10 (2013.01)

(58) Field of Classification Search
None
See application file for complete search history.

(56) References Cited

PUBLICATIONS

Komarek et al, Presila 86:295-335, 2014.*
Arfman et al., "Properties of an NAD(H)-containing methanol dehydrogenase and its activator protein from Bacillus methanolicus," Eur J Biochem. 244:426-33, Mar. 1, 1997.
Baani and Liesack, "Two isozymes of particulate methane monooxygenase with different methane oxidation kinetics are found in Methylocystis sp. strain SC2," Proc Natl Acad Sci USA. 105:10203-10208, Jul. 22, 2008.
Baerends et al, "Engineering and analysis of a Saccharomyces cerevisiae strain that uses formaldehyde as an auxiliary substrate," Appl Environ Microbiol. 74:3182-3188, May 2008.
Baik et al., "Mechanistic studies on the hydroxylation of methane by methane monooxygenase," Chem Rev. 103:2385-2419, Jun. 2003.
Balasubramanian et al., "Oxidation of methane by a biological dicopper centre," Nature 465:115-119, May 6, 2010.
Bateman et al., "Pfam 3.1: 1313 multiple alignments and profile HMMs match the majority of proteins," Nucl. Acids Res., 27:260-262, Jan. 1999.
Benita et al. "Humphery-Smith, Ian; Oosting, Ronald S. Analysis of high throughput protein expression in Escherichia coli," Mol. Cell. Prot. 5:1567-1580, Sep. 2006.
Brazeau and Lipscomb, "Electron transfer and radical forming reactions of methane monooxygenase," Subcell Biochem. 35:233-277, 2008.
Callaghan, "Enzymes involved in the anaerobic oxidation of n-alkanes: from methane to long-chain paraffins." Front Microbiol. 4:89, May 14, 2013.
Chan et al., "Efficient oxidation of methane to methanol by dioxygen mediated by tricopper clusters," Angew Chem Int Ed Engl. 52:3731-3735, Mar. 25, 2013.
Chistoserdova and Lidstrom, "Aerobic methylotrophic prokaryotes," The Prokaryotes, Springer, 2013.
Chistoserdova et al., "Novel dephosphotetrahydromethanopterin biosynthesis genes discovered via mutagenesis in Methylobacterium extorquens AM1," J Bacteriol 187:2508-2512, Apr. 2005.
Chistoserdova et al., "The expanding world of methylotrophic metabolism," Annu Rev Microbiol. 63:477-499, Oct. 2009.
Choi et al., "The membrane-associated methane monooxygenase (pMMO) and pMMONADH: quinone oxidoreductase complex from Methylococcus capsulatus Bath," J Bacteriol. 185:5755-5764, Oct. 2003.
Davis et al., "Techno-economic analysis of autotrophic microalgae for fuel production," Applied Energy 88: 3524-3531, May 2011.
de Graaf et al., "Cellular pathways for DNA repair and damage tolerance of formaldehyde-induced DNA-protein crosslinks," DNA Repair 8:1207-1214, Oct. 2009.
Didier et al., "Using an Escherichia coli cell—free extract to screen for soluble expression of recombinant proteins," J. Struc. Func. Genom. 5:69-74, Mar. 2004.
Dijkhuizen et al., "Methanol, a potential feedstock for biotechnological processes," Trends in Biotechnology 10: 262-267, Oct. 1985.
Ducat et al., "Engineering cyanobacteria to generate high-value products," Trends Biotechnol. 29: 95-103, Feb. 2011.
Duester et al., "Molecular analysis of the human class I alcohol dehydrogenase gene family and nucleotide sequence of the gene encoding the beta subunit," J Biol Chem. 261:2027-33, Feb. 1986.
Endo and Sawasaki, "Advances in genome—wide protein expression using the wheat germ cell-free system," Meth. Mol. Biol. 310:145-167, 2005.

(Continued)

Primary Examiner — Patricia Duffy
(74) Attorney, Agent, or Firm — Fish & Richardson P.C.

(57) ABSTRACT

This disclosure relates to the engineering of phototrophic microorganisms for conversion of alkanes into higher-value products. Recombinant phototrophic organisms such as cyanobacteria can be engineered, optionally in a modular format, to express enzymes involved in converting methane to methanol, methanol to formaldehyde, formaldehyde to central metabolic pathway intermediates, and such intermediates to n-butanol.

8 Claims, 2 Drawing Sheets
Specification includes a Sequence Listing.

(56) References Cited

PUBLICATIONS

Endo and Sawasaki, "Cell-free expression systems for eukaryotic protein production," Cur. Opin. Biotech. 17:373-380, 2006.
GenBank Accession No. AAA22593.1, GI: 143175, methanol dehydrogenase alpha-10 subunit [Bacillus sp.], dated Jun. 23, 2010, 1 page.
GenBank Accession No. AAA87220.2, GI: 7188931, PmoA [Methylosinus trichosporium OB3b], dated Mar. 10, 2010, 1 page.
GenBank Accession No. AAB21393.1, GI: 245216, Protein C [Methylosinus trichosporium], dated Jun. 23, 2010, 1 page.
GenBank Accession No. AAB62391.2, GI: 7770065, methane monooxygenase component C [Methylococcus capsulatus], dated Mar. 10, 2010, 1 page.
GenBank Accession No. AAC45290.1, GI: 2098696, soluble methane monooxygenase protein A beta subunit [Methylocystis sp. M], dated Jun. 23, 2010, 1 page.
GenBank Accession No. AAF01268.1, GI: 6013166, MmoX, partial [Methylocystis sp. WI14], dated Mar. 10, 2010, 1 page.
GenBank Accession No. AAF01269.1, GI: 6013167, MmoY [Methylocystis sp. WI14], dated Mar. 10, 2010, 1 page.
GenBank Accession No. AAF01270.1, GI: 6013168, MmoB [Methylocystis sp. WI14], dated Mar. 10, 2010, 1 page.
GenBank Accession No. AAF01271.1, GI: 6013169, MmoZ [Methylocystis sp. WI14], dated Mar. 10, 2010, 1 page.
GenBank Accession No. AAF01273.1, GI: 6013171, MmoC, partial [Methylocystis sp. WI14], dated Mar. 10, 2010, 1 page.
GenBank Accession No. AAF04157.2, GI: 7770067, soluble methane monooxygenase hydroxylase component gamma subunit [Methylococcus capsulatus], dated Mar. 10, 2010, 1 page.
GenBank Accession No. AAF04158.2, GI: 7770068, soluble methane monooxygenase regulatory protein B [Methylococcus capsulatus], dated Mar. 10, 2010, 1 page.
GenBank Accession No. AAF37893.1, GI:7188932, PmoC [Methylosinus trichosporium OB3b], dated Mar. 10, 2010, 1 page.
GenBank Accession No. AAF37894.1, GI: 7188933, PmoB [Methylosinus trichosporium OB3b], dated Mar. 10, 2010, 1 page.
GenBank Accession No. AAF37897.1, GI: 7188938, PmoB [Methylocystis sp. M], dated Mar. 10, 2010, 1 page.
GenBank Accession No. AAH74738.1, GI: 50960621, Class I alcohol dehydrogenase, alpha subunit [Homo sapiens], dated Mar. 6, 2012, 2 pages.
GenBank Accession No. AAL80344.1, GI:18892157, hexulose-6-phosphate synthase (d-arabino 3-hexulose 6-phosphate formaldehyde lyase) [Pyrococcus furiosus DSM 3638], dated Jul. 17, 2012, 1 page.
GenBank Accession No. AAM30911.1, GI: 20905670, hexulose-6-phosphate synthase [Methanosarcina mazei Go1], dated Jul. 18, 2012, 1 page.
GenBank Accession No. AAM98772.1, GI: 22654852, methanol dehydrogenase activator protein [Bacillus methanolicus], dated Mar. 11, 2010, 1 page.
GenBank Accession No. AAR39392.1, GI: 40074227, 3-hexulose-6-phosphate synthase [Bacillus methanolicus MGA3], dated Jun. 23, 2010, 1 page.
GenBank Accession No. AAU90888.1, GI: 53756597, SIS domain protein [Methylococcus capsulatus str. Bath]; dated Jul. 17, 2012, 1 page.
GenBank Accession No. AAU90889.1, GI: 53756598, hexulose-6-phosphate synthase [Methylococcus capsulatus str. Bath]; dated Jul. 17, 2012, 1 page.
GenBank Accession No. AAU92723.1, GI: 53758432, methane monooxygenase, D subunit [Methylococcus capsulatus str. Bath]; dated Jul. 17, 2012, 2 pages.
GenBank Accession No. AAU92736.1, GI: 53758445, methane monooxygenase, A subunit, alpha chain [Methylococcus capsulatus str. Bath], dated Jul. 17, 2012, 2 pages.
GenBank Accession No. AAZ81968.1, GI: 73745618, protein A alpha subunit of soluble methane monooxygenase [Methylosinus trichosporium], dated Jun. 2, 2011, 1 page.
GenBank Accession No. AAZ81969.1, GI: 73745619, protein a beta subunit of soluble methane monooxygenase [Methylosinus trichosporium], dated Jun. 2, 2011, 1 page.
GenBank Accession No. AAZ81970.1, GI: 73745620, protein B of soluble methane monooxygenase [Methylosinus trichosporium], dated Jun. 2, 2011, 1 page.
GenBank Accession No. AAZ81971.1, GI: 73745621, protein A gamma subunit of soluble methane monooxygenase [Methylosinus trichosporium], dated Jun. 2, 2011, 1 page.
GenBank Accession No. AAZ81973.1, GI: 73745623, protein C of soluble methane monooxygenase [Methylosinus trichosporium], dated Jun. 2, 2011, 1 page.
GenBank Accession No. ABD46893.1, GI: 88656492, MmoY [Methylosinus sporium], dated Oct. 2, 2006, 1 page.
GenBank Accession No. ABD46894.1, GI: 88656493, MmoB [Methylosinus sporium], dated Oct. 2, 2006, 1 page.
GenBank Accession No. ABD46895.1, GI: 88656494, MmoZ [Methylosinus sporium], dated Oct. 2, 2006, 1 page.
GenBank Accession No. ABD46896.1, GI: 88656495, MmoD [Methylosinus sporium], dated Oct. 2, 2006, 1 page.
GenBank Accession No. ABD46897.1, GI: 88656496, MmoC [Methylosinus sporium], dated Oct. 2, 2006, 1 page.
GenBank Accession No. ABN07165.1, GI: 124363357, hexulose-6-phosphate synthase [Methanocorpusculum labreanum Z], dated Jul. 14, 2012, 1 page.
GenBank Accession No. ABN07618.1, GI: 124363810, hexulose-6-phosphate synthase [Methanocorpusculum labreanum Z], dated Jul. 14, 2012, 2 pages.
GenBank Accession No. AFL66208.1, GI: 390191152, 6-phospho 3-hexuloisomerase [Desulfurococcus fermentans DSM 16532], dated Sep. 28, 2012, 2 pages.
GenBank Accession No. BAA84759.1, GI: 6002406, soluble methane monooxygenase regulatory protein B (MMOB) [Methylomonas sp. Kswiii], dated Aug. 9, 2006, 1 page.
GenBank Accession No. BAE86875.1, GI: 89572582, soluble methane monooxygenase hydroxylase component alpha subunit [Methylomicrobium japanense], dated Apr. 8, 2008, 2 pages.
GenBank Accession No. BAE86877.1, GI: 89572584, soluble methane monooxygenase regulatory proteinB [Methylomicrobium japanense], dated Apr. 8, 2008, 1 page.
GenBank Accession No. BAF62077.2, GI: 224967033, particulate methane monooxygenase protein a [Methylomarinum vadi], dated Aug. 16, 2012, 1 page.
GenBank Accession No. BAH22845.1, GI: 223717937, methane monooxygenase protein A [Methylococcaceae bacterium SF-BR], dated May 15, 2013, 1 page.
GenBank Accession No. BAJ17646.1, GI: 306921972, soluble methane monooxygenase hydroxylase component beta-subunit [Methylovulum miyakonense HT12], dated Aug. 27, 2012, 1 page.
GenBank Accession No. BAJ17647.1, GI: 306921973, soluble methane monooxygenase regulatory protein B [Methylovulum miyakonense HT12], dated Aug. 27, 2012, 1 page.
GenBank Accession No. BAJ17648.1, GI: 306921974, soluble methane monooxygenase hydroxylase component gamma-subunit [Methylovulum miyakonense HT12], dated Aug. 27, 2012, 1 page.
GenBank Accession No. BAM71040.1, GI: 427190913, particulate methane monooxygenase protein A [Methylohalobius crimeensis 10Ki], dated Dec. 3, 2012, 1 page.
GenBank Accession No. CAA39068.2, GI: 5102756, Protein A-alpha subunit of soluble methane monooxygenase (sMMO) [Methylosinus trichosporium OB3b], dated Feb. 4, 2011, 2 pages.
GenBank Accession No. CAJ01562.1, GI: 83308654, pmoB [uncultured bacterium], dated Jan. 31, 2011, 2 pages.
GenBank Accession No. CAJ01616.1, GI: 83308706, methane monooxygenase subunit C, pmoC [Methylocapsa acidiphila], dated Feb. 4, 2011, 2 pages.
GenBank Accession No. CAJ01618.1, GI: 83308708, methane monooxygenase subunit B, pmoB [Methylocapsa acidiphila], dated Feb. 4, 2011, 2 pages.
GenBank Accession No. CAJ26291.1, GI: 74381909, protein A-alpha subunit of soluble methane monooxygenase [Methylocella silvestris BL2], dated Feb. 4, 2011, 1 page.

(56) References Cited

PUBLICATIONS

GenBank Accession No. CAJ26295.1, GI: 74381913, methane monooxygenase component D [Methylocella silvestris BL2], dated Feb. 4, 2011, 1 page.
GenBank Accession No. CAQ01554.1, GI: 169156406, hexulose-6-phosphate synthase [*Clavibacter michiganensis* subsp. sepedonicus], dated Aug. 28, 2012, 1 page.
GenBank Accession No. CCE23598.1, GI: 351717933, Hexulose-6-phosphate synthase and isomerase [*Methylomicrobium alcaliphilum* 20Z], dated Jan. 9, 2012, 1 page.
GenBank Accession No. EAR68750.1, GI: 89089643, hexulose-6-phosphate synthase [*Bacillus* sp. NRRL B-14911], dated Mar. 1, 2006, 1 page.
GenBank Accession No. EHQ34470.1, GI: 373906366, 3-hexulose-6-phosphate isomerase [Methanoplanus limicola DSM 2279], dated Aug. 4, 2012, 1 page.
GenBank Accession No. EIJ77618.1, GI: 387585284, methanol dehydrogenase [Bacillus methanolicus PB1], dated May 14, 2012, 1 page.
GenBank Accession No. EKQ54947.1, GI: 410600419, 6-phospho 3-hexuloisomerase [*Methanobacterium* sp. Maddingley MBC34], dated Nov. 2, 2012, 2 pages.
GenBank Accession No. ERK43186.1, GI: 544229974, 6-phospho 3-hexuloisomerase [Lactobacillus brevis ATCC 14869 = DSM 20054], dated Sep. 18, 2013, 2 pages.
GenBank Accession No. MCA3043, GI: 53756598, hexulose-6-phosphate synthase [*Methylococcus capsulatus* str. Bath], dated Jul. 17, 2012, 2 pages.
GenBank Accession No. MCA3044, GI: 53756597, SIS domain protein [*Methylococcus capsulatus* str. Bath], dated Jul. 17, 2012, 2 pages.
GenBank Accession No. MGA3_15301, GI:387587407, 6-phospho-3-hexuloisomerase [Bacillus methanolicus MGA3], dated May 14, 2012, 2 pages.
GenBank Accession No. MGA3_15306, GI:387587408, 3-hexulose-6-phosphate synthase [Bacillus methanolicus MGA3], dated, May 14, 2012, 2 pages.
GenBank Accession No. MGA3_17392, GI:387585261, NAD-dependent methanol dehydrogenase [Bacillus methanolicus MGA3], dated May 14, 2012, 2 pages.
GenBank Accession No. NP_000658.1, GI: 4501929, alcohol dehydrogenase IA [*Homo sapiens*], dated Jan. 12, 2013, 3 pages.
GenBank Accession No. NP_000659.2, GI: 34577061, alcohol dehydrogenase 1B isoform 1 [*Homo sapiens*], dated Sep. 16, 2012, 3 pages.
GenBank Accession No. NP_000660.1, GI: 4501933, alcohol dehydrogenase 1C [*Homo sapiens*], dated Sep. 23, 2012, 3 pages.
GenBank Accession No. NP_143767.1, GI: 14591680, D-arabino 3-hexulose 6-phosphate formaldehyde lyase [Pyrococcus horikoshii OT3], dated Sep. 12, 2012, 2 pages.
GenBank Accession No. NP_371094.1, GI: 15923560, hexulose-6-phosphate synthase [*Staphylococcus aureus* subsp. aureus Mu50], dated Sep. 27, 2012, 2 pages.
GenBank Accession No. NP_577949.1, GI: 18976592, hexulose-6-phosphate synthase [Pyrococcus furiosus DSM 3638], dated Sep. 12, 2012, 2 pages.
GenBank Accession No. NP_957659.1, GI: 41057056, NAD(P)-dependent methanol dehydrogenase [Bacillus methanolicus MGA3], dated Sep. 13, 2012, 1 page.
GenBank Accession No. P11987.4, GI: 19855848, RecName: Full= Methane monooxygenase component A gamma chain; AltName: Full=Methane hydroxylase [*Methylococcus capsulatus* str. Bath], dated Oct. 5, 2012, 4 pages.
GenBank Accession No. P22867.1, GI: 141050, RecName: Full= Methane monooxygenase component D [*Methylococcus capsulatus* str. Bath], dated Oct. 5, 2012, 2 pages.

GenBank Accession No. P22868.2, GI: 18266834, RecName: Full= Methane monooxygenase component C; AltName: Full=Methane hydroxylase; AltName: Full=Methane monooxygenase reductase; Short=MMOR [*Methylococcus capsulatus* str. Bath], dated Oct. 5, 2012, 5 pages.
GenBank Accession No. P31005.3, GI: 462590, RecName: Full= NAD-dependent methanol dehydrogenase; Short=MDH; Short= MEDH; AltName: Full=Type 3 alcohol dehydrogenase [Bacillus methanolicus], dated Sep. 7, 2012, 2 pages.
GenBank Accession No. Q53562.1, GI: 21362648, RecName: Full= Methane monooxygenase component D [Methylosinus trichosporium], dated Nov. 2, 2012, 1 page.
GenBank Accession No. Q53563.1, GI: 21362649, RecName: Full= Methane monooxygenase component C; AltName: Full=Methane hydroxylase; AltName: Full=Methane monooxygenase reductase; Short=MMOR [Methylosinus trichosporium], dated Oct. 5, 2012, 2 pages.
GenBank Accession No. YP_001710170.1, GI: 170781838, hexulose-6-phosphate synthase [*Clavibacter michiganensis* subsp. sepedonicus], dated Sep. 12, 2012, 1 page.
GenBank Accession No. YP_001940241.1, GI: 189219600, Particulate methane monooxygenase alpha (PmoB) subunit [Methylacidiphilum infernorum V4], dated Sep. 12, 2012, 2 pages.
GenBank Accession No. YP_001940243.1, GI: 189219602, Particulate methane monooxygenase gamma (PmoC) subunit [Methylacidiphilum infernorum V4], dated Sep. 12, 2012, 2 pages.
GenBank Accession No. YP_004341647.1, GI: 327400808, 6-phospho 3-hexuloisomerase [Archaeoglobus veneficus SNP6], dated Sep. 13, 2012, 2 pages.
GenBank Accession No. YP_004514931.1, GI: 333985721, 6-phospho 3-hexuloisomerase [Methylomonas methanica MC09], dated Sep. 13, 2012, 2 pages.
GenBank Accession No. YP_004915811.1, GI: 357403887, methane monooxygenase subunit C [*Methylomicrobium alcaliphilum* 20Z], dated Sep. 27, 2012, 1 page.
GenBank Accession No. YP_004915812.1, GI: 357403888, methane monooxygenase subunit A [*Methylomicrobium alcaliphilum* 20Z], dated Sep. 13, 2012, 1 page.
GenBank Accession No. YP_006593635.1, GI: 402774098, particulate methane monooxigenase subunit C [*Methylocystis* sp. SC2], dated Aug. 31, 2012, 1 page.
GenBank Accession No. YP_006593636.1, GI: 402774099, Particulate methane monooxygenase subunit A [*Methylocystis* sp. SC2], dated Aug. 31, 2012, 1 page.
GenBank Accession No. YP_040023.1, GI: 49482799, hexulose-6-phosphate synthase [*Staphylococcus aureus* subsp. aureus MRSA252], dated Sep. 13, 2012, 2 pages.
GenBank Accession No. YP_113660.1, GI: 53804675, methane monooxygenase subunit A, beta chain [*Methylococcus capsulatus* str. Bath], dated Aug. 31, 2012, 2 pages.
GenBank Accession No. YP_113661.1, GI: 5380467, methane monooxygenase subunit B [*Methylococcus capsulatus* str. Bath], dated Aug. 31, 2012, 2 pages.
GenBank Accession No. YP_113663.1, GI: 53804672, methane monooxygenase subunit A, gamma chain [*Methylococcus capsulatus* str. Bath], dated Aug. 31, 2012, 2 pages.
GenBank Accession No. YP_113664.1, GI: 53804671, methane monooxygenase, D subunit [*Methylococcus capsulatus* str. Bath], dated Aug. 31, 2012, 2 pages.
GenBank Accession No. YP_113665.1, GI: 53804670, methane monooxygenase subunit C [*Methylococcus capsulatus* str. Bath], dated Aug. 31, 2012, 2 pages.
GenBank Accession No. YP_114234.1, GI: 53804139, methane monooxygenase subunit B [*Methylococcus capsulatus* str. Bath], dated Aug. 31, 2012, 2 pages.
GenBank Accession No. YP_114235.1, GI: 53804130, methane monooxygenase subunit A [*Methylococcus capsulatus* str. Bath], dated Aug. 31, 2012, 2 pages.
GenBank Accession No. YP_115430.1, GI: 53802837, hexulose-6-phosphate synthase [*Methylococcus capsulatus* str. Bath], dated Aug. 31, 2012, 2 pages.

(56) References Cited

PUBLICATIONS

GenBank Accession No. YP_152642.1, GI: 56415567, hexulose-6-phosphate synthase [*Salmonella enterica* subsp. enterica serovar Paratyphi A str. ATCC 9150], dated Sep. 12, 2012, 2 pages.

GenBank Accession No. YP_153252.1, GI: 56416177, hexulose-6-phosphate synthase [*Salmonella enterica* subsp. enterica serovar Paratyphi A str. ATCC 9150], dated Sep. 13, 2012, 2 pages.

Goswami et al., "An overview on alcohol oxidases and their potential applications," Appl Microbiol Biotechnol. 97:4259-75, May 2013.

Gou et al., "Functional expression of the particulate methane mono-oxygenase gene in recombinant *Rhodococcus erythropolis*," FEMS Microbiol Lett. 263:136-141, Oct. 2006.

Hakemian and Rosenzweig, "The biochemistry of methane oxidation," Ann. Rev. Biochem. 76:223-241, Jul. 2007.

Hallam et al., "Identification of methyl coenzyme M reductase A (mcrA) genes associated with methane-oxidizing archaea," Appl Environ Microbiol. 69: 5483-5491, Sep. 2003.

Han et al., "Heterologous expression of particulate methane monooxygenase in different host cells," Sheng Wu Gong Cheng Xue Bao. 25:1151-9, Aug. 2009 (with English Abstract).

Hanson and Hanson, "Methanotrophic bacteria," Microbiol Rev. 60:439-471, Jun. 1996.

Jahng and Wood, "Trichloroethylene and chloroform degradation by a recombinant pseudomonad expressing soluble methane monooxygenase from Methylosinus trichosporium OB3b," Appl Environ Microbiol. 60:2473-2482, Jul. 1994.

Jiang et al., "Methanotrophs: Multifunctional bacteria with promising applications in environmental bioengineering," Biochem. Eng. J. 49:277-288, May 15, 2010.

Jorquera et al., "Comparative energy life-cycle analyses of microalgal biomass production in open ponds and photobioreactors," Bioresour Technol. 101:1406-1413, Feb. 2010.

Kelly et al., "Insights into the obligate methanotroph *Methylococcus capsulatus*," Trends Microbiol. 13:195-198, May 2005.

Keren et al., "Psb29, a conserved 22-kD protein, functions in the biogenesis of Photosystem II complexes in *Synechocystis* and *Arabidopsis*," Plant Cell 17:2768-2781, Oct. 2005.

Kigawa et al., "Preparation of *Escherichia coli* cell extract for highly productive cell—free protein expression," J. struc. Func. Genom. 5:63-68, Mar. 2004.

Knapp et al., "Methane monooxygenase gene expression mediated by methanobactin in the presence of mineral copper sources," Proc Natl Acad Sci USA. 104:12040-12045, Jul. 17, 2007.

Krebs et al., "Cyanobacterial alkane biosynthesis further expands the catalytic repertoire of the ferritin-like 'di-iron-carboxylate' proteins," Curr Opin Chem Biol. 15:291-303, Apr. 2011.

Lan and Liao, "ATP drives direct photosynthetic production of 1-butanol in cyanobacteria," Proc Natl Acad Sci USA. 109:6018-23, Apr. 17, 2012.

Lan and Liao, "Microbial synthesis of n-butanol, isobutanol, and other higher alcohols from diverse resources," ioresour Technol. 135:339-49, May 2013.

Lefebvre et al., "Increased sedoheptulose-1,7-bisphosphatase activity in transgenic tobacco plants stimulates photosynthesis and growth from an early stage in development," Plant Physiol. 138:451-60, May 2005.

Lieberman and Rosenzweig, "Crystal structure of a membrane-bound metalloenzyme that catalyses the biological oxidation of methane," Nature 434:177-82, Mar. 10, 2005.

Lloyd et al., "Heterologous expression of soluble methane monooxygenase genes in methanotrophs containing only particulate methane monooxygenase," Arch Microbiol. 171: 364-370, May-Jun. 1999.

Luo et al., "Life cycle energy and greenhouse gas emissions for an ethanol production process based on blue-green algae," Environ Sci Technol. 44:8670-8677, Nov. 15, 2010.

Machado and Atsumi, "Cyanobacterial biofuel production," J Biotechnol. 162:50-56, Nov. 30, 2012.

Marx et al., "Formaldehyde-detoxifying role of the tetrahydromethanopterin linked pathway in Methylobacterium extorquens AM1," J Bacteriol 185:7160-7168, Dec. 2003.

Merkx and Lippard, "Why OrfY? Characterization of MMOD, a long overlooked component of the soluble methane monooxygenase from *Methylococcus capsulatus* (Bath)," J Biol Chem. 277:585-865, Feb. 22, 2002.

Orita et al., "The archaeon Pyrococcus horikoshii possesses a bifunctional enzyme for formaldehyde fixation via the ribulose monophosphate pathway," J Bacteriol. 187:3636-3642, Jun. 2005.

Prior and Dalton, "The Effect of Copper Ions on Membrane Content and Methane Monooxygenase Activity in Methanol-grown Cells of *Methylococcus capsulatus* (Bath)," J. Gen. Microbiol. 131: 155-163, Jan. 1985.

Robinson and Winge, "Copper metallochaperones," Annu Rev Biochem. 79:537-562, 2010.

Rosenzweig, "Metalloenzymes: Put a ring on it," Nat Chem Biol. 9:220-221, Apr. 2013.

Rutherford et al., "Functional genomic study of exogenous n-butanol stress in *Escherichia coli*," Appl Environ Microbiol. 76:1935-1945, Mar. 2010.

Saha et al., Reconstruction and comparison of the metabolic potential of cyanobacteria *Cyanothece* sp. ATCC 51142 and *Synechocystis* sp. PCC 6803. PLoS One.7:e48285, Oct. 2012.

Sawasaki and Endo, "The wheat germ cell-free protein synthesis system," Cell-Free Protein Syn. 111-139, Jul. 2008.

Sawasaki et al., "A bilayer cell-free protein synthesis system for high-throughput screening of gene products," FEBS Lett. 514:102-105, Mar. 2002.

Sawasaki et al., "A cell-free protein synthesis system for high-throughput proteomics," Proc. Nat.Acad.Sci. U S A 99:14652-14657, Nov. 12 2002.

Semrau et al., "Methanobactin and MmoD work in concert to act as the 'copper-switch' in methanotrophs," Environ Microbiol. doi: 10.1111/1462-2920.12150, Apr. 29, 2013.

Semrau et al., "Methanotrophs and copper," FEMS Microbiol Rev. 34:496-531, Jul. 2010.

Shima et al., "Structure of a methyl-coenzyme M reductase from Black Sea mats that oxidize methane anaerobically," Nature. 481: 98-101, Nov. 27, 2011.

Singh et al., "Identification of an atypical membrane protein involved in the formation of protein disulfide bonds in oxygenic photosynthetic organisms," J Biol Chem. 283:15762-15770, Jun. 6, 2008.

Singh et al., "Integrative analysis of large scale expression profiles reveals core transcriptional response and coordination between multiple cellular processes in a cyanobacterium," BMC Syst Biol 4:105, Aug. 2010.

Sitaraman and Chatterjee, "High-throughput protein expression using cell-free system," Meth. Mol. Biol. 498:229-244, 2009.

Smith et al., "Heterologous expression of alkene monooxygenase from *Rhodococcus rhodochrous* B-276," Eur J Biochem. 260:446-52, Mar. 1999.

Sonnhammer et al., "Pfam: a comprehensive database of protein domain families based on seed alignments," Proteins, 28 :405-420, Jul. 1997.

Sonnhammer et al., "Pfam: multiple sequence alignments and HMM-profiles of protein domains," Nucl. Acids Res., 26:320-322, Jan. 1998.

Sorensen and Mortensen, "Advanced genetic strategies for recombinant protein expression in *Escherichia coli*," J. Biotech. 115:113-128, Jan. 26, 2005.

Taton et al., "Gene transfer in *Leptolyngbya* sp. strain BL0902, a cyanobacterium suitable for production of biomass and bioproducts," PLoS One. 7:e30901, Jan. 24, 2012.

Tinberg and Lippard, "Dioxygen activation in soluble methane monooxygenase," Acc Chem Res. 44:280-288, Apr. 19, 2011.

Tomas et al., "Transcriptional analysis of butanol stress and tolerance in Clostridium acetobutylicum," J Bacteriol. 186:2006-2018, Apr. 2004.

Toney et al., "Cyanobacterial metallochaperone inhibits deleterious side reactions of copper," Proc Natl Acad Sci USA 109:95-100, Jan. 3, 2012.

(56) References Cited

PUBLICATIONS

Wegener et al., "Global proteomics reveal an atypical strategy for carbon/nitrogen assimilation by a cyanobacterium under diverse environmental perturbations," Mol Cell Proteomics, 9:2678-89, Dec. 2010.

West et al., "Functional expression in *Escherichia coli* of proteins B and C from soluble methane monooxygenase of Methylococcus capsulatus (Bath)," J Gen Microbiol. 138:1301-1307, Jul. 1992.

Weyer et al., "Theoretical maximum algal oil production," Bioenerg. Res. 3: 204-213, Oct. 2010.

Yaeta and Tatsuya, "High-throughput, genome-scale protein production method based on the wheat germ cell-free expression system," Biotech. Adv. 21:695-713, Nov. 2003.

Zhang et al., "Copper-mediated regulation of cytochrome c553 and plastocyanin in the cyanobacterium Synechocystis 6803," J Biol Chem. 267:19054-19059, Sep. 25, 1992.

Alvey et al., "Effects of modified Phycobilin biosynthesis in the Cyanobacterium *Synechococcus* sp. Strain PCC 7002," J. Bacteriol., 193(7):1663-1671, Apr. 2011.

Guerrero et al., "Ethylene synthesis and regulated expression of recombinant protein in *Synechocystis* sp. PCC 6803," PLoS One, 7(11):e50470, Nov. 2012.

Lan et al., "Metabolic engineering of cyanobacteria for 1-butanol production from carbon dioxide," Metab. Eng.,13(4):353-363, Jul. 2011.

Li et al., "Engineering a cyanobacterium as the catalyst for the photosynthetic conversion of CO2 to 1,2-propanediol," Microb. Cell Fact., 12(4):1-9, Jan. 2013.

Lindberg et al., "Engineering a platform for photosynthetic isoprene production in cyanobacteria, using Synechocystis as the model organism," Metab. Eng., 12(1):70-79, Jan. 2010.

Liu et al., "Fatty acid production in genetically modified cyanobacteria," Proc. Natl. Acad. Sci. U.S.A., 108(17):6899-904, Apr. 2011.

Ruffing, "Engineered cyanobacteria: teaching an old bug new tricks," Bioeng. Bugs., 2(3):136-149, May 2011.

Savakis et al., "Synthesis of 2,3-butanediol by *Synechocystis* sp. PCC6803 via heterologous expression of a catabolic pathway from lactic acid- and enterobacteria," Metab. Eng., 20:121-130, Nov. 2013.

Varman et al., "Metabolic engineering of *Synechocystis* sp. strain PCC 6803 for isobutanol production," Appl. Environ. Microbiol., 79(3):908-14, Feb. 2013.

Wang et al., "Application of synthetic biology in cyanobacteria and algae," Front. Microbiol., 3:344, Sep. 2012.

Xu (Dissertation submitted at the Pennsylvania State University Graduate School, Department of Biochemistry and Molecule Biology, Aug. 2010.

Yu et al., "Development of *Synechocystis* sp. PCC 6803 as a phototrophic cell factory," Mar. Drugs, 11(8):2894-916, Aug. 2013.

\* cited by examiner

# METABOLICALLY ENGINEERED METHANOTROPHIC, PHOTOTROPHIC MICROORGANISMS

CROSS-REFERENCE TO RELATED APPLICATIONS

This application claims priority to U.S. Provisional Patent Application Ser. No. 61/891,032, filed Oct. 15, 2013, the entire contents of which are incorporated herein by reference.

GOVERNMENT LICENSE RIGHTS

The invention was made with government support by the Advanced Research Projects Agency of the Department of Energy. The government has certain rights in the invention.

TECHNICAL FIELD

This disclosure relates to the engineering of phototrophic microorganisms for conversion of alkanes into high-value products. In particular, this disclosure relates to the production of alcohols such as butanols from methane using recombinant phototrophic organisms such as cyanobacteria.

BACKGROUND

The increasing reserves of natural gas combined with its availability in different geographical locations have generated a great interest in development of processes for its economical transformation into energy-dense liquid transportation fuel and products. Methane is the principal component of natural gas and thus development of economical and sustainable strategies for utilization of methane is of significance. A well-recognized process is oxidative transformation of methane into methanol. Partial oxidation of methane to synthesis gas followed by the Fischer-Tropsch chemistry is a well established chemical transformation process. However, it involves multiple components which results in high capital costs and the conversion efficiency is generally poor. This limits its utility only in geographical locations with large natural gas reserves.

Although methanotrophs belonging to alpha- and gamma-proteobacteria are known to utilize methane as a sole source of carbon and energy, there are many challenges in the use of methanotrophs based bioprocess technology for production of high-value products from methane. These organisms obtain the necessary energy for metabolic activities including the initial oxidation of methane by converting a large amount of methane into $CO_2$ which results in loss of methane and generation of greenhouse gas. Therefore, there are great challenges in leveraging these organisms for commercial applications to convert natural gas into products useful in petrochemical, material and energy industries.

SUMMARY

Provided herein are recombinant phototrophic microorganisms, comprising one or more alkane oxidation genes whose expression results in oxidation of alkanes and assimilation of the resulting products into the central metabolic pathways in phototrophic organisms such as cyanobacteria. The one or more alkane oxidation genes can be an alkane monooxygenase, an alcohol dehydrogenase or an aldehyde assimilatory gene. The recombinant photosynthetic organism converts the entire feed of alkane into the targeted product because it uses sunlight to provide energy and oxygen needed for oxidation of alkanes. Having the ability to couple oxidation of alkanes such as methane with sunlight in the recombinant phototrophic organism and energy can allow molecules of interest (e.g., butanol) to be produced biologically from natural gas in an efficient and cost effective manner. Because the recombinant phototrophic organism converts alkanes into metabolic products that are natively part of central metabolic pathway of all living organisms, the recombinant photosynthetic microorganisms or organisms provided herein can be further genetically modified with previously known polypeptides in the art whose expression converts metabolites from central metabolic pathways into several molecules including, but not limited to, amino acids, alcohols, dicarboxylic acids, fatty acids, energy-dense molecules and other molecules useful in petrochemical, material and energy industries efficiently and at high levels. Production processes involving phototrophic microorganisms are carried out under moderate conditions, use simpler and potentially more selective reactions, and have the potential to be operationally implemented at different scales for economical production of energy-dense transportation fuels at different geographical locations.

In one aspect, provided herein is a recombinant phototrophic microorganism, comprising one or more genes encoding a methane monooxygenase (MMO). The MMO can be a particulate MMO, and the one or more genes can comprise coding sequences for polypeptides having the amino acid sequences of *Methylococcus capsulatus* Bath PmoA, PmoB, and PmoC. The MMO can be a soluble MMO and the one or more genes can comprise coding sequences for an MmoX polypeptide; an MmoY polypeptide, an MmoB polypeptide, an MmoZ polypeptide, an MmoD, and an MmoC polypeptide. The expression of said one or more genes in the recombinant microorganism can result in the production of methanol; ethanol; propanol, or n-butanol, when the microorganism is grown in the presence of light and $O_2$ in a medium comprising methane, ethane, propane or butane, respectively.

The recombinant microorganism can further include a methanol dehydrogenase or a human class I alcohol dehydrogenase; a hexulose-6-phosphate synthase and a 6-phosphate-3-hexuloisomerase; and recombinant genes encoding an acetyl-CoA acetyltransferase polypeptide; a 3-hydroxybutyryl-CoA dehydrogenase polypeptide; a 3-hydroxybutyryl-CoA dehydratase (crotonase) polypeptide; an aldehyde/alcohol dehydrogenase polypeptide; and a trans-enoyl-CoA reductase polypeptide. Expression of these genes in the microorganism can result in the production of n-butanol when the microorganism is grown in the presence of light and $O_2$ in a medium comprising methane.

In another aspect, also provided herein is a recombinant phototrophic microorganism, comprising one or more genes encoding a methanol dehydrogenase (MDH) or a human class I alcohol dehydrogenase. The one or more genes can be a gene encoding a human class I ADH1A, ADH1B, and ADH1C alcohol dehydrogenase. The recombinant microorganism can be a strain of cyanobacterium or algae, e.g., a *Synechocystis* species. The one or more genes can comprise a gene encoding a polypeptide having the amino acid sequence of an NAD-dependent MDH from methylotrophic *Bacillus methanolicus*. The recombinant microorganism can further include a gene encoding a hexulose-6-phosphate synthase (HPS) and a gene encoding a 6-phosphate-3-hexuloisomerase (PHI), and be capable of growth in media containing 2% (v/v) methanol. In addition to a gene encoding a hexulose-6-phosphate synthase and a gene encoding a 6-phosphate-3-hexuloisomerase, such a recombinant microorganism can further include recombinant genes encoding an acetyl-CoA acetyltransferase polypeptide; a 3-hydroxybutyryl-CoA dehydrogenase polypeptide; a 3-hydroxybutyryl-CoA dehydratase (crotonase) polypeptide; an aldehyde/alcohol dehydrogenase polypeptide; and a trans-enoyl-CoA reductase polypeptide. Expression of such genes in the microorganism can result in the production of n-butanol when the microorganism is grown in the presence of light and $O_2$ in a medium comprising methanol.

In another aspect, also provided herein is a recombinant phototrophic microorganism, comprising one or more genes encoding a hexulose-6-phosphate synthase (HPS) or a 6-phosphate-3-hexuloisomerase (PHI). At least one of the HPS and PHI genes can encode a polypeptide having the amino acid sequence of an HPS or PHI from *Methylococcus capsulatus, Bacillus methanolicus,* or *Pyrococcus horikoshii*. The recombinant phototrophic microorganism can be capable of growth in media containing 15 mM formaldehyde. The rate of growth of the microorganism in media containing 15 mM formaldehyde can be about 88% or more, relative to the rate of growth of the microorganism in corresponding media containing no added formaldehyde. The amount of formaldehyde in supernatant from media in which the microorganism has been cultured can be about 4-fold less than the amount of formaldehyde in supernatant from media in which isogenic control cells have been cultured. The recombinant microorganism can further comprise a gene encoding a phosphoribulokinase, and/or can further comprise one or more genes encoding a phosphoribulokinase; a transketolase, a transaldolase, and/or a sedoheptulose-1,7-bisphosphatase. The microorganism can be a strain of cyanobacterium or alga, such as a *Synechocystis* species.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DESCRIPTION OF THE SEQUENCE LISTING

Figure 1:
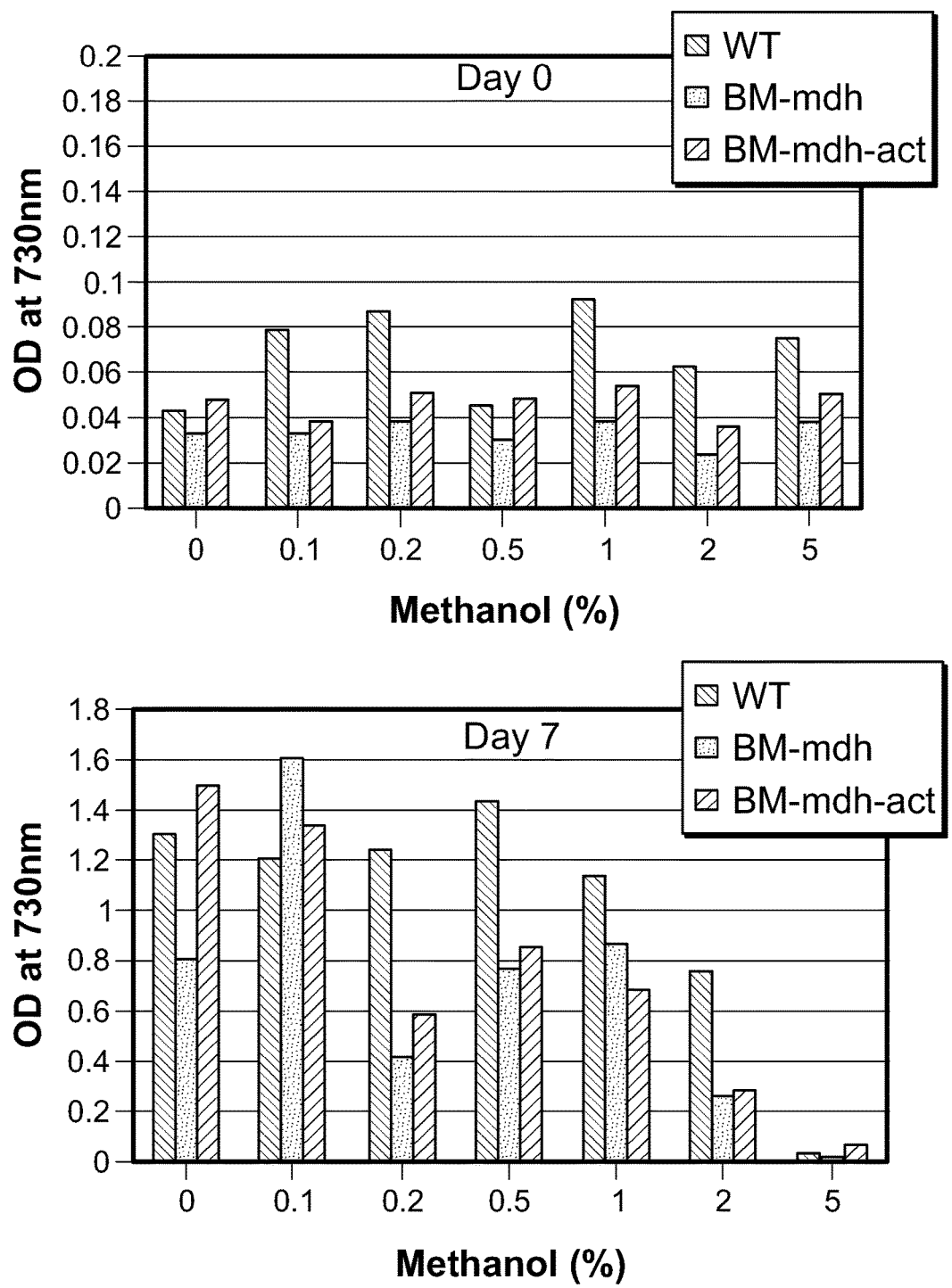
FIG. 1 is a bar graph showing the optical density of *Synechocystis* cultures at 0 days and at 7 days of growth after 7 days of growth at 30° C. in media containing different concentrations of methanol. Optical density was monitored by measuring absorbance at 730 nm. WT=wild type *Synechocystis* strain lacking MDH and ACT genes; BM-mdh=*Synechocystis* strain expressing MDH gene; BM-mdh-act *Synechocystis* strain expressing MDH and ACT genes.

| Genbank No. | Species | SEQ ID NO: |
|---|---|---|
| GI: 53804130 | *Methylococcus capsulatus* | 1 |
| GI: 7188931 | *Methylosinus trichosporium* | 2 |
| GI: 427190913 | *Methylohalobius crimeensis* | 3 |
| GI 357403888 | *Methylomicrobium alcaliphilum* | 4 |
| GI: 402774099 | *Methylocystis sp.* | 5 |
| GI: 223717937 | *Methylococcaceae bacterium* | 6 |
| GI: 224967033 | *Methylomarinum vadi* | 7 |
| GI: 7188938 | *Methylocystis sp.* | 8 |
| GI: 7188933 | *Methylosinus trichosporium* | 9 |
| GI: 83308654 | uncultured bacterium | 10 |
| GI: 189219600 | *Methylacidiphilum infernorum* | 11 |
| GI: 83308708 | *Methylocapsa acidiphila* | 12 |
| GI:53804139 | *Methylococcus capsulatus* | 13 |
| GI 7188932 | *Methylosinus trichosporium* | 14 |
| GI 189219602 | *Methylacidiphilum infernorum* | 15 |
| GI 83308706 | *Methylocapsa acidiphila* | 16 |
| GI 357403887 | *Methylomicrobium alcaliphilum* | 17 |
| GI 402774098 | *Methylocystis sp.* | 18 |
| GI 6013166 | *Methylocystis sp.* | 19 |
| GI 53758445 | *Methylococcus capsulatus* | 20 |
| GI 73745618 | *Methylosinus trichosporium* | 21 |
| GI 89572582 | *Methylomicrobium japanense* | 22 |
| GI 74381909 | *Methylocella silvestris* | 23 |
| GI 5102756 | *Methylosinus trichosporium* | 24 |
| GI 88656492 | *Methylosinus sporium* | 25 |
| GI 6013167 | *Methylocystis sp.* | 26 |
| GI 53804675 | *Methylococcus capsulatus* | 27 |
| GI 306921972 | *Methylovulum miyakonense* | 28 |
| GI 73745619 | *Methylosinus trichosporium* | 29 |
| GI 2098696 | *Methylocystis sp.* | 30 |
| GI 88656493 | *Methylosinus sporium* | 31 |
| GI 6013168 | *Methylocystis sp.* | 32 |
| GI 6002406 | *Methylomonas sp.* | 33 |
| GI 7770068 | *Methylococcus capsulatus* | 34 |
| GI 89572584 | *Methylomicrobium japanense* | 35 |
| GI 53804674 | *Methylococcus capsulatus* | 36 |
| GI 306921973 | *Methylovulum miyakonense* | 37 |
| GI 73745620 | *Methylosinus trichosporium* | 38 |
| GI 88656494 | *Methylosinus sporium* | 39 |
| GI 6013169 | *Methylocystis sp.* | 40 |
| GI 7770067 | *Methylococcus capsulatus* | 41 |
| GI 53804672 | *Methylococcus capsulatus* | 42 |
| GI 19855848 | *Methylococcus capsulatus* | 43 |
| GI 306921974 | *Methylovulum miyakonense* | 44 |
| GI 73745621 | *Methylosinus trichosporium* | 45 |
| GI 88656496 | *Methylosinus sporium* | 46 |
| GI 6013171 | *Methylocystis sp.* | 47 |
| GI 21362649 | *Methylosinus trichosporium* | 48 |
| GI 18266834 | *Methylococcus capsulatus* | 49 |
| GI 245216 | *Methylosinus trichosporium* | 50 |
| GI 7770065 | *Methylococcus capsulatus* | 51 |
| GI 53804670 | *Methylococcus capsulatus* | 52 |
| GI 73745623 | *Methylosinus trichosporium* | 53 |
| GI 88656495 | *Methylosinus sporium* | 54 |
| GI 141050 | *Methylococcus capsulatus* | 55 |
| GI 21362648 | *Methylosinus trichosporium* | 56 |
| GI 53804671 | *Methylococcus capsulatus* | 57 |
| GI 53758432 | *Methylococcus capsulatus* | 58 |
| GI 74381913 | *Methylocella silvestris* | 59 |
| GI 462590 | *Bacillus methanolicus* | 60 |
| GI 41057056 | *Bacillus methanolicus* | 61 |
| GI 387585284 | *Bacillus methanolicus* | 62 |
| GI 143175 | *Bacillus sp.* | 63 |
| GI 22654852 | *Bacillus methanolicus* | 64 |
| GI 4501929 | *Homo sapiens* | 65 |
| GI 50960621 | *Homo sapiens* | 66 |
| GI 34577061 | *Homo sapiens* | 67 |
| GI 4501933 | *Homo sapiens* | 68 |
| GI 53802837 | *Methylococcus capsulatus* | 69 |
| GI 170781838 | *Clavibacter michiganensis subsp.* | 70 |

-continued

| Genbank No. | Species | SEQ ID NO: |
|---|---|---|
| GI 53756598 | Methylococcus capsulatus str. | 71 |
| GI 169156406 | Clavibacter michiganensis subsp. | 72 |
| GI 49482799 | Staphylococcus aureus subsp. | 73 |
| GI 15923560 | Staphylococcus aureus subsp. | 74 |
| GI 56416177 | Salmonella enterica subsp. | 75 |
| GI 56415567 | Salmonella enterica subsp. | 76 |
| GI 89089643 | Bacillus sp. | 77 |
| GI 40074227 | Bacillus methanolicus | 78 |
| GI 333985721 | Methylomonas methanica | 79 |
| GI 53756597 | Methylococcus capsulatus str. | 80 |
| GI 390191152 | Desulfurococcus fermentans | 81 |
| GI 327400808 | Archaeoglobus veneficus | 82 |
| GI 373906366 | Methanoplanus limicola | 83 |
| GI 544229974 | Lactobacillus brevis | 84 |
| GI 410600419 | Methanobacterium sp. | 85 |
| GI 18976592 | Pyrococcus furiosus | 86 |
| GI 20905670 | Methanosarcina mazei | 87 |
| GI 124363810 | Methanocorpusculum labreanum | 88 |
| GI 124363357 | Methanocorpusculum labreanum | 89 |
| GI 351717933 | Methylomicrobium alcaliphilum | 90 |
| GI 18892157 | Methylomicrobium alcaliphilum | 91 |
| GI 387585261 | Bacillus methanolicus | 92 |
| GI 387587408 | Bacillus methanolicus | 93 |
| GI 14591680 | Pyrococcus horikoshii | 94 |
| GI 387587407 | Bacillus methanolicus | 95 |

DETAILED DESCRIPTION

This document provides methods and materials to metabolically engineer photosynthetic organisms such as cyanobacteria, such that oxidation of alkanes is coupled with energy derived from sunlight for cost-effective biological conversion of such alkanes into high-value products (e.g., butanol). The ability of the engineered microorganism to utilize sunlight as the source of energy for metabolic activities provides a method to convert the entire feed of alkane into targeted product while ability of the recombinant phototrophic organism to provide photosynthetically produced oxygen from water as an in situ generated substrate for the activation of alkane reduces the equipment cost.

This document provides methods and materials for using recombinant phototrophic organisms (e.g., cyanobacteria such as a Synechocystis species) designed to express a polypeptide having alkane monooxygenase activity that is localized to either the cytoplasmic membrane or in soluble form that converts alkanes into their respective alcohols (e.g., methane into methanol) or both i.e., a recombinant organism can carry both forms of alkane monooxygenase activity. As described herein, polypeptides (e.g., polypeptides having enzymatic activity) can be designed to include a membrane-targeting sequence that allows the polypeptide to be localized to a membrane. Similarly, a polypeptide having alcohol dehydrogenase activity can be expressed that converts alcohols into their respective aldehydes (e.g., methanol to formaldehyde), and a polypeptide having aldehyde assimilation activity that converts an aldehyde into a metabolite of central metabolic pathways (e.g., formaldehyde into 3-phosphoglycerate). The ability of the engineered phototrophic organisms to convert alkanes such as methane into intermediates of a central metabolic pathway allows one to produce any products including, but not limited to, amino acids, alcohols, dicarboxylic acids, fatty acids, and energy-dense molecules from the alkanes efficiently and at high levels.

As used herein, the term recombinant microorganism refers to a microorganism, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant microorganism. It will be appreciated that typically the genome of a recombinant microorganism described herein is augmented through the stable introduction of one or more recombinant genes that are not originally resident in the microorganism that is the recipient of the DNA. However, it is within the scope of the invention to isolate a DNA segment from a given microorganism, and to subsequently introduce one or more additional copies of that DNA back into the same microorganism, e.g., to enhance production of the product of a gene or alter the expression pattern of a gene. In some instances, the introduced DNA will modify or even replace an endogenous gene or DNA sequence by, e.g., homologous recombination or site-directed mutagenesis.

The term "recombinant gene" refers to a gene or DNA sequence that is introduced into a recipient microorganism, regardless of whether the same or a similar gene may already be present in such a microorganism. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a microorganism by genetic engineering methods to form a recombinant microorganism. It will be appreciated that a recombinant gene that is introduced into a microorganism can be identical to a DNA sequence that is normally present in the microorganism being transformed, and is introduced to provide one or more additional copies of the DNA to thereby permit overexpression or modified expression of the gene product of that DNA. Recombinant genes typically encode one or more polypeptides.

It will be appreciated that functional homologs of the said polypeptides are also suitable for use in generation of the said recombinant microorganism. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Functional homologs can also be created via site-directed mutagenesis of the coding sequence for a naturally occurring polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of the said polypeptides such as alkane monooxygenase. Sequence analysis can involve BLAST, Reciprocal BLAST, or PSI-BLAST analysis of nonredundant databases using an alkane monooxygenase polypeptide amino acid sequence as the reference sequence. Amino acid sequence is, in some instances, deduced from the nucleotide sequence. Those polypeptides in the database that have greater than 40% sequence identity are candidates for further evaluation for suitability as a polypeptide representing specific function described in this invention. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in the said polypeptides, e.g., conserved functional domains.

Conserved regions can be identified by locating a region within the primary amino acid sequence of the said polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

It will be appreciated that functional homologs of the polypeptides described below are also suitable for use in generation of a recombinant microorganism in which functional expression of the said polypeptides enables the recombinant microorganism to utilize alkane as a sole source of carbon and energy.

Alkane Oxidation Polypeptides

Alkanes can be oxidized by a number of enzymes including methane monooxygenase (MMO), alkene monooxygenase and cytochrome P450s. There are two known forms of MMO: a cytoplasmic membrane localized form known as particulate MMO (pMMO) (EC 1.14.18.3) and a cytoplasmic soluble form known as soluble MMO (sMMO) (EC 1.14.13.25). Both MMOs are able to break the C—H bonds present in alkanes, although their structure, subunit composition and catalytic mechanism are different. Most methanotrophs contain only pMMO but some also have both pMMO and sMMO.

pMMOs are generally more selective in their ability to react with various substrates whereas sMMOs generally are able to react with a broader range of substrates. sMMOs typically can utilize hydrocarbons up to C8 as substrates, including aromatic and chlorinated hydrocarbons. pMMO is composed of three polypeptides (PmoA, PmoB and PmoC) and the active form of the enzyme is in a $(\alpha\beta\gamma)_3$ configuration. The nucleic acids encoding pMMO subunits typically are part of a conserved operon among methanotrophs. Some methanotrophs contain a single copy of the operon whereas others contain multiple copies. Multiple pmo operon clusters in a single methanotroph often encode divergent pMMO enzymes that have varying reaction rates for oxidation of methane into methanol.

It have been suggested that the active site of pMMO may contain either diiron, tricopper or dicopper centers depending on the methanotrophic organism. Recent crystal structures of certain pMMOs indicate that a dicopper center in the soluble cupridoxin domains in PmoB is involved in methane hydroxylation. The soluble domain of PmoB expressed in *E. coli* can catalyze propylene epoxidation and methane oxidation. PmoA and PmoC also contain metals (zinc in PmoA and PmoC subunits from *Methylococcus capsulatus* Bath and iron in PmoA and PmoC subunits from *Methylosinus trichosporium* OB3b).

Methanotrophs have developed specialized mechanisms to mobilize and acquire copper from their environment for pMMO function. A small chromopeptide known as methanobactin is involved in copper delivery to pMMO. Thus, in some embodiments, the open reading frames in the methanobactin biosynthetic gene cluster can be codon optimized for a desired phototrophic microorganism, and the optimized sequences introduced into and expressed in that microorganism, thereby facilitating copper acquisition for pMMO activity. Although the involvement of copper in function of pMMO has been universally recognized, not all methanotrophs appear to have methanobactin. This suggests that alternate systems can be utilized to acquire and deliver copper to pMMO.

PmoA is one of the three polypeptides of pMMO and has been suggested to be involved in stabilization of pMMO as well as a role in electron transfer from electron carrier to the active site. Examples of the pmoA sequences can be found under the following GenBank accession numbers: YP_114235.1 (GI: 53804130), AAA87220.2 (GI: 7188931), BAM71040.1 (GI: 427190913), YP_004915812.1 (GI: 357403888), YP_006593636.1 (GI: 402774099), BAH22845.1 (GI: 223717937), BAF62077.2 (GI: 224967033).

PmoB is another of the three polypeptides of pMMO. This polypeptide contains the active center where actual methane hydroxylation takes place. Various pmoB sequences can be found under the following GenBank accession numbers: AAF37897.1 (GI: 7188938), AAF37894.1 (GI: 7188933), CAJ01562.1 (GI: 83308654), YP_001940241.1 (GI: 189219600), CAJ01618.1 (GI: 83308708), YP_114234.1 (GI: 53804139).

PmoC is the third of the three polypeptides of pMMO. It has been suggested that PmoC is involved in stabilization of pMMO as well as having a role with electron transfer. Various pmoC sequences can be found under the following GenBank accession numbers: AAF37893.1 (GI: 7188932), YP_001940243.1 (GI: 189219602), CAJ01616.1 (GI:

83308706), YP_004915811.1 (GI: 357403887), YP_006593635.1 (GI: 402774098).

sMMO (EC 1.14.13.25) is a multi-component enzyme containing a hydroxylase component, a reductase component and a regulatory component. The hydroxylase component is composed of three subunits in a $(\alpha\beta\gamma)_2$ configuration. The catalytic site of sMMO resides on a subunit of the hydroxylase component and contains a carboxylate-bridged diiron center. The reductase component contains an FAD and [2Fe-2S] ferredoxin domains and provides electrons to hydroxylase by oxidizing NADH to $NAD^+$. The regulatory component has been suggested to be involved in regulation of electron flow from the reductase component to the hydroxylase component.

Coding sequences for sMMO are organized in a conserved cluster and contain the following genetic loci: mmoX (encodes a subunit of hydroxylase component), mmoY (encodes β subunit of hydroxylase component), mmoB (encodes regulatory component), mmoZ (encodes γ subunit of hydroxylase component), mmoD (encodes a polypeptide of unknown function), and mmoC (encodes the reductase component).

The MmoX polypeptide is one of the subunits of the hydroxylase component of sMMO. It contains the active center which lies in a four-helix bundle. Examples of the mmoX sequences can be found under the following GenBank accession numbers: AAF01268.1 (GI: 6013166), AAU92736.1 (GI: 53758445), AAZ81968.1 (GI: 73745618), BAE86875.1 (GI: 89572582), CAJ26291.1 (GI: 74381909), CAA39068.2 (GI: 5102756).

The MmoY polypeptide is another of the subunits of the hydroxylase component of sMMO. Various mmoY sequences can be found under the following GenBank accession numbers: ABD46893.1 (GI: 88656492), AAF01269.1 (GI: 6013167), YP_113660.1 (GI: 53804675), BAJ17646.1 (GI: 306921972), AAZ81969.1 (GI: 73745619), AAC45290.1(GI: 2098696).

The MmoB polypeptide is the regulatory component. It regulates transfer of electrons from component C to the hydroxylase component. Various mmoB sequences can be found under the following GenBank accession numbers: ABD46894.1 (GI: 88656493), AAF01270.1 (GI: 6013168), BAA84759.1 (GI: 6002406), AAF04158.2 (GI: 7770068), BAE86877.1 (GI: 89572584), YP_113661.1 (GI: 53804674), BAJ17647.1 (GI: 306921973), AAZ81970.1 (GI: 73745620).

The MmoZ polypeptide is the third of the subunits of the hydroxylase component of sMMO. Various mmoZ sequences can be found under the following GenBank accession numbers: ABD46895.1 (GI: 88656494), AAF01271.1 (GI: 6013169), AAF04157.2 (GI: 7770067), YP_113663.1 (GI: 53804672), P11987.4 (GI: 19855848), BAJ17648.1 (GI: 306921974), AAZ81971.1 (GI: 73745621).

The MmoC polypeptide is the reductase component. It contains FAD and a [2Fe-2S] cluster and is involved in transfer of electrons from NADH to the hydroxylase component. Various mmoC sequences can be found under the following GenBank accession numbers: ABD46897.1 (GI: 88656496), AAF01273.1 (GI: 6013171), Q53563.1 (GI: 21362649), P22868.2 (GI: 18266834), AAB21393.1 (GI: 245216), AAB62391.2 (GI: 7770065), YP_113665.1 (GI: 53804670), AAZ81973.1 (GI: 73745623).

The MmoD polypeptide is suggested to be involved in regulation of sMMO by sensing the availability of copper. Various mmoS sequences can be found under the following GenBank accession numbers: ABD46896.1 (GI: 88656495), P22867.1 (GI: 141050), Q53562.1 (GI: 21362648), YP_113664.1 (GI: 53804671), AAU92723.1 (GI: 53758432), CAJ26295.1 (GI: 74381913).

Methanol Dehydrogenase

Conversion of methanol into formaldehyde can be accomplished by methanol dehydrogenase (MDH). Multiple classes of methanol dehydrogenases are known including pyrroloquinoline quinone (PQQ) dependent MDH found in the Gram negative methanotrophs and methylotrophs, NAD-dependent MDH in methylotrophic *Bacillus* strains, and class I alcohol dehydrogenase (ADH) in human and other animals. In methylotrophic yeast, oxidation of methanol is carried out by alcohol oxidase along with catalase in peroxisomes. Alcohol oxidase consists of eight identical subunits with each subunit containing one FAD as prosthetic group. PQQ-MDH is localized in periplasm and contains two subunits forming $\alpha_2\beta_2$ structure. The entire biosynthetic pathway for synthesis of PQQ and MDH subunits is part of a large cluster containing at least 10 genes.

Methylotrophic *Bacillus* strains contain an NAD-dependent MDH enzyme which consists of 10 subunits of an identical polypeptide. Class I ADH is another diverse group of enzymes that can catalyze conversion of methanol into formaldehyde using NAD as cofactor. Human class I ADH enzymes can exist in either the homodimer or the heterodimer form of α, β, and γ subunits encoded by ADH1A, ADH1B and ADH1C genes.

Methanol dehydrogenase or alcohol dehydrogenase genes encode polypeptides that convert methanol into formaldehyde. Various mdh or adh sequences can be found under the following GenBank accession numbers: P31005.3 (GI: 462590), NP_957659.1 (GI: 41057056), EIJ77618.1 (GI: 387585284), AAA22593.1 (GI: 143175). Additional polypeptides that provide a regulatory function can also be included if desired. Sequences for such polypeptides can be found under the following GenBank accession numbers: AAM98772.1 (GI: 22654852)

Various class I adh sequences can be found under the following GenBank accession numbers: NP_000658.1 (GI: 4501929), AAH74738.1 (GI: 50960621), NP_000659.2 (GI: 34577061), NP_000660.1 (GI: 4501933).

Assimilation of Formaldehyde

Assimilation of formaldehyde in methanotrophic and methylotrophic organisms is accomplished primarily by two pathways: the serine pathway and the RuMP pathway. In the serine pathway, formaldehyde reacts with glycine to form serine. It goes through a series of cyclic reactions leading to the production of 3-phosphoglycerate. The net balance of serine cycle is the fixation of two molecules of formaldehyde and 1 molecule of $CO_2$ into 1 molecule of 3-phosphoglycerate using 2 molecules each of ATP and NAD(P)H.

In the RuMP pathway, formaldehyde is condensed with D-ribulose 5-phosphate by hexulose-6-phosphate synthase (HPS) to form hexulose 6-phosphate which is then isomerized by 6-phosphate-3-hexuloisomerase (PHI) to form D-fructose 6-phosphate. The product of PHI is fed into the central metabolic pathway via the reductive pentose phosphate pathway. HPS and PHI are mostly unique to methanotrophs. The overall reaction is the fixation of three molecules of formaldehyde into 1 molecule of 3-phosphoglycerate using 1 molecule of ATP.

Various hps sequences can be found under the following GenBank accession numbers: YP_115430.1 (GI: 53802837), YP_001710170.1 (GI: 170781838), AAU90889.1 (GI: 53756598), CAQ01554.1 (GI: 169156406), YP_040023.1 (GI: 49482799), NP_371094.1 (GI: 15923560), YP_153252.1 (GI: 56416177), YP_152642.1 (GI: 56415567), EAR68750.1 (GI: 89089643), AAR39392.1 (GI: 40074227).

Various phi sequences can be found under the following GenBank accession numbers: YP_004514931.1 (GI: 333985721), AAU90888.1 (GI: 53756597), AFL66208.1 (GI: 390191152), YP_004341647.1 (GI: 327400808), EHQ34470.1 (GI: 373906366), ERK43186.1 (GI: 544229974), EKQ54947.1 (GI: 410600419).

In some cases, HPS and PHI enzymatic activities are present in a single polypeptide. Various hps-phi sequences can be found under the following GenBank accession numbers: NP_577949.1 (GI: 18976592), AAM30911.1 (GI: 20905670), ABN07618.1 (GI: 124363810), ABN07165.1 (GI: 124363357), CCE23598.1 (GI: 351717933), AAL80344.1 (GI: 18892157).

The RuMP pathway is energetically more efficient compared to the serine pathway. This is also reflected in the growth yield experimentally established for organisms utilizing either RuMP pathway (~0.55 CDW/g methanol) or serine pathway (~0.4 g CDW/g methanol). Most methanotrophs contain separate genes for HPS and PHI, however, Archaeon *Pyrococcus horikoshii* contains a single gene encoding both functions.

Genes

A gene encoding a polypeptide described herein comprises the coding sequence for that polypeptide, operably linked in sense orientation to one or more regulatory regions suitable for expressing the polypeptide. Because many microorganisms are known to encode multiple proteins of a pathway in a polycistronic unit, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

It will be appreciated that it may be desirable to remove or replace certain regulatory regions in order to increase expression levels. For example, it may be desirable to remove regions of genes encoding sMMO polypeptides so that expression of these polypeptides is not under the control of the presence of copper and that it can be expressed simultaneously with membrane localized pMMO polypeptides.

One or more genes can be combined in a recombinant nucleic acid construct in "modules" useful for a discrete aspect of generation of recombinant phototrophic organism. Combining a plurality of genes in a module, particularly a polycistronic module, facilitates the use of the module in a variety of species. For example, an alkane oxidation gene cluster, an alcohol dehydrogenase gene and an aldehyde assimilatory gene can be combined in a polycistronic module such that, after insertion of a suitable regulatory region, the module can be introduced into a wide variety of industrial microorganisms. In addition to genes useful for oxidation of alkanes and its assimilation into the central metabolic pathways, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular microorganism is obtained, using appropriate codon bias tables for that microorganism, and codon-optimized nucleic acids are typically used when the polypeptide to be expressed is heterologous for that microorganism.

In some cases, it is desirable to inhibit one or more functions of an endogenous polypeptide. For example, it may be desirable to inhibit or reduce conversion of ribulose 5-monophosphate to ribulose 1-5-bisphosphate using recombinant techniques. In such cases, a nucleic acid that inhibits or suppresses expression of a protein involved in conversion may be included in a recombinant construct that is then transformed into the strain.

Microorganisms

A number of prokaryotes and eukaryotes are suitable for use in constructing the recombinant microorganisms described herein, e.g., cyanobacteria and algae, such as oxygenic phototrophic cyanobacteria and algae. In some embodiments, non-phototrophic organisms such as yeast and fungi can also be used to express the polypeptide to achieve the oxidation of alkanes. Typically, a species and strain selected for oxidation of alkanes is first analysed to determine which needed genes are endogenous to the strain and which needed genes are not present. Genes for which an endogenous counterpart is not present in the strain are assembled in one or more recombinant constructs, which are then transformed into the strain in order to supply the missing function(s). Genes for which an endogenous counterpart is present in the strain can, if desired, be modified as described above or supplemented with one or more recombinant genes in order to enhance flux in the strain through particular pathways or particular steps.

Examples of algae that can be engineered to include one or more polypeptides designed to oxidize alkanes into central metabolic pathway intermediates include, without limitation, green algae (Chlorophyceae), red algae (Rhodophyceae), and dinoflagellates (Dinophyta). In some embodiments, a suitable alga is from a genus of Chlorophyta such as *Chlamydomonas, Dunaliella, Scenedesmus, Chlorella, Prototheca, Botryococcus, Haematococcus, Isochrysis, Tet-* raselmis, Skeletonema, Thalassiosira, Phaeodactylum, Chaetoceros, Cylindrotheca, Bellerochea, Actinocyclus, Nitzchia, Cyclotella, Isochrysis, Pseudoisochrysis, Dicrateria, Monochrysis, Tetraselmis, Pyramimonas, Micromonas, Chroomonas, Cryptomonas, Rhodomonas, Olisthodiscus, and Carteria.

Examples of photosynthetic organisms such as cyanobacteria that can be engineered to include one or more polypeptides designed to oxidize alkanes into central metabolic pathway intermediates include, without limitation, cyanobacteria from a genus such as Chamaesiphon, Chroococcus, Cyanobacterium, Cyanobium, Dactylococcopsis, Gloeobacter, Gloeocapsa, Gloeothece, Microcystis, Prochlorococcus, Prochloron, Synechococcus, Synechocystis, Chroococcidiopsis, Cyanocystis, Dermocarpella, Myxosarcina, Pleurocapsis, Stanieria, Xenococcus, Arthrospira, Borzia, Crinalium, Geitlerinema, Halospirulina, Leptolyngbya, Limnothrix, Lyngbya, Microcoleus, Oscillatoria, Planktothrix, Prochlorothrix, Pseudanabaena, Spirulina, Starria, Symploca, Trichodesmium, Tychonema, Anabaena, Anabaenopsis, Aphanizomenon, Calothrix, Cyanospira, Cylindrospermopsis, Cylindrospermum, Nodularia, Nostoc, Chlorogloeopsis, Fischerella, Geitleria, Nostochopsis, Iyengariella, Stigonema, Rivularia, Scytonema, and Tolypothri.

For example, cyanobacteria such as members of a Synechocystis species can be engineered to include one or more polypeptides designed to convert alkanes such as methane into methanol by functional expression of methane monooxygenase. The resulting methanol is converted into formaldehyde by the functional expression of methanol dehydrogenase. The resulting formaldehyde is then assimilated into 3-phosphoglycerate by the functional expression of formaldehyde assimilating polypeptides. It will be appreciated that 3-phosphoglycerate is a naturally occurring metabolite of central metabolic pathways found in all living organisms. Thus, the ability of the recombinant phototrophic organism to convert methane into a common metabolite of central metabolic pathways allows one to generate molecules of interest using the known arts of recombinant DNA technology. Such molecules, without limitation, may include amino acids, alcohols, dicarboxylic acids and any molecules currently useful in the chemical, material and energy industries.

Phototrophic microorganisms expressing recombinant genes described herein can be engineered such that methanol rather than methane can be the substrate for conversion into end products. For example, a recombinant phototrophic microorganism can be made that expresses MDH, HPS and PHI polypeptides and produces metabolic pathway intermediates such as acetyl CoA and 3-phosphoglycerate. When such a microorganism also expresses genes encoding enzymes that convert these intermediates into n-butanol, growing the microorganism on media containing methanol results in the production of n-butanol. Such a microorganism can be an oxygenic phototroph or an anoxygenic phototroph.

Methods of Producing N-Butanol

Recombinant hosts described herein can be used in methods to produce n-butanol, methanol or other desired products. For example, the method can include growing the recombinant microorganism in a culture medium under conditions in which MMO, MDH and/or formaldehyde assimilation genes are expressed. Typically, the recombinant microorganism is grown in a fermentor at a defined temperature(s) for a desired period of time. Depending on the particular microorganism used in the method, other recombinant genes such as genes for conversion of acetyl CoA to n-butanol may also be present and expressed. Levels of substrates, intermediates and/or final products can be determined by extracting samples from the culture media for analysis.

A number of different liquid media are suitable for growing recombinant phototrophic organisms in order to produce products such as n-butanol. For example, recombinant Synechocystis cells can be grown in shake flasks with constant shaking (120 rpm) in a minimal medium containing 1.5 g/L $NaNO_3$, 0.04 g/L $K_2HPO_4$, 0.075 g/L $MgSO_4.7H_2O$, 0.036 g/L $CaCl_2.2H_2O$, 0.006 g/L Citric acid, 0.006 g/L Ferric ammonium citrate, 0.001 g/L EDTA (disodium salt), 0.02 g/L $Na_2CO_3$ and 1 ml/L trace metal mix. Trace metal mix contains 2.86 g/L $H_3BO_3$, 1.81 g/L, $MnCl_2.4H_2O$, 0.222 g/L $ZnSO_4.7H_2O$, 0.39 g/L $NaMoO_4.2H_2O$, 0.079 g/L $CuSO_4.5H_2O$ and 0.0494 g/L $Co(NO_3)_2.6H_2O$.

Cells typically are grown in fermentation vessels under illumination, e.g., illuminated with cool white fluorescent light at a light intensity of about 20 µmol of photons $m^{-2} s^{-1}$ at a temperature of about 32° C. The light intensity can be from about 1 to about 200 µmol of photons $m^{-2} s^{-1}$, e.g., from about 20 to about 30 µmol of photons $m^{-2} s^{-1}$. Once cells are in the logarithmic phase, methane is fed into the vessel, the vessel is sealed air-tight, and cell growth is continued under the same culture conditions. The amount of methane converted into butanol is determined by measuring the cell density and the butanol concentration in the vessel at various times during culture. Similarly, when methanol is the substrate, the amount of methanol converted into butanol is determined by measuring the cell density and the butanol concentration in the vessel at various times during culture. In those embodiments in which methanol is the desired end product, the amount of methane converted into methanol is determined by measuring the cell density and the methanol concentration in the vessel at various times during culture.

The recombinant microorganism may be grown in a fed batch or continuous process. In the continuous mode, methane or methanol is fed into the vessel after cells have reached logarithmic phase, at a rate constant at which the cells are able to convert the substrate into intermediates and to produce the final n-butanol product.

Separation of Final Product

After the recombinant microorganism has been grown in culture for the desired period of time, the product of interest can then be recovered from the culture using various techniques. For example, n-butanol can be separated from the headspace of a fermentation vessel using distillation or pervaporation using various membranes, gas stripping, or a combination of these techniques. If n-butanol production is carried out in continuous mode, the butanol product is continuously removed by the use of extraction methods.

Purified n-butanol can then be provided to the transportation fuel industry for drop-in use in a gasoline blend. N-butanol is compatible with existing storage and distribution infrastructure, can be blended at high capacity with gasoline, and possesses fuel characteristics that are often superior to other types of biofuel. Because of these features, n-butanol can be used with minimal modifications and cost to the existing infrastructure of storage and distribution. The purified product can also be used in chemical conversion processes to make butylene, which can be used to produce specialty and commodity products as well as C12/C16 hydrocarbons for use in jet fuel.

Purified methanol can also be provided to the transportation fuel industry for drop-in use in a gasoline blend, or can be used in chemical conversion processes to make various industrial chemicals.

EXAMPLES

The invention will be further described in the following examples, which do not limit the scope of the invention described in the claims.

Example 1

Expression of Methane Monooxygenase in a Phototrophic Microorganism

Expression of methane monooxygenase in a phototrophic microorganism is accomplished via introduction of coding sequences for polypeptide subunits for either pMMO or sMMO. A number of pMMO and sMMO sequences are available from different methanotrophic organisms. For example, nucleic acids encoding the pmoCAB gene cluster (MCA1796, MCA1797 and MCA1798) or the sMMO gene cluster (MCA1194, MCA1195, MCA1196, MCA1198, MCA1199 and MCA1200) from *Methylococcus capsulatus* Bath can be operably linked to suitable promoters and introduced into *Synechocystis* sp. PCC 6803 (hereafter *Synechocystis*) to create a recombinant phototropic microorganism expressing a functional MMO. Given the different GC percent, codon utilization and differences in the regulatory sequences involved in expression and stability of messenger RNA, codon optimized genes are used for expression in *Synechocystis* and other phototropic microorganisms. Typically, such codon optimized genes are operably linked to a strong constitutive promoter.

MMO genes are transcribed polycistronically in *Methylococcus capsulatus* Bath. Therefore, these gene clusters can be assembled as polycistronic units and stably integrated in the genome of the phototrophic microorganism or can be maintained on a stably replicated plasmid. In other cases, the coding sequence for each MMO polypeptide subunit is expressed monocistronically. The use of monocistronic nucleic acids allows one to drive expression of each gene by a suitable promoter and ribosome binding site, and thus to manipulate expression of each gene individually.

The amino-terminal 32 residues of the PmoB polypeptide contain a signal peptide and in some cases it may be desirable to replace the *Methylococcus* signal peptide with, for example, a *Synechocystis* signal peptide for more efficient targeting to membranes. The initial assembly of MMO polypeptide coding sequences usually is carried out in *E. coli* such that the sequences can be targeted into the phototrophic microorganism at a single locus as previously described.

Typically, a nucleic acid construct carrying MMO coding sequences also includes an antibiotic cassette for selection of transformants carrying the MMO coding sequences. Additional coding sequences, such as coding sequences for methanobactin biosynthesis, may also be included in the recombinant construct. The recombinant construct typically is introduced into the phototrophic microorganism by transformation and targeted to a neutral site via double homologous recombination.

For *Synechocystis*, after colonies of transformants expressing mmo genes are obtained, the presence of these genes is confirmed by isolating genomic DNA and performing polymerase chain reaction using gene specific primers. *Synechocystis* can be restreaked as necessary in order to obtain isogenic lines with respect to introduced mmo genes. The steady state transcript level of each mmo gene can be determined by isolating total RNA and measuring expression of each mmo gene by real time polymerase chain reaction. Functional expression of MMO polypeptides can be determined using polyclonal antibodies against each subunit of MMOs to quantitatively measure the amount of MMO subunits in *Synechocystis*.

The enzymatic activity of MMO in the recombinant organism is measured using either methane or propylene as substrate and using gas chromatography as previously described. Because it is known that the enzymatic activity of pMMO and sMMO can be dependent on the presence of copper, the recombinant strains are grown in the presence of different concentrations of copper, and MMO activity is measured as described above. In some embodiments, coding sequences for MMO polypeptides are operably linked to copper regulated promoters so that MMO expression is coordinated with copper availability. Copper regulated promoters include those driving expression of plastocyanin and Cyt c553, two electron carriers that can carry electrons from the cytochrome bf complex to photosystem I.

Example 2

Identification of MMO Accessory Genes by Complementation of Recombinant *Synechocystis*

It may be useful to express additional polypeptides in a recombinant phototroph. To identify such proteins, a reverse approach involving complementation studies can be used to establish functional expression of MMOs in *Synechocystis*. For this, a recombinant *Synechocystis* strain is generated that expresses pMMO or sMMO polypeptides, methanol dehydrogenase polypeptides and two polypeptides that assimilate formaldehyde into 3-phosphoglycerate. The recombinant microorganism can utilize methanol as a sole source of carbon and energy. The microorganism can then be used to carry out complementation studies to identify methanotroph genes that facilitate assembly and function of MMOs in *Synechocystis*.

The complementation assay utilizes genomic DNA isolated from *Methylococcus capsulatus* Bath. Genomic DNA is partially digested with Sau3A1 to generate fragments of ~5 kb which are then cloned in a BamH1-digested plasmid that stably replicates in *Synechocystis*. The resulting library is transformed into the *Synechocystis* strain described above. Transformed cells are then selected on solid media plates for their ability to utilize methane as a sole source of carbon and energy. The Sau3A1 insert that is present in those colonies having increased methane utilization relative to a control organism is sequenced. The coding sequence(s) found in the insert can be codon optimized for *Synechocystis* and their effect on methane utilization determined. Any such coding sequences that confer increased methane utilization can then be introduced and expressed in a *Synechocystis* strain containing coding sequences for MMO polypeptides. MMO activity in the resulting strain is measured by functional assays as described previously, as well as by ability of the engineered strain to grow on methane as a sole source of energy and carbon.

Example 3

Expression of Methanol Dehydrogenase

Conversion of methanol into formaldehyde in a phototrophic microorganism can be accomplished by the expression of NAD-dependent MDH or class I ADH from humans. NAD-dependent MDHs do not require a specialized cofactor. Alternatively, MDHs from methanotrophs can be used.

However, methanotroph MDHs utilize a specialized cofactor PQQ, and the expression of PQQ-MDH polypeptides and regulation of PQQ-MDH activity involves about 10 genes. Suitable NAD-dependent MDHs include those from methylotrophic *Bacillus methanolicus*.

Coding sequences are codon-optimized, synthesized, and expressed in *Synechocystis* behind a strong constitutive promoter and enzymatic function of MDH in the recombinant *Synechocystis* is measured using crude extracts and/or intact cells as previously described. It may be useful to express additional polypeptides. For example, regulation of *Bacillus methanolicus* MDH activity involves an activator protein, and it may be desirable to introduce and express coding sequences for the activator protein from *Bacillus methanolicus* in *Synechocystis*. Similarly, class I ADH enzymes from human exist in homodimeric or heterodimeric form and each form has different kinetic properties for different alcohols. Coding sequences (ADH1A, ADH1B and ADH1C) encoding class I ADH polypeptides, either as homodimeric or heterodimeric forms, can be expressed in various combinations and thereby identify suitable enzyme systems for specific oxidation of methanol in *Synechocystis*.

Example 4

Formaldehyde Assimilation by Recombinant *Synechocystis*

Formaldehyde in an engineered *Synechocystis* strain can be assimilated into central metabolic pathways via enzymes of the ribulose monophosphate pathway. Sequences encoding suitable RuMP pathway polypeptides include: i) hps and phi genes from *Methylococcus capsulatus* Bath; ii) hps and phi genes from *Bacillus methanolicus*; and iii) hps and phi genes from *Pyrococcus horikoshii*. In the first two cases, each polypeptide is encoded by a separate sequence, whereas a single coding sequence encodes both polypeptides in the third case. These sequences can be codon-optimized, synthesized and expressed in *Synechocystis* behind a strong constitutive promoter. After suitable expression is established by real time polymerase chain reaction and LC-MS, enzymatic activity in the engineered *Synechocystis* strain is measured as previously described.

Example 5

Ribulose Bisphosphate and Ribulose Monophosphate Regeneration

*Synechocystis* contains a highly active reductive pentose phosphate pathway. It plays a central role in coupling light energy to $CO_2$ fixation by regenerating ribulose bisphosphate for carboxylation reaction and channeling the fixed carbon to central metabolic pathways. In order to establish efficient assimilation of formaldehyde and capture of $CO_2$ in the recombinant *Synechocystis*, regeneration of both ribulose monophosphate and ribulose bisphosphate is balanced by the reductive pentose phosphate pathway. This is achieved first by biochemical studies using a *Synechocystis* strain expressing hps and phi genes to determine if the assimilation of formaldehyde is limited by the availability of ribulose monophosphate. This is carried out by incubation of intact cells with different concentrations of ribulose monophosphate. If it is determined that the rate of formaldehyde assimilation is limited by the availability of ribulose monophosphate then a coding sequence for phosphoribulokinase, an enzyme that converts ribulose monophosphate into ribulose bisphosphate, can be introduced and expressed in *Synechocystis* to achieve balanced regeneration of ribulose monophosphate and ribulose bisphosphate. The level of expression from the phosphoribulokinase coding sequence can be controlled by the type of promoter used to drive transcription, e.g., using a weak promoter, or using a copper regulated promoter. In *Synechocystis*, suitable copper regulated promoters include those driving expression of plastocyanin and Cyt c553, two electron carriers that can carry electrons from the cytochrome bf complex to photosystem I.

Similarly, a suitable level of expression can be determined for other enzymes involved in the reductive pentose phosphate pathway, including transketolase, transaldolase, and sedoheptulose-1,7-bisphosphatase, in order to achieve balanced regeneration of ribulose monophosphate and ribulose bisphosphate. If it is determined that certain enzymes involved in regeneration of ribulose monophosphate are limiting in recombinant organism, then a functionally homologous polypeptide from another cyanobacterial strain can be introduced into and expressed to overcome that limitation.

Example 6

Production of n-Butanol from Metabolic Pathway Intermediates

Recombinant phototrophic microorganisms can be generated that convert intermediates of the central metabolic pathways into a useful product (e.g. butanol). For example, nucleic acids encoding enzymes involved in the conversion of acetyl-CoA into n-butanol can expressed in a recombinant *Synechocystis* microorganism. Sequences suitable for introduction and expression in *Synechocystis* include the atoB gene from *E. coli*; hbd, crt and adhE2 genes from *Clostridium acetobutylicum*; and the ter gene from *Treponema denticola*. These sequences are codon optimized, introduced into and overexpressed in *Synechocystis* in order to confer the capability of producing n-butanol from acetyl-CoA.

Example 7

Biosynthesis of n-Butanol from Methane

A phototrophic microorganism can be produced that includes recombinant genes encoding and expressing: pMMO and/or sMMO polypeptides; an NAD-dependent MDH polypeptide and/or a human class I ADH polypeptide; an HPS polypeptide; an PHI polypeptide; an acetyl-CoA acetyltransferase polypeptide; a 3-hydroxybutyryl-CoA dehydrogenase polypeptide; a crotonase polypeptide; an aldehyde/alcohol dehydrogenase polypeptide; and a trans-enoyl-CoA reductase polypeptide. For example, a *Synechocystis* microorganism can contain codon optimized sequences encoding: pMMO and/or sMMO polypeptides described above, an NAD-dependent MDH polypeptide or a human class I ADH1A, ADH1B and/or ADH1C polypeptide described above; an HPS polypeptide described above; an PHI polypeptide described above; an acetyl-CoA acetyltransferase polypeptide described above; a 3-hydroxybutyryl-CoA dehydrogenase polypeptide described above; a crotonase polypeptide described above; an aldehyde/alcohol dehydrogenase polypeptide described above; and a trans-enoyl-CoA reductase polypeptide described above.

In some embodiments, such a microorganism further includes genes encoding peptides of the methanobactin gene cluster and/or one or more of the following polypeptides: phosphoribulokinase; transketolase, transaldolase, and sedoheptulose-1,7-bisphosphatase. A *Synechocystis* strain containing such recombinant genes can convert methane into a useful product (e.g. n-butanol).

Example 8

Recombinant *Synechocystis* Strains Capable of Oxidizing Methanol

Genes coding for alcohol dehydrogenase were obtained from *Bacillus methanolicus* MGA3 (locus: MGA3_17392; GI:387585261) and *Homo sapiens* [ADH1A (P07327.2); ADH1B (P00325.2), and ADH1C (NP_000660.1)]. An additional gene that acts as activator to methanol dehydrogenase in *Bacillus methanolicus* MGA3 (EIJ83380.1) was also obtained. They were codon-optimized for *Synechocystis* and synthesized. Two restriction sites (NdeI and HpaI) were introduced in each gene to facilitate cloning and subsequent recombination in *Synechocystis*. These genes were cloned behind the psbA2 promoter using the NdeI and HpaI sites and then introduced into a neutral locus in *Synechocystis*. Such neutral loci in *Synechocystis* are known in art and combinations of these loci can be used for this purpose if desired. A chloramphenicol acetyltransferase gene was also introduced into *Synechocystis* for selection of the recombinant strain using chloramphenicol as the selection agent. Genes that confer resistance to kanamycin, gentamicin, spectinomycin, or other similar antibiotics to which *Synechocystis* is sensitive can also be used for selection of recombinant strains.

A total of eight different isogenic recombinant *Synechocystis* strains were generated (see Table 1). Since the functional form of alcohol dehydrogenase in *Homo sapiens* can be either a homodimer or a heterodimer, some of the recombinant *Synechocystis* strains have two adh genes. The presence of the desired alcohol dehydrogenase gene(s) was confirmed by polymerase chain reaction assay, and expression was confirmed by RT-PCR.

Alcohol dehydrogenase enzymatic activity in the recombinant *Synechocystis* was measured using crude extracts and/or intact cells. Crude extract was isolated by first treating the *Synechocystis* cells with lysozyme in a buffer containing 50 mM Tris, PH 8.0, 10% glycerol, 0.1% Triton X-100 and incubating at 37° C. for 30 min. The treated cells were harvested by centrifugation at 4000×g for 5 min at 4° C. and resuspended in a buffer containing 50 mM Tris, PH 8.0, 10% glycerol, 0.1% Triton X-100 and protease inhibitor cocktail (Sigma). Cells were lysed by sonication using a Misonix S3000 Sonicator (power setting: 3 for a 4-5 cycles with each cycle lasting for 20 seconds). The crude extracts was clarified by centrifugation at 12,000×g for 5 min at 4° C. and the clarified supernatant containing was used to measure methanol dehydrogenase activity at 340 nm following $NAD^+$ reduction in a reaction mixture containing 500 mM (~2%) methanol, 100 mM glycine-KOH buffer (pH 9.5), 5 mM $MgSO_4$, 5 mM 2-mercaptoethanol, 1 mM $NAD^+$ and 10 μl of extract. The methanol dehydrogenase activity observed in the recombinant *Synechocystis* extracts is shown in Table 1. The results indicate that methanol dehydrogenase activity was observed in all strains except for MGC0460. Extracts of many of the strains also exhibited activity with ethanol, propanol or butanol as the substrate.

TABLE 1

Recombinant *Synechocystis* containing alcohol dehydrogenase genes

| Strain Name | Gene | Specific Activity (nmol NADPH/min/mg protein) |
| --- | --- | --- |
| MGC0416 | MDH | 0.0042 |
| MGC0440 | MDH and ACT | 0.0021 |
| MGC0428 | ADH1A | 0.0075 |
| MGC0443 | ADH1B | 0.0034 |
| MGC0452 | ADH1C | 0.0047 |
| MGC0448 | ADH1A and ADH1B | 0.0028 |
| MGC0460 | ADH1A and ADH1C | 0.0000 |
| MGC0461 | ADH1B and ADH1C | 0.0039 |

The effect of dehydrogenase expression on growth of recombinant *Synechocystis* strains was determined by measuring the optical density at 730 nm of strains cultured at 30° C. under a 30 μE $m^{-2}$ $s^{-1}$ light regimen and ambient air on media containing din the presence of light and ambient air in media containing different concentrations of methanol. The medium contained 1.5 g/L $NaNO_3$, 0.04 g/L $K_2HPO_4$, 0.075 g/L $MgSO_4.7H_2O$, 0.036 g/L $CaCl_2.2H_2O$, 0.006 g/L Citric acid, 0.006 g/L Ferric ammonium citrate, 0.001 g/L EDTA (disodium salt), 0.02 g/L $Na_2CO_3$ and 1 ml/L trace metal mix. Trace metal mix contained 2.86 g/L $H_3BO_3$, 1.81 g/L, $MnCl_2.4H_2O$, 0.222 g/L $ZnSO_4.7H_2O$, 0.39 g/L $NaMoO_4.2H_2O$, 0.079 g/L $CuSO_4.5H_2O$ and 0.0494 g/L $Co(NO_3)_2.6H_2O$.

Results are shown in FIG. 1, and indicate that recombinant *Synechocystis* strains containing and expressing an MDH, or MDH and ACT, can grow on media containing up to 2% methanol, despite the likely accumulation in the media of formaldehyde, the product of the dehydrogenase activity.

Example 9

A Recombinant *Synechocystis* Strain Capable of Assimilating Formaldehyde

Genes coding for 3-Hexulose-6-phosphate synthase (HPS) were obtained from *Methylococcus capsulatus* Bath (locus: MCA3043; GI:53756598), *Bacillus methanolicus* MGA3 (locus: MGA3_15306; GI:387587408) and *Pyrococcus horikoshii* OT3 (locus: PH1938; GI:14591680); and phospho-3-hexuloisomerase (PHI) from *Methylococcus capsulatus* Bath (locus: MCA3044; GI:53756597), *Bacillus methanolicus* MGA3 (locus: MGA3_15301; GI:387587407) and *Pyrococcus horikoshii* (locus: PH1938; GI:14591680). They were codon-optimized for expression in *Synechocystis* and synthesized. Two restriction sites (NdeI and HpaI) were introduced in each gene to facilitate cloning and subsequent recombination in *Synechocystis*. These genes were cloned behind the psbA2 promoter using the NdeI and HpaI sites and then introduced into a neutral locus in *Synechocystis*. A chloramphenicol acetyltransferase gene was also introduced into *Synechocystis* for selection of the recombinant strain using chloramphenicol as the selection agent.

Three different isogenic recombinant *Synechocystis* strains are generated, one containing HPS and PHI sequences from *Methylococcus capsulatus* Bath, one containing HPS and PHI sequences from *Bacillus methanolicus*, and one containing HPS and PHI sequences from *Pyrococcus horikoshii* OT3. The presence of the desired HPS and PHI genes is confirmed by polymerase chain reaction assay, and expression is confirmed by RT-PCR.

Enzymatic activity in the recombinant *Synechocystis* strains was measured using crude extracts and/or intact cells. Crude extracts were prepared as described in Example 8. HPS and PHI activities were measured by following NADP reduction at 340 nm in a 1 ml reaction mixture containing 50 mM potassium phosphate buffer pH 7.0, 5 mM magnesium chloride, 1 unit each of glucose-6-phosphate dehydrogenase (Sigma) and glucose-6-phosphate isomerase (Sigma), 0.4 mM NADP, 2.5 units of phosphoriboisomerase (Sigma), and 100 μl extract. After temperature equilibration to 30° C., 5 mM ribose-5-phosphate was added. After 1 min of further preincubation, the reaction was started by the addition of 5 mM formaldehyde. The specific activity of the *Methylococcus* HPS and PHI enzymes in *Synechocystis* crude extracts was 1086 nmol NADPH/min/mg protein. The results also indicated that expression of the HPS and PHI genes from *Methylococcus capsulatus* Bath conferred more formaldehyde assimilation activity on *Synechocystis* crude extracts than did the genes from *Pyrococcus* or *Bacillus*.

The effect of HPS and PHI expression on growth of wild type and recombinant *Synechocystis* strains was determined by measuring the growth of the MSI strain under a a 30 μE $m^{-2}$ $s^{-1}$ light regimen and in the presence of ambient air on media containing different concentrations of formaldehyde. The results are shown in Table 2, and indicate that wild type growth is inhibited at 5 mM formaldehyde whereas a *Synechocystis* strain expressing *Methylococcus* HPS and PHI can grow at concentrations up to 15 mM formaldehyde. The results in Table 2 also indicate that the rate of growth of recombinant *Synechocystis* cells in media containing 5 to 15 mM formaldehyde is about 88% to about 100% of the rate observed for recombinant *Synechocystis* cells grown in media having no added formaldehyde.

TABLE 2

Growth of wild type and recombinant *Synechocystis* strains in the presence of different concentrations of formaldehyde.

| Formaldehyde concentration (mM) | OD730 after 6 days Wild Type cells | OD730 after 6 days Recombinant *Synechocystis* cells |
| --- | --- | --- |
| 0 | 1.316 | 1.292 |
| 5 | 0.728 | 1.244 |
| 10 | 0.064 | 1.136 |
| 15 | 0.06 | 1.288 |
| 20 | 0.096 | 0.032 |

Figure 2:
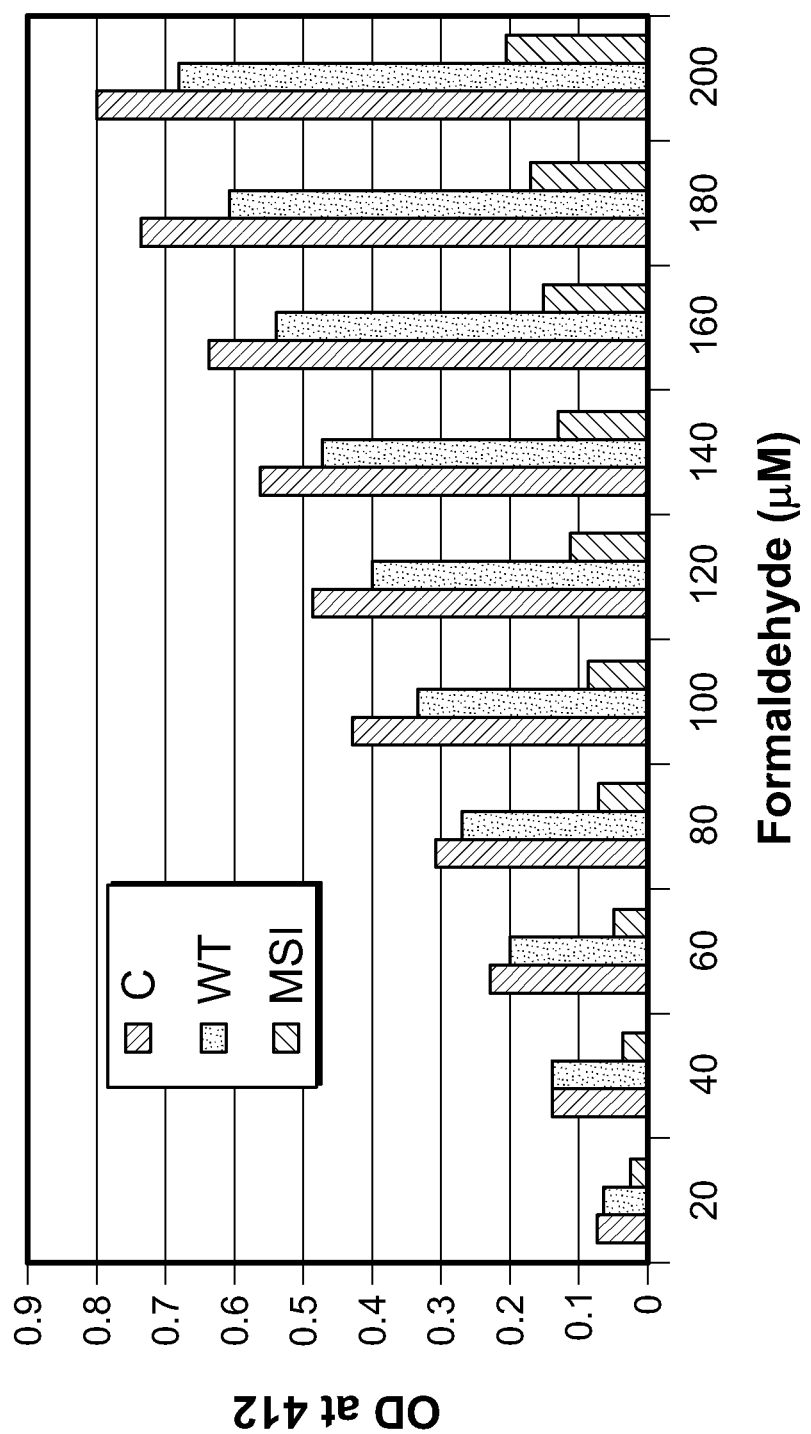
FIG. 2 is a bar graph showing the formaldehyde concentration (as measured by absorbance at 412 nm) in supernatants of *Synechocystis* cultures after 1 day of growth at 30° C. in media containing formaldehyde. C=no cells; WT=wild type *Synechocystis* cells; MSI=cells of a recombinant *Synechocystis* strain expressing *Methylococcus capsulatus* HPS and PHI genes.

The amount of formaldehyde present in the culture supernatant of a *Synechocystis* strain expressing HPS and PHI was determined after growth for 1 day at 30° C. in media containing from various concentrations of formaldehyde, from 20 μM to 200 μM. The amount of formaldehyde in the supernatant was measured using a colorimetric assay based on the Hantzsch reaction. Nash, *Biochem. J.* 55: 416-421 (1953). The results are shown in FIG. 2, and indicate that formaldehyde in culture supernatants from *Synechocystis* cells expressing HPS and PHI is depleted to a much greater extent than in the supernatant from wild type control *Synechocystis* cells that lack these two genes. The amount of formaldehyde in supernatant from *Synechocystis* cells expressing HPS and PHI is about 4-fold less than the amount in supernatant from the isogenic wild type *Synechocystis* cells.

What is claimed is:

1. A recombinant *Synechocystis* sp. PCC 6803, comprising:
   (i) a gene encoding a soluble methane monooxygenase (sMMO);
   (ii) a gene encoding a methanol dehydrogenase (MDH);
   (iii) a gene encoding a hexulose-6-phosphate synthase (HPS); and
   (iv) a gene encoding a 6-phosphate-3-hexuloisomerase (PHI).

2. The recombinant *Synechocystis* sp. PCC 6803 of claim 1, wherein the gene encoding the sMMO is a group of genes that together encode: an MmoX polypeptide, an MmoY polypeptide, an MmoB polypeptide, an MmoZ polypeptide, an MmoD polypeptide, and an MmoC polypeptide.

3. The recombinant *Synechocystis* sp. PCC 6803 of claim 1, wherein the gene encoding the MDH encodes a polypeptide having the amino acid sequence of an NAD-dependent MDH from methylotrophic *Bacillus methanolicus*.

4. The recombinant *Synechocystis* sp. PCC 6803 of claim 1, wherein the gene encoding the HPS encodes a polypeptide having the amino acid sequence of a HPS from *Methylococcus capsulatus*, *Bacillus methanolicus*, or *Pyrococcus horikoshii*.

5. The recombinant *Synechocystis* sp. PCC 6803 of claim 1, wherein the gene encoding the PHI encodes a polypeptide having the amino acid sequence of a PHI from *Methylococcus capsulatus*, *Bacillus methanolicus*, or *Pyrococcus horikoshii*.

6. The recombinant *Synechocystis* sp. PCC 6803 of claim 2, wherein:
   the MmoX polypeptide, the MmoY polypeptide, the MmoB polypeptide, the MmoZ polypeptide, and the MmoC polypeptide are from *Methylococcus capsulatus*;
   the MDH is a NAD-dependent MDH from methylotrophic *Bacillus methanolicus*;
   the HPS is a HPS from *Methylococcus capsulatus*; and
   the PHI is a PHI from *Methylococcus capsulatus*.

7. The recombinant *Synechocystis* sp. PCC 6803 of claim 1, wherein the *Synechocystis* sp. PCC 6803 is capable of growth in media containing up to 2% (v/v) methanol, or capable of growth in media containing up to 15 mM formaldehyde.

8. The recombinant *Synechocystis* sp. PCC 6803 of claim 1, wherein expression of the genes of (i) to (iv) in the *Synechocystis* sp. PCC 6803 results in the oxidation of an alkane and the production of a product selected from the group consisting of: an alcohol, an amino acid, a dicarboxylic acid, a fatty acid, and an intermediate of a central metabolic pathway, when the *Synechocystis* sp. PCC 6803 is cultured in the presence of light and $O_2$ in a medium comprising the alkane.

* * * * *

SEQUENCE LISTING

```
<160> NUMBER OF SEQ ID NOS: 95

<210> SEQ ID NO 1
<211> LENGTH: 246
<212> TYPE: PRT
<213> ORGANISM: Methylococcus capsulatus

<400> SEQUENCE: 1

Met Ser Ala Ala Gln Ser Ala Val Arg Ser His Ala Glu Ala Val Gln
1               5                   10                  15

Val Ser Arg Thr Ile Asp Trp Met Ala Leu Phe Val Val Phe Phe Val
            20                  25                  30

Ile Val Gly Ser Tyr His Ile His Ala Met Leu Thr Met Gly Asp Trp
        35                  40                  45

Asp Phe Trp Ser Asp Trp Lys Asp Arg Arg Leu Trp Val Thr Val Thr
    50                  55                  60

Pro Ile Val Leu Val Thr Phe Pro Ala Ala Val Gln Ser Tyr Leu Trp
65                  70                  75                  80

Glu Arg Tyr Arg Leu Pro Trp Gly Ala Thr Val Cys Val Leu Gly Leu
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Ala Ser Leu Val Pro Gly Ala
        115                 120                 125

Ile Ile Leu Asp Thr Val Leu Met Leu Ser Gly Ser Tyr Leu Phe Thr
    130                 135                 140

Ala Ile Val Gly Ala Met Gly Trp Gly Leu Ile Phe Tyr Pro Gly Asn
145                 150                 155                 160
```

```
Trp Pro Ile Ile Ala Pro Leu His Val Pro Val Glu Tyr Asn Gly Met
                165                 170                 175

Leu Met Ser Ile Ala Asp Ile Gln Gly Tyr Asn Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Phe Ser Ala Phe Met Ser
    210                 215                 220

Ile Leu Ile Tyr Phe Met Trp His Phe Ile Gly Arg Trp Phe Ser Asn
225                 230                 235                 240

Glu Arg Phe Leu Gln Ser
                245

<210> SEQ ID NO 2
<211> LENGTH: 252
<212> TYPE: PRT
<213> ORGANISM: Methylosinus trichosporium

<400> SEQUENCE: 2

Met Phe Thr Ser Lys Ser Gly Gly Ala Ile Gly Pro Phe His Ser Val
1               5                   10                  15

Ala Glu Ala Ala Gly Cys Val Lys Thr Thr Asp Trp Met Phe Leu Thr
                20                  25                  30

Leu Leu Phe Leu Ala Val Leu Gly Gly Tyr His Ile His Phe Met Leu
            35                  40                  45

Thr Ala Gly Asp Trp Asp Phe Trp Val Asp Trp Lys Asp Arg Arg Met
        50                  55                  60

Trp Pro Thr Val Val Pro Ile Leu Gly Val Thr Phe Ala Ala Ala Ala
65                  70                  75                  80

Gln Ala Phe Phe Trp Glu Asn Phe Lys Leu Pro Phe Gly Ala Thr Phe
                85                  90                  95

Ala Val Ser Gly Leu Leu Ile Gly Glu Trp Ile Asn Arg Tyr Cys Asn
                100                 105                 110

Phe Trp Gly Trp Thr Tyr Phe Pro Ile Ser Leu Val Phe Pro Ser Ala
            115                 120                 125

Leu Val Val Pro Ala Leu Trp Leu Asp Ile Ile Met Leu Leu Ser Gly
        130                 135                 140

Ser Tyr Val Ile Thr Ala Val Val Gly Ser Leu Gly Trp Gly Leu Leu
145                 150                 155                 160

Phe Tyr Pro Asn Asn Trp Pro Ala Ile Ala Ala Leu His Gln Ala Thr
                165                 170                 175

Glu Gln His Gly Gln Leu Met Ser Leu Ala Asp Leu Val Gly Phe His
            180                 185                 190

Phe Val Arg Thr Ser Met Pro Glu Tyr Ile Arg Met Val Glu Arg Gly
        195                 200                 205

Thr Leu Arg Thr Phe Gly Lys Glu Val Val Pro Val Ala Ala Phe Phe
    210                 215                 220

Ser Gly Phe Val Ser Met Met Val Tyr Phe Leu Trp Trp Phe Val Gly
225                 230                 235                 240

Lys Trp Tyr Ser Thr Thr Lys Val Ile Gln Lys Ile
                245                 250

<210> SEQ ID NO 3
<211> LENGTH: 247
<212> TYPE: PRT
<213> ORGANISM: Methylohalobius crimeensis
```

<400> SEQUENCE: 3

```
Met Ser Thr Thr Thr Ser Ala Val Arg Ser His Ala Glu Ala Val Gln
1               5                   10                  15

Val Ser Arg Thr Val Asp Tyr Leu Gly Leu Phe Ile Leu Phe Phe Val
            20                  25                  30

Leu Thr Gly Ser Tyr His Ile His Gly Met Leu Thr Met Gly Asp Trp
        35                  40                  45

Asp Phe Trp Ser Asp Trp Lys Asp Arg Arg Leu Trp Val Thr Val Tyr
50                  55                  60

Pro Ile Val Met Ile Thr Phe Pro Ala Ala Val Gln Ala Val Ile Trp
65                  70                  75                  80

Glu Arg Leu Arg Leu Pro Phe Gly Ala Thr Ile Ser Ile Leu Gly Ile
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Thr Ala Ala Val His Met Ala
        115                 120                 125

Ile Phe Leu Asp Val Val Leu Met Leu Ser Ser Ser Phe Leu Phe Thr
130                 135                 140

Ala Val Val Gly Gly Leu Gly Trp Gly Leu Leu Met Tyr Pro Gly Asn
145                 150                 155                 160

Trp Pro Val Ile Ala Pro Leu His Val Pro Val Glu Tyr Asn Gly Met
                165                 170                 175

Leu Met Ser Val Ala Asp Ile Gln Gly Tyr His Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Phe Ser Gly Phe Met Ser
210                 215                 220

Ile Leu Ile Tyr Phe Met Trp His Phe Val Gly Arg Trp Phe Gly Thr
225                 230                 235                 240

Val Lys Phe Val Lys Lys Thr
                245
```

<210> SEQ ID NO 4
<211> LENGTH: 247
<212> TYPE: PRT
<213> ORGANISM: Methylomicrobium alcaliphilum

<400> SEQUENCE: 4

```
Met Ser Ala Ser Gln Ser Ala Val Arg Ser Arg Ala Glu Ala Val Lys
1               5                   10                  15

Val Ser Arg Thr Phe Asp Tyr Met Ile Leu Phe Thr Val Phe Phe Val
            20                  25                  30

Val Leu Gly Gly Tyr His Ile His Tyr Met Leu Thr Gly Gly Asp Trp
        35                  40                  45

Asp Phe Trp Thr Asp Trp Lys Asp Arg Arg Leu Trp Val Thr Val Ala
50                  55                  60

Pro Ile Val Ser Ile Thr Phe Pro Ala Ala Val Gln Ala Val Leu Trp
65                  70                  75                  80

Trp Arg Tyr Arg Ile Ala Trp Gly Ala Thr Leu Cys Val Leu Gly Leu
                85                  90                  95

Leu Leu Gly Glu Trp Ile Asn Arg Tyr Phe Asn Phe Trp Gly Trp Thr
            100                 105                 110
```

```
Tyr Phe Pro Val Asn Phe Val Phe Pro Ser Asn Leu Met Pro Gly Ala
            115                 120                 125

Ile Val Leu Asp Val Ile Leu Met Leu Ser Asn Ser Met Thr Leu Thr
130                 135                 140

Ala Val Val Gly Gly Leu Ala Trp Gly Leu Leu Phe Tyr Pro Gly Asn
145                 150                 155                 160

Trp Pro Ile Ile Ala Pro Leu His Val Pro Val Glu Tyr Asn Gly Met
            165                 170                 175

Met Met Thr Leu Ala Asp Leu Gln Gly Tyr His Tyr Val Arg Thr Gly
            180                 185                 190

Thr Pro Glu Tyr Ile Arg Met Val Glu Lys Gly Thr Leu Arg Thr Phe
            195                 200                 205

Gly Lys Asp Val Ala Pro Val Ser Ala Phe Phe Ser Gly Phe Val Ser
            210                 215                 220

Ile Leu Ile Tyr Phe Leu Trp His Phe Phe Gly Ser Trp Phe Gly Ser
225                 230                 235                 240

Glu Lys Phe Val Gln Ala Ala
            245

<210> SEQ ID NO 5
<211> LENGTH: 252
<212> TYPE: PRT
<213> ORGANISM: Methylocystis sp.

<400> SEQUENCE: 5

Met Ser Gln Ser Lys Ser Gly Gly Ala Val Gly Pro Phe Asn Ser Val
1               5                   10                  15

Ala Glu Ala Ala Gly Cys Val Gln Thr Val Asp Trp Met Leu Leu Val
            20                  25                  30

Leu Leu Phe Phe Ala Val Leu Gly Gly Tyr His Val His Phe Met Leu
            35                  40                  45

Thr Ala Gly Asp Trp Asp Phe Trp Val Asp Trp Lys Asp Arg Arg Met
    50                  55                  60

Trp Pro Thr Val Val Pro Ile Leu Gly Val Thr Phe Cys Ala Ala Ala
65                  70                  75                  80

Gln Ala Phe Trp Trp Val Asn Phe Arg Leu Pro Phe Gly Ala Val Phe
            85                  90                  95

Ala Ala Leu Gly Leu Leu Ile Gly Glu Trp Ile Asn Arg Tyr Val Asn
            100                 105                 110

Phe Trp Gly Trp Thr Tyr Phe Pro Ile Ser Leu Val Phe Pro Ser Ala
            115                 120                 125

Leu Ile Val Pro Ala Ile Trp Leu Asp Val Ile Leu Leu Leu Ser Gly
130                 135                 140

Ser Tyr Val Ile Thr Ala Ile Val Gly Ser Leu Gly Trp Gly Leu Leu
145                 150                 155                 160

Phe Tyr Pro Asn Asn Trp Pro Ala Ile Ala Phe His Gln Ala Thr
            165                 170                 175

Glu Gln His Gly Gln Leu Met Thr Leu Ala Asp Leu Ile Gly Phe His
            180                 185                 190

Phe Val Arg Thr Ser Met Pro Glu Tyr Ile Arg Met Val Glu Arg Gly
            195                 200                 205

Thr Leu Arg Thr Phe Gly Lys Asp Val Val Pro Val Ala Ala Phe Phe
            210                 215                 220

Ser Gly Phe Val Ser Met Met Val Tyr Phe Leu Trp Trp Phe Met Gly
```

```
                225                 230                 235                 240
Arg Trp Tyr Ser Thr Thr Lys Ile Ile Asp Thr Ile
                    245                 250

<210> SEQ ID NO 6
<211> LENGTH: 249
<212> TYPE: PRT
<213> ORGANISM: Methylococcaceae bacterium

<400> SEQUENCE: 6

Met Ser Ala Ser Gln Ser Ala Val Arg Ser Arg Ala Glu Ala Val Ala
1               5                   10                  15

Val Ser Arg Thr Phe Asp Trp Met Ile Leu Trp Thr Leu Phe Phe Val
                20                  25                  30

Ile Leu Gly Gly Tyr His Ile His Tyr Met Leu Thr Gly Gly Asp Trp
            35                  40                  45

Asp Phe Trp Ala Asp Trp Lys Asp Arg Arg Leu Trp Val Thr Val Ala
        50                  55                  60

Pro Ile Val Ser Ile Thr Phe Pro Ala Ala Val Gln Ala Cys Leu Trp
65                  70                  75                  80

Tyr Arg Tyr Arg Leu Pro Val Gly Ala Thr Ile Cys Val Leu Gly Leu
                85                  90                  95

Leu Leu Gly Glu Trp Val Asn Arg Tyr Leu Asn Phe Trp Gly Trp Thr
            100                 105                 110

Tyr Phe Pro Val Asn Phe Cys Phe Pro Ser Asn Leu Met Pro Gly Ala
        115                 120                 125

Ile Leu Leu Asp Val Ile Leu Met Met Gly Gly Ser Met Thr Leu Thr
    130                 135                 140

Ala Val Val Gly Gly Leu Ala Trp Gly Leu Val Phe Tyr Pro Gly Asn
145                 150                 155                 160

Trp Pro Ile Ile Ala Pro Leu His Val Pro Val Glu Tyr Asn Gly Met
                165                 170                 175

Met Phe Thr Leu Ala Asp Leu Gln Gly Tyr His Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Phe Ser Gly Phe Val Ser
    210                 215                 220

Ile Ile Ile Tyr Phe Leu Trp Phe Phe Gly Lys Trp Phe Ser Lys
225                 230                 235                 240

Thr Asp Phe Ile Ser Gly Glu Asp Val
                245

<210> SEQ ID NO 7
<211> LENGTH: 249
<212> TYPE: PRT
<213> ORGANISM: Methylomarinum vadi

<400> SEQUENCE: 7

Met Ser Ala Ser Gln Ser Ala Val Arg Ser Arg Ala Glu Ala Val Gln
1               5                   10                  15

Val Ser Arg Thr Phe Asp Trp Met Ile Leu Phe Thr Leu Phe Thr Ala
                20                  25                  30

Val Leu Gly Gly Tyr His Ile His Tyr Met Leu Thr Gly Gly Asp Trp
            35                  40                  45

Asp Phe Trp Ser Asp Trp Lys Asp Arg Arg Leu Trp Val Thr Val Ala
```

```
                      50                  55                  60
Pro Ile Val Ser Ile Thr Phe Pro Ala Ala Val Gln Ala Cys Leu Trp
 65                  70                  75                  80

Trp Arg Tyr Arg Leu Pro Ile Gly Ala Thr Ile Ser Val Leu Ala Leu
                 85                  90                  95

Leu Leu Gly Glu Trp Ile Asn Arg Tyr Met Asn Phe Trp Gly Trp Thr
                100                 105                 110

Tyr Phe Pro Val Asn Phe Val Phe Pro Ser Asn Leu Val Pro Gly Ala
            115                 120                 125

Ile Val Leu Asp Val Val Leu Met Leu Gly Gly Ser Met Thr Leu Thr
            130                 135                 140

Ala Val Val Gly Gly Met Ala Tyr Gly Leu Leu Phe Tyr Pro Gly Asn
145                 150                 155                 160

Trp Pro Ile Ile Ala Pro Leu His Val Pro Val Glu Tyr Asn Gly Met
                165                 170                 175

Met Met Thr Leu Ala Asp Leu Gln Gly Tyr His Tyr Val Arg Thr Gly
                180                 185                 190

Thr Pro Glu Tyr Ile Arg Met Val Glu Lys Gly Thr Leu Arg Thr Phe
                195                 200                 205

Gly Lys Asp Val Ala Pro Val Ser Ala Phe Phe Ser Ala Phe Val Ser
            210                 215                 220

Ile Ile Ile Tyr Phe Leu Trp His Phe Gly Arg Trp Phe Ala Lys
225                 230                 235                 240

Thr Asp Phe Ile Ala Asp Asp Ala Ser
                245

<210> SEQ ID NO 8
<211> LENGTH: 419
<212> TYPE: PRT
<213> ORGANISM: Methylocystis sp.

<400> SEQUENCE: 8

Met Lys Lys Leu Val Lys Leu Ala Ala Phe Gly Ala Ala Ala Ala Val
  1               5                  10                  15

Ala Ala Thr Leu Gly Ala Ile Ala Pro Ala Ser Ala His Gly Glu Lys
                 20                  25                  30

Ser Gln Gln Ala Phe Leu Arg Met Arg Thr Leu Asn Trp Tyr Asp Val
             35                  40                  45

Gln Trp Ser Lys Thr Thr Val Asn Val Asn Glu Glu Met Ile Leu Ser
 50                  55                  60

Gly Lys Val His Val Phe Ser Ala Trp Pro Gln Ala Val Ala Asn Pro
 65                  70                  75                  80

Arg Val Ser Phe Leu Asn Ala Gly Glu Pro Gly Pro Val Leu Val Arg
                 85                  90                  95

Thr Ala Gln Phe Ile Gly Glu Gln Phe Ala Pro Arg Ser Val Ser Leu
                100                 105                 110

Glu Ile Gly Lys Asp Tyr Ala Phe Ser Ile Asn Leu Arg Gly Arg Arg
            115                 120                 125

Ala Gly Arg Trp His Val His Ala Gln Ile Asn Val Glu Gly Gly Gly
            130                 135                 140

Pro Ile Ile Gly Pro Gly Gln Trp Ile Glu Ile Lys Gly Asp Met Lys
145                 150                 155                 160

Asp Phe Thr Asp Pro Val Thr Leu Leu Asp Gly Ser Thr Val Asp Leu
                165                 170                 175
```

```
Glu Asn Tyr Gly Ile Ser Arg Ile Tyr Ala Trp His Leu Pro Trp Leu
                180                 185                 190
Ala Val Gly Ala Ala Trp Ile Leu Phe Trp Phe Ile Arg Lys Gly Ile
            195                 200                 205
Ile Ala Ser Tyr Val Arg Val Ala Glu Gly Arg Pro Asp Asp Val Ile
        210                 215                 220
Gly Asp Asp Arg Arg Ile Gly Ala Ile Val Leu Ala Leu Thr Ile
225                 230                 235                 240
Leu Ala Thr Ile Val Gly Tyr Ala Val Thr Asn Ser Thr Phe Pro Arg
                245                 250                 255
Thr Ile Pro Leu Gln Ala Gly Leu Gln Lys Pro Leu Thr Pro Ile Glu
            260                 265                 270
Thr Glu Gly Thr Val Gly Val Gly Lys Glu Gln Val Thr Thr Glu Leu
        275                 280                 285
Asn Gly Gly Val Tyr Lys Val Pro Gly Arg Glu Leu Thr Ile Asn Val
290                 295                 300
Lys Val Lys Asn Gly Thr Ser Gln Pro Val Arg Leu Gly Glu Tyr Thr
305                 310                 315                 320
Ala Ala Gly Leu Arg Phe Leu Asn Pro Thr Val Phe Thr Gln Lys Pro
                325                 330                 335
Asp Phe Pro Asp Tyr Leu Leu Ala Asp Arg Gly Leu Ser Asn Asp Asp
            340                 345                 350
Val Ile Ala Pro Gly Glu Ser Lys Glu Ile Val Val Lys Ile Gln Asp
        355                 360                 365
Ala Arg Trp Asp Ile Glu Arg Leu Ser Asp Leu Ala Tyr Asp Thr Asp
370                 375                 380
Ser Gln Val Gly Gly Leu Leu Phe Phe Phe Thr Pro Asp Gly Lys Arg
385                 390                 395                 400
Phe Ala Ala Glu Ile Gly Gly Pro Val Ile Pro Lys Phe Val Ala Gly
                405                 410                 415
Asp Met Pro

<210> SEQ ID NO 9
<211> LENGTH: 431
<212> TYPE: PRT
<213> ORGANISM: Methylosinus trichosporium

<400> SEQUENCE: 9

Met Lys Ala Leu Glu Arg Met Ala Glu Leu Ala Thr Gly Arg Val Gly
1               5                   10                  15
Lys Leu Leu Gly Leu Ser Val Ala Ala Val Ala Ala Thr Ala Ala
            20                  25                  30
Ser Val Ala Pro Ala Glu Ala His Gly Glu Lys Ser Gln Gln Ala Phe
        35                  40                  45
Leu Arg Met Arg Thr Leu Asn Trp Tyr Asp Val Lys Trp Ser Lys Thr
50                  55                  60
Ser Leu Asn Val Asn Glu Ser Met Val Leu Ser Gly Lys Val His Val
65                  70                  75                  80
Phe Ser Ala Trp Pro Gln Ala Val Ala Asn Pro Lys Ser Ser Phe Leu
                85                  90                  95
Asn Ala Gly Glu Pro Gly Pro Val Leu Val Arg Thr Ala Gln Phe Ile
            100                 105                 110
Gly Glu Gln Phe Ala Pro Arg Ser Val Ser Leu Glu Val Gly Lys Asp
        115                 120                 125
```

```
Tyr Ala Phe Ser Ile Asp Leu Lys Ala Arg Arg Ala Gly Arg Trp His
                130                 135                 140

Val His Ala Gln Ile Asn Val Glu Gly Gly Pro Ile Ile Gly Pro
145                 150                 155                 160

Gly Gln Trp Ile Glu Ile Lys Gly Asp Met Ala Asp Phe Lys Asp Pro
                165                 170                 175

Val Thr Leu Leu Asp Gly Thr Thr Val Asp Leu Glu Thr Tyr Gly Ile
                180                 185                 190

Asp Arg Ile Tyr Ala Trp His Phe Pro Trp Met Ile Ala Ala Ala
                195                 200                 205

Trp Ile Leu Tyr Trp Phe Phe Lys Lys Gly Ile Ile Ala Ser Tyr Leu
210                 215                 220

Arg Ile Ser Glu Gly Lys Asp Glu Glu Gln Ile Gly Asp Asp Arg
225                 230                 235                 240

Arg Val Gly Ala Ile Val Leu Ala Val Thr Ile Leu Ala Thr Ile Ile
                245                 250                 255

Gly Tyr Ala Val Thr Asn Ser Thr Phe Pro Arg Thr Ile Pro Leu Gln
                260                 265                 270

Ala Gly Leu Gln Lys Pro Leu Thr Pro Ile Ile Glu Glu Gly Thr Ala
                275                 280                 285

Gly Val Gly Pro His Val Val Thr Ala Glu Leu Lys Gly Gly Val Tyr
                290                 295                 300

Lys Val Pro Gly Arg Glu Leu Thr Ile Gln Val Lys Val Thr Asn Lys
305                 310                 315                 320

Thr Asp Glu Pro Leu Lys Leu Gly Glu Tyr Thr Ala Ala Gly Leu Arg
                325                 330                 335

Phe Leu Asn Pro Asp Val Phe Thr Thr Lys Pro Glu Phe Pro Asp Tyr
                340                 345                 350

Leu Leu Ala Asp Arg Gly Leu Ser Thr Asp Pro Thr Pro Leu Ala Pro
                355                 360                 365

Gly Glu Thr Lys Thr Ile Glu Val Lys Val Gln Asp Ala Arg Trp Asp
                370                 375                 380

Ile Glu Arg Leu Ser Asp Leu Ala Tyr Asp Thr Asp Ser Gln Ile Gly
385                 390                 395                 400

Gly Leu Leu Met Phe Phe Ser Pro Ser Gly Lys Arg Tyr Ala Thr Glu
                405                 410                 415

Ile Gly Gly Pro Val Ile Pro Lys Phe Val Ala Gly Asp Met Pro
                420                 425                 430

<210> SEQ ID NO 10
<211> LENGTH: 427
<212> TYPE: PRT
<213> ORGANISM: Uncultured bacterium

<400> SEQUENCE: 10

Met Thr Thr Thr Met Phe Ser Ser Leu Ala Arg Gln Thr Gly Arg Leu
1               5                   10                  15

Trp Ala Leu Val Leu Ala Ala Ala Leu Ala Val Thr Met Ala Ala Ile
                20                  25                  30

Gly Pro Ala Asp Ala His Gly Glu Lys Ser Gln Ala Ala Phe Leu Arg
                35                  40                  45

Met Arg Thr Leu Asn Trp Tyr Asp Val Val Trp Ser Lys Thr Asn Val
                50                  55                  60

Ala Val Asn Glu Glu Tyr Glu Ile Thr Gly Lys Leu His Ile Met Asn
65                  70                  75                  80
```

```
Ser Trp Pro Ala Ala Ile Lys Val Pro Asp Gln Cys Phe Leu Asn Thr
                85                  90                  95

Gly Gln Pro Gly Ala Met Ala Ala Arg Leu Gly Val Trp Val Gly Ala
            100                 105                 110

Pro Gly Gln Met Gln Phe Thr Pro Arg Ser Met Arg Leu Asp Val Gly
        115                 120                 125

Lys Thr Tyr Ala Phe Arg Ile Leu Leu Lys Gly Arg Arg Pro Gly His
    130                 135                 140

Trp His Thr His Val Gln Leu Ser Val Met Thr Gly Gly Pro Ile Pro
145                 150                 155                 160

Gly Pro Gly Gln Tyr Ile Asp Ile Lys Gly Asn Phe Ser Asp Phe Val
                165                 170                 175

Asp Asp Val Lys Leu Leu Asn Gly Thr Thr Val Asp Ile Glu Thr Tyr
            180                 185                 190

Gly Ile Gly Lys Ile Tyr Met Trp His Leu Phe Trp Ile Val Val Gly
        195                 200                 205

Gly Trp Trp Ile Leu Tyr Trp Phe Gly Lys Arg Gly Phe Ile Gly Arg
    210                 215                 220

Phe Ala Trp Val Ala Ser Gly Lys Ala Glu Glu Val Ile Thr Pro Gln
225                 230                 235                 240

Glu Arg Val Val Gly Ala Ile Thr Leu Leu Ala Val Leu Leu Val Val
                245                 250                 255

Ile Ile Phe Tyr Ala Ile Thr Val Ser Gly Asn Pro Asn Thr Ile Pro
            260                 265                 270

Leu Gln Ala Gly Asp Phe Arg Asn Ile Thr Ala Leu Glu Asn Glu Val
        275                 280                 285

Asp Ser Gly Pro Ile Thr Ile Lys Tyr Leu Asn Gly Thr Tyr Lys Val
    290                 295                 300

Pro Gly Arg Glu Leu Val Ala Asn Phe Lys Ile Thr Asn Asn Gly Lys
305                 310                 315                 320

Glu Pro Leu Arg Ile Gly Glu Phe Asn Thr Ala Gly Leu Arg Phe Leu
                325                 330                 335

Asn Pro Asp Val Tyr Thr Ala Lys Val Val Tyr Pro Asp Tyr Leu Leu
            340                 345                 350

Ala Glu Arg Gly Leu Ser Leu Asn Asp Asn Ser Pro Ile Ala Pro Gly
        355                 360                 365

Glu Thr Arg Asp Val Ala Val Thr Val Gln Asp Ala Arg Trp Asp Thr
    370                 375                 380

Glu Arg Leu Ser Gly Leu Ala Tyr Asp Val Asp Ser Ser Phe Ala Gly
385                 390                 395                 400

Val Leu Phe Phe Phe Ser Pro Ser Gly Ala Arg Tyr Pro Met Glu Val
                405                 410                 415

Gly Gly Pro Val Ile Pro Thr Phe Met Pro Val
            420                 425

<210> SEQ ID NO 11
<211> LENGTH: 415
<212> TYPE: PRT
<213> ORGANISM: Methylacidiphilum infernorum

<400> SEQUENCE: 11

Met Lys Asn Asn Asn Ile Lys Gly Leu Phe Leu Thr Phe Ile Ser Ile
1               5                   10                  15

Ile Tyr Gly Val Leu Met Leu Ile Asn Ala Pro Pro Val Tyr Ser Ser
```

```
            20                  25                  30
Gly Ile Gly Glu Arg Ala Gln Glu Ala Ile Leu Arg Met Arg Thr Ala
        35                  40                  45
Gln Phe Tyr Asp Val Arg Phe Ser Thr Asn His Leu Lys Val Gly Glu
 50                  55                  60
Asp Leu Val Val Thr Gly Lys Val Met Ile Leu Pro Ile Trp Pro His
 65                  70                  75                  80
Glu Leu Gly Phe Ser Gly Ile Gly Tyr Ile Asn Phe Phe Glu Pro Gly
                 85                  90                  95
Pro Arg Leu Val Arg Lys Glu Thr Val Val Asn Gly Gln Pro Leu Phe
                100                 105                 110
Ser Ser Met Ile Ile Lys Leu Gly Asp Asn Tyr Glu Phe Lys Glu Val
                115                 120                 125
Leu Thr Ala Arg Gln Pro Gly Asn Trp Pro Val Gly Val Thr Met Asn
                130                 135                 140
Ile Lys Asp Ile Gly Pro Ile Val Gly Pro Ser Ile Lys Val Ala Ile
145                 150                 155                 160
Asp Pro Ser Asn Ser Pro Phe Thr Tyr Ile Ile Lys Thr Leu Thr Gly
                165                 170                 175
Gln Thr Val Asn Leu Glu Asn Tyr Gly Leu Ser Arg Ala Phe Gly Trp
                180                 185                 190
Ser Met Leu Trp Val Phe Leu Gly Ile Gly Trp Leu Tyr Tyr Trp Leu
                195                 200                 205
Ile Leu Lys Pro Thr Ala Pro Arg Leu Gly Leu Ala Tyr Leu Glu Lys
                210                 215                 220
Glu Glu Glu Leu Ile Thr Lys Lys Asp Thr Gln Phe Gly Leu Leu Phe
225                 230                 235                 240
Leu Ala Ile Val Val Ile Leu Val Phe Gly Gly Ala Phe Ile Thr Ser
                245                 250                 255
Lys Gln Phe Pro Ile Val Val Pro Leu Gln Lys Thr Phe Val Arg Ile
                260                 265                 270
Asp Pro Leu Ala Pro Glu Pro Ala Phe Val Glu Ala Lys Val Thr Lys
                275                 280                 285
Ala Thr Tyr Asn Val Gln Gln Arg Ser Leu Asp Phe Asp Leu Gln Val
                290                 295                 300
Thr Asn Lys Gly Thr Asp Lys Val Tyr Leu Lys Arg Phe Gln Thr Ala
305                 310                 315                 320
Asn Val Ala Phe Leu Asn Pro Ser Ala Pro Asn Asn Gln Trp Ala Ser
                325                 330                 335
Asp Ser Pro Glu Val Asn Gly Gly Glu Leu Gln Ile Thr Pro Ser Glu
                340                 345                 350
Pro Ile Leu Ala Gly Glu Thr Lys Thr Leu His Val Lys Ala Gln Gly
                355                 360                 365
Ser Ala Trp Glu Val Glu Arg Leu Ser Thr Ile Tyr Lys Glu Thr Ala
                370                 375                 380
Ser Arg Phe Gly Gly Leu Leu Phe Ser Asp Thr Glu Gly Arg Arg
385                 390                 395                 400
Asn Ile Ile Ala Ile Ala Asp Gln Phe Val Val Pro Val Phe Glu
                405                 410                 415

<210> SEQ ID NO 12
<211> LENGTH: 421
<212> TYPE: PRT
<213> ORGANISM: Methylocapsa acidiphila
```

<400> SEQUENCE: 12

```
Met Phe Ser Thr Leu Ala Gly His Ala Lys Arg Gln Ala Gly Arg Leu
1               5                   10                  15

Trp Ala Leu Gly Leu Ala Val Gly Leu Ala Ala Ser Met Ala Gly Ser
            20                  25                  30

Gly Pro Ala Asp Ala His Gly Glu Lys Ser Gln Ala Ala Phe Leu Arg
        35                  40                  45

Met Arg Thr Leu Asn Trp Tyr Asp Val Lys Trp Ser Lys Thr Ser Leu
50                  55                  60

Asn Val Asn Glu Glu Met Glu Ile Thr Gly Lys Leu His Ile Met Asp
65                  70                  75                  80

Ala Trp Pro Val Ala Val Ala Lys Pro Glu Val Ala Phe Leu Asn Val
                85                  90                  95

Gly Met Pro Gly Pro Val Leu Val Arg Glu Gly Ser Phe Leu Gly Gly
            100                 105                 110

Lys Phe Val Pro Arg Ser Thr Ser Leu Glu Leu Gly Lys Thr Tyr Glu
        115                 120                 125

Phe Arg Val Leu Leu Lys Ala Arg Arg Gln Gly Arg Trp His Val His
    130                 135                 140

Thr Gln Leu Ser Val Gln Thr Gly Gly Pro Ile Ile Gly Pro Gly Gln
145                 150                 155                 160

Trp Val Glu Ile Lys Gly Asp Met Ala Asp Phe Lys Asn Pro Val Thr
                165                 170                 175

Leu Leu Asn Gly Glu Val Ile Asp Leu Glu Gln Tyr Lys Ile Gly Asn
            180                 185                 190

Ile Tyr Phe Trp His Thr Val Trp Phe Ile Ala Gly Val Ala Trp Val
        195                 200                 205

Phe Tyr Trp Phe Arg Lys Arg Gly Phe Val Gly Arg Tyr Ile Ser Val
    210                 215                 220

Ala Ser Gly Lys Gly Gly Glu Leu Ile Thr Pro Leu Glu Arg Gln Ile
225                 230                 235                 240

Gly Ala Gly Ala Leu Ala Ala Thr Leu Leu Val Val Ile Ile Ser Tyr
                245                 250                 255

Ala Leu Thr Ala Ser Glu Phe Pro Arg Thr Ile Pro Leu Gln Ala Gly
            260                 265                 270

Asn Ile Arg Ala Ile Asp Ala Leu Asn Ile Pro Glu Ser Pro Ile Lys
        275                 280                 285

Val Glu Tyr Leu Arg Gly Thr Tyr Lys Val Pro Gly Arg Glu Leu Val
    290                 295                 300

Ala Thr Tyr Lys Ile Thr Asn Thr Gly Lys Glu Pro Val Arg Val Gly
305                 310                 315                 320

Glu Phe Ala Thr Ala Thr Leu Arg Phe Leu Asn Pro Asp Val Tyr Thr
                325                 330                 335

Gln Lys Val Asp Tyr Pro Glu Tyr Ile Leu Ala Glu Arg Gly Leu Ser
            340                 345                 350

Leu Ser Asp Asn Ala Pro Ile Ala Pro Gly Glu Thr Lys Glu Leu Thr
        355                 360                 365

Val Lys Val Gln Asp Ala Arg Trp Asp Thr Glu Arg Leu Ala Asp Leu
    370                 375                 380

Ala Tyr Asp Val Asp Ser Ser Phe Ala Gly Leu Met Phe Phe Phe Thr
385                 390                 395                 400

Pro Ser Gly Ala Arg Tyr Glu Val Glu Thr Gly Gly Pro Val Ile Pro
```

Glu Phe Leu Pro Ile
          420

<210> SEQ ID NO 13
<211> LENGTH: 414
<212> TYPE: PRT
<213> ORGANISM: Methylococcus capsulatus

<400> SEQUENCE: 13

Met Lys Thr Ile Lys Asp Arg Ile Ala Lys Trp Ser Ala Ile Gly Leu
1               5                   10                  15

Leu Ser Ala Val Ala Ala Thr Ala Phe Tyr Ala Pro Ser Ala Ser Ala
            20                  25                  30

His Gly Glu Lys Ser Gln Ala Ala Phe Met Arg Met Arg Thr Ile His
        35                  40                  45

Trp Tyr Asp Leu Ser Trp Ser Lys Glu Lys Val Lys Ile Asn Glu Thr
    50                  55                  60

Val Glu Ile Lys Gly Lys Phe His Val Phe Glu Gly Trp Pro Glu Thr
65                  70                  75                  80

Val Asp Glu Pro Asp Val Ala Phe Leu Asn Val Gly Met Pro Gly Pro
                85                  90                  95

Val Phe Ile Arg Lys Glu Ser Tyr Ile Gly Gly Gln Leu Val Pro Arg
            100                 105                 110

Ser Val Arg Leu Glu Ile Gly Lys Thr Tyr Asp Phe Arg Val Val Leu
        115                 120                 125

Lys Ala Arg Arg Pro Gly Asp Trp His Val His Thr Met Met Asn Val
    130                 135                 140

Gln Gly Gly Gly Pro Ile Ile Gly Pro Gly Lys Trp Ile Thr Val Glu
145                 150                 155                 160

Gly Ser Met Ser Glu Phe Arg Asn Pro Val Thr Thr Leu Thr Gly Gln
                165                 170                 175

Thr Val Asp Leu Glu Asn Tyr Asn Glu Gly Asn Thr Tyr Phe Trp His
            180                 185                 190

Ala Phe Trp Phe Ala Ile Gly Val Ala Trp Ile Gly Tyr Trp Ser Arg
        195                 200                 205

Arg Pro Ile Phe Ile Pro Arg Leu Leu Met Val Asp Ala Gly Arg Ala
    210                 215                 220

Asp Glu Leu Val Ser Ala Thr Asp Arg Lys Val Ala Met Gly Phe Leu
225                 230                 235                 240

Ala Ala Thr Ile Leu Ile Val Val Met Ala Met Ser Ser Ala Asn Ser
                245                 250                 255

Lys Tyr Pro Ile Thr Ile Pro Leu Gln Ala Gly Thr Met Arg Gly Met
            260                 265                 270

Lys Pro Leu Glu Leu Pro Ala Pro Thr Val Ser Val Lys Val Glu Asp
        275                 280                 285

Ala Thr Tyr Arg Val Pro Gly Arg Ala Met Arg Met Lys Leu Thr Ile
    290                 295                 300

Thr Asn His Gly Asn Ser Pro Ile Arg Leu Gly Glu Phe Tyr Thr Ala
305                 310                 315                 320

Ser Val Arg Phe Leu Asp Ser Asp Val Tyr Lys Asp Thr Thr Gly Tyr
                325                 330                 335

Pro Glu Asp Leu Leu Ala Glu Asp Gly Leu Ser Val Ser Asp Asn Ser
            340                 345                 350

```
Pro Leu Ala Pro Gly Glu Thr Arg Thr Val Asp Val Thr Ala Ser Asp
            355                 360                 365

Ala Ala Trp Glu Val Tyr Arg Leu Ser Asp Ile Ile Tyr Asp Pro Asp
    370                 375                 380

Ser Arg Phe Ala Gly Leu Leu Phe Phe Phe Asp Ala Thr Gly Asn Arg
385                 390                 395                 400

Gln Val Val Gln Ile Asp Ala Pro Leu Ile Pro Ser Phe Met
                405                 410
```

<210> SEQ ID NO 14
<211> LENGTH: 256
<212> TYPE: PRT
<213> ORGANISM: Methylosinus trichosporium

<400> SEQUENCE: 14

```
Met Ser Val Thr Thr Glu Thr Thr Ala Gly Ala Ala Gly Ser Asp
1               5                   10                  15

Ala Ile Val Asp Leu Arg Gly Met Trp Val Gly Val Ala Gly Leu Asn
                20                  25                  30

Ile Phe Tyr Leu Ile Val Arg Ile Tyr Glu Gln Ile Tyr Gly Trp Arg
            35                  40                  45

Ala Gly Leu Asp Ser Phe Ala Pro Glu Phe Gln Thr Tyr Trp Leu Ser
    50                  55                  60

Ile Leu Trp Thr Glu Ile Pro Leu Glu Leu Val Ser Gly Leu Ala Leu
65                  70                  75                  80

Ala Gly Trp Leu Trp Lys Thr Arg Asp Arg Asn Val Asp Ala Val Ala
                85                  90                  95

Pro Arg Glu Glu Leu Arg Arg His Val Val Leu Val Glu Trp Leu Val
            100                 105                 110

Val Tyr Ala Val Ala Ile Tyr Trp Gly Ala Ser Phe Phe Thr Glu Gln
        115                 120                 125

Asp Gly Thr Trp His Met Thr Val Ile Arg Asp Thr Asp Phe Thr Pro
    130                 135                 140

Ser His Ile Ile Glu Phe Tyr Met Ser Tyr Pro Ile Tyr Ser Ile Met
145                 150                 155                 160

Ala Val Gly Ala Phe Phe Tyr Ala Lys Thr Arg Ile Pro Tyr Phe Ala
                165                 170                 175

His Gly Phe Ser Leu Ala Phe Leu Ile Val Ala Ile Gly Pro Phe Met
            180                 185                 190

Ile Ile Pro Asn Val Gly Leu Asn Glu Trp Gly His Thr Phe Trp Phe
        195                 200                 205

Met Glu Glu Leu Phe Val Ala Pro Leu His Trp Gly Phe Val Phe Phe
    210                 215                 220

Gly Trp Met Ala Leu Gly Val Phe Gly Val Val Leu Gln Ile Leu Met
225                 230                 235                 240

Gly Val Lys Arg Leu Ile Gly Lys Asp Cys Val Ala Ala Leu Val Gly
                245                 250                 255
```

<210> SEQ ID NO 15
<211> LENGTH: 287
<212> TYPE: PRT
<213> ORGANISM: Methylacidiphilum infernorum

<400> SEQUENCE: 15

```
Met Ala Asn Glu Arg Ile Ala Thr Ala Gly Ala Met Glu Val Thr Thr
1               5                   10                  15
```

```
Ser Ile Glu Val Val Pro Lys Lys Glu Tyr Phe Asn Asn Trp Arg Phe
            20                  25                  30

Tyr Leu Tyr Cys Ile Leu Leu Ser Leu Phe Tyr Gly Ala Cys Met Leu
        35                  40                  45

Tyr Gln Arg Ala Phe Ala Ile Thr Lys Gly Ile Asp Tyr Thr Ser Gln
50                  55                  60

Glu Phe Gln Gln Tyr Trp Met Thr Leu Phe Trp Gly Ile Thr Ile Met
65                  70                  75                  80

Asn Val Val Ile Trp Ala Val Thr Trp Gly Trp Ile Trp Tyr Val Tyr
                85                  90                  95

Arg Asp Arg His Leu Asp Gln Val Thr Pro Gly Glu Glu Leu Lys Arg
                100                 105                 110

Trp Tyr Ser Asn Trp Leu Leu Thr Leu Gly Val Tyr Ala Trp Ala Leu
            115                 120                 125

Val Trp Ala Val Phe Phe Val Glu Gln Asp Gly Val Trp His Ser Ser
        130                 135                 140

Met Val Arg Asp Thr Glu Phe Thr Pro Ser His Ile Phe Asn Phe Tyr
145                 150                 155                 160

Leu Ser Trp Pro Ile Phe Ile Asn Phe Gly Val Ala Gly Leu Met Leu
                165                 170                 175

Thr Arg Thr Arg Leu Pro Val Met Gly Lys Lys Trp Leu Leu Pro Leu
                180                 185                 190

Val Met Glu Val Ala Trp Pro Ile Met Phe Ile Pro Leu Ile Gly Glu
            195                 200                 205

Asn Glu Trp Gly His Ser Ala Trp Ile Leu Glu Glu Trp Phe Ala Ala
210                 215                 220

Pro Leu His Trp Thr Phe Val Pro Phe Ala Trp Ala Ala Val Trp Phe
225                 230                 235                 240

Leu Gly Asn Gly Phe Asp Met Phe Pro Arg Ile Ala Ala Val Leu Lys
                245                 250                 255

Ala Thr Tyr Phe Gly Glu Lys Cys Met Ser Ala Ala Glu Ala Met Glu
                260                 265                 270

Asn Pro Glu Glu Ala Thr Asn Pro Val His Thr Leu Pro Gly Met
            275                 280                 285

<210> SEQ ID NO 16
<211> LENGTH: 265
<212> TYPE: PRT
<213> ORGANISM: Methylocapsa acidiphila

<400> SEQUENCE: 16

Met Ser Leu Ile Thr Glu Thr Ser Pro Ser Arg Ala Asp Ala Ala
1               5                   10                  15

Leu Ser Ala Ala Thr Pro Val Trp Asp Pro Lys Pro Phe Ile Ile Gly
                20                  25                  30

Thr Val Ala Leu Thr Val Phe Tyr Ile Gly Val Arg Ile Tyr Glu Gln
            35                  40                  45

Val Phe Gly Trp Tyr Ala Gly Leu Asp Ser Phe Ser Pro Glu Phe Gln
        50                  55                  60

Lys Tyr Trp Met Thr Ile Leu Tyr Ile Glu Glu Pro Thr Glu Leu Ile
65                  70                  75                  80

Ala Phe Leu Gly Leu Ile Gly Tyr Leu Trp Lys Thr Arg Pro Asn Asp
                85                  90                  95

Leu Asp Thr Val Ala Pro Arg Glu Glu Leu Arg Arg Ile Phe Tyr Leu
                100                 105                 110
```

```
Phe Asn Trp Ile Phe Val Tyr Gly Val Ala Ile Tyr Trp Gly Ala Ser
        115                 120                 125

Tyr Phe Thr Glu Gln Asp Gly Thr Trp His Gln Thr Val Ile Arg Asp
130                 135                 140

Thr Asp Phe Thr Pro Ser His Ile Ile Glu Phe Tyr Met Ser Tyr Pro
145                 150                 155                 160

Ile Tyr Ile Ile Met Gly Val Gly Gly Phe Val Tyr Ala Arg Thr Arg
                165                 170                 175

Leu Pro Thr Phe Gly Ser Lys Gly Tyr Ser Val Ala Tyr Leu Leu Leu
            180                 185                 190

Phe Val Gly Pro Phe Met Ile Phe Pro Asn Val Ala Leu Asn Glu Trp
        195                 200                 205

Gly His Thr Phe Trp Phe Met Glu Glu Leu Phe Val Ala Pro Leu His
    210                 215                 220

Trp Met Phe Val Phe Phe Gly Trp Phe Met Leu Ser Val Phe Gly Val
225                 230                 235                 240

Ser Leu Gln Ile Leu Gly Arg Ile Lys Glu Leu Cys Thr Gly Tyr Glu
                245                 250                 255

Asp Val Val Gly Leu Glu Pro Ala Glu
            260                 265

<210> SEQ ID NO 17
<211> LENGTH: 250
<212> TYPE: PRT
<213> ORGANISM: Methylomicrobium alcaliphilum

<400> SEQUENCE: 17

Met Ala Ala Thr Thr Glu Ser Val Lys Ala Asp Ala Ala Glu Ala Pro
1               5                   10                  15

Leu Leu Asn Lys Lys Asn Ile Ile Ala Gly Ala Ser Leu Tyr Leu Val
            20                  25                  30

Phe Tyr Ala Trp Val Arg Trp Tyr Glu Gly Val Tyr Gly Trp Ser Ala
        35                  40                  45

Gly Leu Asp Ser Phe Ala Pro Glu Phe Glu Thr Tyr Trp Met Asn Phe
50                  55                  60

Leu Tyr Ile Glu Met Val Leu Glu Val Leu Thr Ala Ser Val Leu Trp
65                  70                  75                  80

Gly Tyr Ile Trp Lys Ser Arg Asp Arg Lys Val Met Ser Ile Thr Pro
                85                  90                  95

Arg Glu Glu Leu Arg Arg His Phe Thr His Trp Thr Trp Leu Met Met
            100                 105                 110

Tyr Gly Ile Ala Ile Tyr Phe Gly Ala Ser Tyr Phe Thr Glu Gln Asp
        115                 120                 125

Gly Thr Trp His Gln Thr Ile Val Arg Asp Thr Asp Phe Thr Pro Ser
130                 135                 140

His Ile Ile Glu Phe Tyr Leu Ser Tyr Pro Ile Tyr Ile Ile Thr Gly
145                 150                 155                 160

Gly Ala Ser Phe Leu Tyr Ala Lys Thr Arg Leu Pro Thr Tyr Gln Gln
                165                 170                 175

Gly Leu Ser Leu Gln Tyr Leu Val Val Val Gly Pro Phe Met Ile
            180                 185                 190

Leu Pro Asn Val Gly Leu Asn Glu Trp Gly His Thr Phe Trp Phe Met
        195                 200                 205

Glu Glu Leu Phe Val Ala Pro Leu His Tyr Gly Phe Val Phe Phe Gly
```

```
            210                 215                 220
Trp Ser Ala Leu Gly Val Leu Gly Val Ile Asn Ile Glu Leu Gly Ala
225                 230                 235                 240

Leu Ser Lys Leu Leu Lys Lys Asp Leu Ala
                245                 250

<210> SEQ ID NO 18
<211> LENGTH: 256
<212> TYPE: PRT
<213> ORGANISM: Methylocystis sp.

<400> SEQUENCE: 18

Met Ser Ser Thr Thr Asp Thr Ala Ala Arg Ala Ala Gly Thr Glu
1               5                   10                  15

Ala Val Val Asp Leu Lys Gly Met Trp Ile Gly Leu Ala Val Leu Asn
                20                  25                  30

Gly Phe Tyr Leu Val Val Arg Ile Tyr Glu Gln Ile Tyr Gly Trp Arg
            35                  40                  45

Ala Gly Leu Asp Ser Phe Ala Pro Glu Phe Gln Thr Tyr Trp Met Ser
        50                  55                  60

Ile Leu Trp Thr Glu Ile Pro Leu Glu Leu Ile Ser Gly Ile Gly Leu
65                  70                  75                  80

Ala Gly Phe Leu Trp Lys Thr Arg Thr Arg Asp Phe Ser Thr Leu Thr
                85                  90                  95

Ala Arg Glu Glu Met Arg Arg Leu Val Val Glu Val Gln Trp Leu Val
            100                 105                 110

Val Tyr Ala Ala Ala Ile Tyr Trp Gly Ala Ser Phe Phe Thr Glu Gln
        115                 120                 125

Asp Gly Thr Trp His Met Thr Val Ile Arg Asp Thr Asp Phe Thr Pro
    130                 135                 140

Ser His Ile Ile Glu Phe Tyr Met Ser Tyr Pro Ile Tyr Ser Val Ile
145                 150                 155                 160

Ala Val Gly Gly Phe Phe Tyr Ala Lys Thr Arg Leu Pro Tyr Phe Ala
                165                 170                 175

Lys Gly Tyr Ser Val Ala Tyr Leu Ile Val Ala Ile Gly Pro Phe Met
            180                 185                 190

Ile Ile Pro Asn Val Gly Leu Asn Glu Trp Gly His Thr Phe Trp Phe
        195                 200                 205

Met Glu Glu Leu Phe Val Ala Pro Leu His Trp Gly Phe Val Phe Phe
    210                 215                 220

Gly Trp Met Ala Leu Gly Val Phe Gly Val Val Leu Gln Leu Leu Ile
225                 230                 235                 240

Asn Ile Gln Arg Leu Ile Gly Lys Glu Gly Val Ala Leu Leu Thr Glu
                245                 250                 255

<210> SEQ ID NO 19
<211> LENGTH: 518
<212> TYPE: PRT
<213> ORGANISM: Methylocystis sp.
<220> FEATURE:
<221> NAME/KEY: VARIANT
<222> LOCATION: 296, 336
<223> OTHER INFORMATION: Xaa = Any Amino Acid

<400> SEQUENCE: 19

Gly Asp Asp Ala Leu Lys Val Asn Arg Ala Pro Val Gly Val Glu Pro
1               5                   10                  15
```

-continued

```
Gln Glu Val His Lys Trp Leu Gln Ser Phe Asn Trp Asp Phe Lys Asp
             20                  25                  30

Asn Arg Thr Lys Tyr Ala Thr Lys Tyr His Met Ala Asn Gln Thr Lys
         35                  40                  45

Glu Gln Phe Lys Val Ile Ala Lys Glu Tyr Ala Arg Met Glu Ala Ala
     50                  55                  60

Lys Asp Glu Arg Gln Phe Gly Thr Leu Leu Asp Gly Leu Thr Arg Leu
 65                  70                  75                  80

Gly Ala Gly Asn Lys Val His Pro Arg Trp Gly Glu Thr Met Lys Val
                 85                  90                  95

Ile Ser Asn Phe Leu Glu Val Gly Tyr Asn Ala Ile Ala Ala Ser
             100                 105                 110

Ala Met Leu Trp Asp Ser Ala Thr Ala Glu Gln Lys Asn Gly Tyr
         115                 120                 125

Leu Ala Gln Val Leu Asp Glu Ile Arg His Thr His Gln Cys Ala Phe
     130                 135                 140

Ile Asn His Tyr Tyr Ser Lys His Tyr His Asp Pro Ala Gly His Asn
145                 150                 155                 160

Asp Ala Arg Arg Thr Arg Ala Ile Gly Pro Leu Trp Lys Gly Met Lys
                165                 170                 175

Arg Val Phe Ala Asp Gly Phe Ile Ser Gly Asp Ala Val Glu Cys Ser
            180                 185                 190

Val Asn Leu Gln Leu Val Gly Glu Ala Cys Phe Thr Asn Pro Leu Ile
        195                 200                 205

Val Ala Val Thr Glu Trp Ala Ser Ala Asn Gly Asp Glu Ile Thr Pro
    210                 215                 220

Thr Val Phe Leu Ser Val Glu Thr Asp Glu Leu Arg His Met Ala Asn
225                 230                 235                 240

Gly Tyr Gln Thr Val Val Ser Ile Ala Asn Asp Pro Ala Ala Lys
                245                 250                 255

Tyr Leu Asn Thr Asp Leu Asn Asn Ala Phe Trp Thr Gln Gln Lys Tyr
            260                 265                 270

Phe Thr Pro Ala Leu Gly Tyr Leu Phe Glu Tyr Gly Ser Lys Phe Lys
        275                 280                 285

Val Glu Pro Trp Val Lys Thr Xaa Asn Arg Trp Val Tyr Glu Asp Trp
    290                 295                 300

Gly Gly Ile Trp Ile Gly Arg Leu Gly Lys Tyr Gly Val Glu Ser Pro
305                 310                 315                 320

Arg Ser Leu Arg Asp Ala Lys Arg Asp Ala Tyr Trp Ala His His Xaa
                325                 330                 335

Leu Ala Leu Ala Ala Tyr Ala Leu Trp Pro Leu Gly Phe Ser Arg Leu
            340                 345                 350

Ala Leu Pro Asp Glu Glu Asp Gln Glu Trp Phe Glu Ala Asn Tyr Pro
        355                 360                 365

Gly Trp Ala Asp His Tyr Gly Lys Ile Tyr Asn Glu Trp Lys Arg Leu
    370                 375                 380

Gly Tyr Glu Asp Pro Lys Ser Gly Phe Ile Pro Tyr Ala Trp Leu Leu
385                 390                 395                 400

Glu Asn Gly His Asp Val Tyr Ile Asp Arg Val Ser Gln Val Pro Phe
                405                 410                 415

Ile Pro Ser Leu Ala Lys Gly Ser Gly Ser Leu Arg Val His Glu Phe
            420                 425                 430

Asn Gly Lys Lys His Ser Leu Thr Asp Asp Trp Gly Glu Arg Met Trp
```

```
                    435                 440                 445
Leu Thr Glu Pro Glu Arg Tyr Glu Cys His Asn Ile Phe Glu Gln Tyr
    450                 455                 460

Glu Gly Arg Glu Leu Ser Glu Val Ile Ala Glu Gly His Gly Val Arg
465                 470                 475                 480

Ser Asp Gly Lys Thr Leu Ile Ala Gln Pro His Val Arg Gly Asp Asn
                485                 490                 495

Leu Trp Thr Leu Glu Asp Ile Arg Arg Ala Gly Cys Val Phe Pro Asp
            500                 505                 510

Pro Leu Ser Lys Phe Asn
        515

<210> SEQ ID NO 20
<211> LENGTH: 527
<212> TYPE: PRT
<213> ORGANISM: Methylococcus capsulatus

<400> SEQUENCE: 20

Met Ala Leu Ser Thr Ala Thr Lys Ala Ala Thr Asp Ala Leu Ala Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Asn Arg Thr Lys Tyr Ala Thr
        35                  40                  45

Lys Tyr Lys Met Ala Asn Glu Thr Lys Glu Gln Phe Lys Leu Ile Ala
    50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110

Gly Glu Tyr Asn Ala Ile Ala Ala Thr Gly Met Leu Trp Asp Ser Ala
        115                 120                 125

Gln Ala Ala Glu Gln Lys Asn Gly Tyr Leu Ala Gln Val Leu Asp Glu
    130                 135                 140

Ile Arg His Thr His Gln Cys Ala Tyr Val Asn Tyr Tyr Phe Ala Lys
145                 150                 155                 160

Asn Gly Gln Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Leu Asn Leu Gln Leu Val Gly
        195                 200                 205

Glu Ala Cys Phe Thr Asn Pro Leu Ile Val Ala Val Thr Glu Trp Ala
    210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285
```

```
Leu Phe Glu Tyr Gly Ser Lys Phe Lys Val Glu Pro Trp Val Lys Thr
290                 295                 300

Trp Asn Arg Trp Val Tyr Glu Asp Trp Gly Ile Trp Ile Gly Arg
305                 310                 315                 320

Leu Gly Lys Tyr Gly Val Glu Ser Pro Arg Ser Leu Lys Asp Ala Lys
                325                 330                 335

Gln Asp Ala Tyr Trp Ala His His Asp Leu Tyr Leu Ala Tyr Ala
            340                 345                 350

Leu Trp Pro Thr Gly Phe Phe Arg Leu Ala Leu Pro Asp Gln Glu Glu
                355                 360                 365

Met Glu Trp Phe Glu Ala Asn Tyr Pro Gly Trp Tyr Asp His Tyr Gly
370                 375                 380

Lys Ile Tyr Glu Glu Trp Arg Ala Arg Gly Cys Glu Asp Pro Ser Ser
385                 390                 395                 400

Gly Phe Ile Pro Leu Met Trp Phe Ile Glu Asn Asn His Pro Ile Tyr
                405                 410                 415

Ile Asp Arg Val Ser Gln Val Pro Phe Cys Pro Ser Leu Ala Lys Gly
                420                 425                 430

Ala Ser Thr Leu Arg Val His Glu Tyr Asn Gly Gln Met His Thr Phe
        435                 440                 445

Ser Asp Gln Trp Gly Glu Arg Met Trp Leu Ala Glu Pro Glu Arg Tyr
450                 455                 460

Glu Cys Gln Asn Ile Phe Glu Gln Tyr Glu Gly Arg Glu Leu Ser Glu
465                 470                 475                 480

Val Ile Ala Glu Leu His Gly Leu Arg Ser Asp Gly Lys Thr Leu Ile
                485                 490                 495

Ala Gln Pro His Val Arg Gly Asp Lys Leu Trp Thr Leu Asp Asp Ile
                500                 505                 510

Lys Arg Leu Asn Cys Val Phe Lys Asn Pro Val Lys Ala Phe Asn
515                 520                 525

<210> SEQ ID NO 21
<211> LENGTH: 526
<212> TYPE: PRT
<213> ORGANISM: Methylosinus trichosporium

<400> SEQUENCE: 21

Met Ala Ile Ser Leu Ala Thr Lys Ala Ala Thr Asp Ala Leu Lys Val
1               5                   10                  15

Asn Arg Ala Pro Val Gly Val Glu Pro Gln Glu Val His Lys Trp Leu
                20                  25                  30

Gln Ser Phe Asn Trp Asp Phe Lys Glu Asn Arg Thr Lys Tyr Pro Thr
            35                  40                  45

Lys Tyr His Met Ala Asn Glu Thr Lys Glu Gln Phe Lys Val Ile Ala
    50                  55                  60

Lys Glu Tyr Ala Arg Met Glu Ala Ala Lys Asp Glu Arg Gln Phe Gly
65                  70                  75                  80

Thr Leu Leu Asp Gly Leu Thr Arg Leu Gly Ala Gly Asn Lys Val His
                85                  90                  95

Pro Arg Trp Gly Glu Thr Met Lys Val Ile Ser Asn Phe Leu Glu Val
                100                 105                 110

Gly Glu Tyr Asn Ala Ile Ala Ala Ser Ala Met Leu Trp Asp Ser Ala
            115                 120                 125

Thr Ala Ala Glu Gln Lys Asn Gly Tyr Leu Ala Gln Val Leu Asp Glu
130                 135                 140
```

Ile Arg His Thr His Gln Cys Ala Phe Ile Asn His Tyr Tyr Ser Lys
145                 150                 155                 160

His Tyr His Asp Pro Ala Gly His Asn Asp Ala Arg Thr Arg Ala
        165                 170                 175

Ile Gly Pro Leu Trp Lys Gly Met Lys Arg Val Phe Ala Asp Gly Phe
        180                 185                 190

Ile Ser Gly Asp Ala Val Glu Cys Ser Val Asn Leu Gln Leu Val Gly
        195                 200                 205

Glu Ala Cys Phe Thr Asn Pro Leu Ile Val Ala Val Thr Glu Trp Ala
210                 215                 220

Ser Ala Asn Gly Asp Glu Ile Thr Pro Thr Val Phe Leu Ser Val Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Phe Leu Asn Thr Asp Leu Asn
            260                 265                 270

Asn Ala Phe Trp Thr Gln Gln Lys Tyr Phe Thr Pro Val Leu Gly Tyr
        275                 280                 285

Leu Phe Glu Tyr Gly Ser Lys Phe Lys Val Glu Pro Trp Val Lys Thr
        290                 295                 300

Trp Asn Arg Trp Val Tyr Glu Asp Trp Gly Ile Trp Ile Gly Arg
305                 310                 315                 320

Leu Gly Lys Tyr Gly Val Glu Ser Pro Ala Ser Leu Arg Asp Ala Lys
                325                 330                 335

Arg Asp Ala Tyr Trp Ala His His Asp Leu Ala Leu Ala Ala Tyr Ala
            340                 345                 350

Met Trp Pro Leu Gly Phe Ala Arg Leu Ala Leu Pro Asp Glu Glu Asp
        355                 360                 365

Gln Ala Trp Phe Glu Ala Asn Tyr Pro Gly Trp Ala Asp His Tyr Gly
370                 375                 380

Lys Ile Phe Asn Glu Trp Lys Lys Leu Gly Tyr Glu Asp Pro Lys Ser
385                 390                 395                 400

Gly Phe Ile Pro Tyr Lys Trp Leu Leu Glu Asn Gly His Asp Val Tyr
                405                 410                 415

Ile Asp Arg Val Ser Gln Val Pro Phe Ile Pro Ser Leu Ala Lys Gly
            420                 425                 430

Ser Gly Ser Leu Arg Val His Glu Phe Asn Gly Lys Lys His Ser Leu
        435                 440                 445

Thr Asp Asp Trp Gly Glu Arg Gln Trp Leu Ile Glu Pro Glu Arg Tyr
        450                 455                 460

Glu Cys His Asn Val Phe Glu Gln Tyr Glu Gly Arg Glu Leu Ser Glu
465                 470                 475                 480

Val Ile Ala Glu Gly His Gly Val Arg Ser Asp Gly Lys Thr Leu Ile
                485                 490                 495

Ala Gln Pro His Thr Arg Gly Asp Asn Leu Trp Thr Leu Glu Asp Ile
            500                 505                 510

Lys Arg Ala Gly Cys Val Phe Pro Asp Pro Leu Ala Lys Phe
515                 520                 525

<210> SEQ ID NO 22
<211> LENGTH: 525
<212> TYPE: PRT
<213> ORGANISM: Methylomicrobium japanense

<400> SEQUENCE: 22

```
Met Ala Ile Ser Ala Ala Thr Lys Ala Ala Thr Asp Ala Leu Lys Ile
1               5                   10                  15

Asn Arg Ala Pro Val Ser Val Gly Ala Gln Glu Val His Arg Trp Leu
            20                  25                  30

Gln Ser Phe Ser Trp Asp Phe Glu Lys Asn Arg Ser Lys Tyr Pro Thr
        35                  40                  45

Lys Tyr His Met Ala Asn Asp Thr Lys Glu Gln Phe Lys Leu Ile Ala
    50                  55                  60

Lys Glu Tyr Ala Arg Met Glu Ser Val Lys Asp Glu Arg Gln Phe Gly
65                  70                  75                  80

Ser Leu Gln Asp Ala Leu Thr Arg Leu Asp Ala Gly Asn Arg Ile His
                85                  90                  95

Pro Lys Trp Gly Glu Thr Met Lys Val Ala Ser Asn Phe Leu Glu Val
            100                 105                 110

Gly Glu Tyr Asn Ala Ile Ala Ala Thr Gly Met Leu Trp Asp Ser Ala
        115                 120                 125

Thr Ala Pro Glu Gln Lys Asn Gly Tyr Leu Ala Gln Val Leu Asp Glu
    130                 135                 140

Ile Arg His Thr Asn Gln Cys Gly Tyr Val Asn Tyr Tyr Thr Lys
145                 150                 155                 160

His Phe His Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Ile Asn Leu Gln Leu Val Gly
        195                 200                 205

Glu Ala Cys Phe Thr Asn Pro Leu Ile Val Ala Ile Thr Glu Trp Ala
    210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Glu Ala Ala Ser Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285

Leu Phe Glu Tyr Gly Ser Lys Phe Lys Val Glu Pro Trp Val Lys Thr
    290                 295                 300

Trp Asn Arg Trp Val Tyr Glu Asp Trp Gly Gly Ile Trp Ile Gly Arg
305                 310                 315                 320

Leu Gly Lys Tyr Gly Val Glu Ser Pro Arg Ser Leu Arg Asp Ala Lys
                325                 330                 335

Lys Asp Ala Tyr Trp Ala His His Asp Leu Phe Leu Leu Ala Tyr Ala
            340                 345                 350

Leu Trp Pro Thr Gly Phe Phe Arg Leu Ser Leu Pro Thr Gln Glu Glu
        355                 360                 365

Met Asp Trp Tyr Glu Ala Asn Tyr Pro Gly Trp Tyr Asp His Tyr Gly
    370                 375                 380

Lys Ile Tyr Glu Glu Trp Arg Ala Arg Gly Cys Glu Asp Pro Asn Ser
385                 390                 395                 400

Gly Phe Ile Pro Leu Met Trp Phe Ile Glu Asn Asn His Gln Ile Tyr
                405                 410                 415
```

```
Ile Asp Arg Val Ser Gln Val Pro Phe Cys Pro Ser Leu Cys Lys Gly
            420                 425                 430

Ala Ser Thr Leu Arg Val His Glu Leu Asn Gly Lys Lys His Ser Phe
            435                 440                 445

Ser Asp Asp Trp Gly Glu Arg Met Trp Leu Met Glu Pro Glu Arg Tyr
450                 455                 460

Glu Cys Gln Asn Met Phe Glu Gln Tyr Ala Gly Arg Glu Leu Ser Glu
465                 470                 475                 480

Val Ile Ala Glu Gly His Gly Val Arg Ser Asp Gly Lys Thr Leu Ile
            485                 490                 495

Ala Gln Pro His Thr Asp Lys Asn Gly Lys Leu Trp Thr Leu Asp Asp
            500                 505                 510

Ile Lys Lys Leu Asn Cys Val Phe Lys Asp Pro Leu Ala
            515                 520                 525

<210> SEQ ID NO 23
<211> LENGTH: 526
<212> TYPE: PRT
<213> ORGANISM: Methylocella silvestris

<400> SEQUENCE: 23

Met Ala Leu Ser Thr Ala Thr Lys Ala Ala Ser Asp Ala Leu Gly Ala
1               5                   10                  15

Asn Arg Ala Pro Thr Ser Val Ser Pro Gln Glu Val His Arg Trp Leu
            20                  25                  30

Gln Ser Phe Asn Trp Asp Phe Ala Gln Asn Arg Thr Lys Tyr Pro Thr
        35                  40                  45

Lys Tyr His Met Ala Asn Asp Thr Lys Glu Gln Phe Lys Leu Ile Ala
    50                  55                  60

Lys Glu Tyr Ala Arg Met Glu Ser Val Lys Asp Glu Arg Gln Phe Gly
65                  70                  75                  80

Thr Leu Leu Asp Gly Leu Thr Arg Leu Glu Ala Gly Asn Arg Val His
                85                  90                  95

Pro Arg Trp Gly Glu Thr Met Lys Val Ala Ser Asn Phe Leu Glu Val
            100                 105                 110

Gly Glu Tyr Asn Ala Ile Ala Ala Ser Ala Met Leu Trp Asp Ser Ala
        115                 120                 125

Ser Ala Ala Glu Gln Lys Asn Gly Tyr Leu Ala Gln Val Leu Asp Glu
    130                 135                 140

Ile Arg His Thr His Gln Cys Gly Phe Val Asn Tyr Tyr Phe Ser Lys
145                 150                 155                 160

His Tyr His Asp Pro Ala Gly His Asn Asp Ala Arg Arg Thr Arg Ala
                165                 170                 175

Ile Gly Pro Leu Trp Lys Gly Met Lys Arg Val Phe Ala Asp Gly Phe
            180                 185                 190

Ile Ser Gly Asp Ala Val Glu Cys Ser Val Asn Leu Gln Leu Val Gly
        195                 200                 205

Glu Ala Cys Phe Thr Asn Pro Leu Ile Val Ala Val Thr Glu Trp Ala
    210                 215                 220

Ser Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ala Gln Lys Tyr Leu Asn Thr Asp Leu Asn
```

```
                    260                 265                 270
Asn Ala Phe Trp Thr Gln Gln Lys Tyr Phe Thr Pro Val Leu Gly Met
            275                 280                 285
Leu Phe Glu Tyr Gly Ser Lys Phe Lys Val Glu Pro Trp Val Lys Thr
        290                 295                 300
Trp Asn Arg Trp Val Tyr Glu Asp Trp Gly Ile Trp Ile Gly Arg
305                 310                 315                 320
Leu Ala Lys Tyr Gly Val Asn Ser Pro Ser Leu Arg Asp Ala Lys
            325                 330                 335
Lys Asp Ala Tyr Trp Ala His His Asp Leu Phe Leu Ala Tyr Ala
            340                 345                 350
Leu Trp Pro Thr Gly Phe Phe Arg Leu Ser Leu Pro Asp Glu Glu Asp
            355                 360                 365
Met Glu Trp Phe Glu Ala Asn Tyr Pro Gly Trp Asp Ala His Tyr Gly
            370                 375                 380
Lys Ile Leu Arg Glu Trp Lys Ala Leu Gly Cys Glu Asp Pro Lys Ser
385                 390                 395                 400
Gly Phe Leu Pro Ile Gln Trp Leu Val Gln Asn Gly His Gln Val Tyr
            405                 410                 415
Val Asp Arg Val Ser Gln Val Pro Phe Cys Pro Thr Leu Ala Lys Cys
            420                 425                 430
Ser Gly Ser Leu Arg Val His Glu Phe Asn Gly Gln Lys His Ser Phe
            435                 440                 445
Ser Asp Asp Trp Gly Glu Arg Met Trp Leu Ser Glu Pro Glu Arg Tyr
            450                 455                 460
Glu Cys Gln Ser Val Phe Glu Gln Tyr Ser Gly Arg Glu Leu Ser Asp
465                 470                 475                 480
Val Ile Val Glu Gly His Gly Val Arg Ala Asp Gly Lys Thr Leu Ile
            485                 490                 495
Gly Gln Pro His Val Ala Gly Ser Asn Leu Trp Thr Val Glu Asp Leu
            500                 505                 510
Lys Arg Ala Asn Cys Val Phe Ala Asp Pro Leu Ala Gly Phe
            515                 520                 525

<210> SEQ ID NO 24
<211> LENGTH: 526
<212> TYPE: PRT
<213> ORGANISM: Methylosinus trichosporium

<400> SEQUENCE: 24

Met Ala Ile Ser Leu Ala Thr Lys Ala Ala Thr Asp Ala Leu Lys Val
1               5                   10                  15
Asn Arg Ala Pro Val Gly Val Glu Pro Gln Glu Val His Lys Trp Leu
            20                  25                  30
Gln Ser Phe Asn Trp Asp Phe Lys Glu Asn Arg Thr Lys Tyr Pro Thr
        35                  40                  45
Lys Tyr His Met Ala Asn Glu Thr Lys Glu Gln Phe Lys Val Ile Ala
    50                  55                  60
Lys Glu Tyr Ala Arg Met Glu Ala Ala Lys Asp Glu Arg Gln Phe Gly
65              70                  75                  80
Thr Leu Leu Asp Gly Leu Thr Arg Leu Gly Ala Gly Asn Lys Val His
            85                  90                  95
Pro Arg Trp Gly Glu Thr Met Lys Val Ile Ser Asn Phe Leu Glu Val
            100                 105                 110
```

```
Gly Glu Tyr Asn Ala Ile Ala Ala Ser Ala Met Leu Trp Asp Ser Ala
            115                 120                 125
Thr Ala Ala Glu Gln Lys Asn Gly Tyr Leu Ala Gln Val Leu Asp Glu
        130                 135                 140
Ile Arg His Thr His Gln Cys Ala Phe Ile Asn His Tyr Tyr Ser Lys
145                 150                 155                 160
His Tyr His Asp Pro Ala Gly His Asn Asp Ala Arg Arg Thr Arg Ala
                165                 170                 175
Ile Gly Pro Leu Trp Lys Gly Met Lys Arg Val Phe Ala Asp Gly Phe
            180                 185                 190
Ile Ser Gly Asp Ala Val Glu Cys Ser Val Asn Leu Gln Leu Val Gly
        195                 200                 205
Glu Ala Cys Phe Thr Asn Pro Leu Ile Val Ala Val Thr Glu Trp Ala
    210                 215                 220
Ser Ala Asn Gly Asp Glu Ile Thr Pro Thr Val Phe Leu Ser Val Glu
225                 230                 235                 240
Thr Asp Glu Leu Arg His Met Ala Asn Gly Tyr Gln Thr Val Val Ser
                245                 250                 255
Ile Ala Asn Asp Pro Ala Ser Ala Lys Phe Leu Asn Thr Asp Leu Asn
            260                 265                 270
Asn Ala Phe Trp Thr Gln Gln Lys Tyr Phe Thr Pro Val Leu Gly Tyr
        275                 280                 285
Leu Phe Glu Tyr Gly Ser Lys Phe Lys Val Glu Pro Trp Val Lys Thr
    290                 295                 300
Trp Asn Arg Trp Val Tyr Glu Asp Trp Gly Ile Trp Ile Gly Arg
305                 310                 315                 320
Leu Gly Lys Tyr Gly Val Glu Ser Pro Ala Ser Leu Arg Asp Ala Lys
                325                 330                 335
Arg Asp Ala Tyr Trp Ala His His Asp Leu Ala Leu Ala Ala Tyr Ala
            340                 345                 350
Met Trp Pro Leu Gly Phe Ala Arg Leu Ala Leu Pro Asp Glu Glu Asp
        355                 360                 365
Gln Ala Trp Phe Glu Ala Asn Tyr Pro Gly Trp Ala Asp His Tyr Gly
    370                 375                 380
Lys Ile Phe Asn Glu Trp Lys Lys Leu Gly Tyr Glu Asp Pro Lys Ser
385                 390                 395                 400
Gly Phe Ile Pro Tyr Gln Trp Leu Leu Ala Asn Gly His Asp Val Tyr
                405                 410                 415
Ile Asp Arg Val Ser Gln Val Pro Phe Ile Pro Ser Leu Ala Lys Gly
            420                 425                 430
Thr Gly Ser Leu Arg Val His Glu Phe Asn Gly Lys Lys His Ser Leu
        435                 440                 445
Thr Asp Asp Trp Gly Glu Arg Gln Trp Leu Ile Glu Pro Glu Arg Tyr
    450                 455                 460
Glu Cys His Asn Val Phe Glu Gln Tyr Glu Gly Arg Glu Leu Ser Glu
465                 470                 475                 480
Val Ile Ala Glu Gly His Gly Val Arg Ser Asp Gly Lys Thr Leu Ile
                485                 490                 495
Ala Gln Pro His Thr Arg Gly Asp Asn Leu Trp Thr Leu Glu Asp Ile
            500                 505                 510
Lys Arg Ala Gly Cys Val Phe Pro Asp Pro Leu Ala Lys Phe
        515                 520                 525
```

```
<210> SEQ ID NO 25
<211> LENGTH: 395
<212> TYPE: PRT
<213> ORGANISM: Methylosinus sporium

<400> SEQUENCE: 25
```

| | | | | | | | | | | | | | | |
|---|---|---|---|---|---|---|---|---|---|---|---|---|---|---|
| Met | Ser | Gln | Pro | Gln | Ser | Ser | Gln | Val | Thr | Lys | Arg | Gly | Leu | Thr | Asp |
| 1 | | | | 5 | | | | | 10 | | | | | 15 | |

| Pro | Glu | Arg | Ala | Ala | Ile | Ile | Ala | Ala | Val | Pro | Asp | His | Ala | Leu |
|---|---|---|---|---|---|---|---|---|---|---|---|---|---|---|
| | | 20 | | | | 25 | | | | | 30 | | | |

| Asp | Thr | Gln | Arg | Lys | Tyr | His | Tyr | Phe | Ile | Gln | Pro | Arg | Trp | Lys | Arg |
|---|---|---|---|---|---|---|---|---|---|---|---|---|---|---|---|
| | | 35 | | | | | 40 | | | | | 45 | | | |

| Leu | Ser | Glu | Tyr | Glu | Gln | Leu | Ser | Cys | Tyr | Ala | Gln | Pro | Asn | Pro | Asp |
|---|---|---|---|---|---|---|---|---|---|---|---|---|---|---|---|
| | 50 | | | | | 55 | | | | | 60 | | | | |

| Trp | Ile | Ala | Gly | Gly | Leu | Asp | Trp | Gly | Asp | Trp | Thr | Gln | Lys | Phe | His |
|---|---|---|---|---|---|---|---|---|---|---|---|---|---|---|---|
| 65 | | | | | 70 | | | | | 75 | | | | | 80 |

| Gly | Gly | Arg | Pro | Ser | Trp | Gly | Asn | Glu | Ser | Thr | Glu | Leu | Arg | Thr | Thr |
|---|---|---|---|---|---|---|---|---|---|---|---|---|---|---|---|
| | | | | 85 | | | | | 90 | | | | | 95 | |

| Asp | Trp | Tyr | Arg | His | Arg | Asp | Pro | Ala | Arg | Arg | Trp | His | Ala | Pro | Tyr |
|---|---|---|---|---|---|---|---|---|---|---|---|---|---|---|---|
| | | | 100 | | | | | 105 | | | | | 110 | | |

| Val | Lys | Asp | Lys | Ser | Glu | Glu | Ala | Arg | Tyr | Thr | Gln | Arg | Phe | Leu | Ala |
|---|---|---|---|---|---|---|---|---|---|---|---|---|---|---|---|
| | | 115 | | | | | 120 | | | | | 125 | | | |

| Ala | Tyr | Ser | Ser | Glu | Gly | Ser | Ile | Arg | Thr | Ile | Asp | Ala | Tyr | Trp | Arg |
|---|---|---|---|---|---|---|---|---|---|---|---|---|---|---|---|
| 130 | | | | | 135 | | | | | 140 | | | | | |

| Asp | Glu | Ile | Leu | Asn | Lys | Tyr | Tyr | Gly | Ala | Leu | Leu | Tyr | Asn | Glu | Tyr |
|---|---|---|---|---|---|---|---|---|---|---|---|---|---|---|---|
| 145 | | | | | 150 | | | | | 155 | | | | | 160 |

| Gly | Leu | Phe | Asn | Ala | His | Ser | Ser | Val | Gly | Arg | Asp | Cys | Leu | Ser | Asp |
|---|---|---|---|---|---|---|---|---|---|---|---|---|---|---|---|
| | | | | 165 | | | | | 170 | | | | | 175 | |

| Thr | Ile | Arg | Gln | Ser | Ala | Thr | Phe | Ala | Gly | Leu | Asp | Lys | Val | Asp | Asn |
|---|---|---|---|---|---|---|---|---|---|---|---|---|---|---|---|
| | | | 180 | | | | | 185 | | | | | 190 | | |

| Ala | Gln | Met | Ile | Gln | Met | Glu | Arg | Leu | Phe | Ile | Ala | Lys | Leu | Val | Pro |
|---|---|---|---|---|---|---|---|---|---|---|---|---|---|---|---|
| | | 195 | | | | | 200 | | | | | 205 | | | |

| Gly | Phe | Asp | Ala | Ser | Thr | Asp | Val | Pro | Lys | Lys | Ile | Trp | Thr | Thr | Asp |
|---|---|---|---|---|---|---|---|---|---|---|---|---|---|---|---|
| 210 | | | | | 215 | | | | | 220 | | | | | |

| Pro | Ile | Tyr | Ala | Gly | Ala | Arg | Gly | Ala | Val | Glu | Glu | Ile | Trp | Gln | Gly |
|---|---|---|---|---|---|---|---|---|---|---|---|---|---|---|---|
| 225 | | | | | 230 | | | | | 235 | | | | | 240 |

| Ile | Gln | Asp | Trp | Asn | Glu | Ile | Leu | Trp | Ala | Gly | His | Ala | Val | Tyr | Asp |
|---|---|---|---|---|---|---|---|---|---|---|---|---|---|---|---|
| | | | | 245 | | | | | 250 | | | | | 255 | |

| Ala | Thr | Phe | Gly | Gln | Phe | Ala | Arg | Arg | Glu | Phe | Phe | Gln | Arg | Leu | Ala |
|---|---|---|---|---|---|---|---|---|---|---|---|---|---|---|---|
| | | | 260 | | | | | 265 | | | | | 270 | | |

| Thr | Val | Tyr | Gly | Asp | Thr | Leu | Thr | Pro | Phe | Phe | Thr | Ala | Gln | Ser | Gln |
|---|---|---|---|---|---|---|---|---|---|---|---|---|---|---|---|
| | | 275 | | | | | 280 | | | | | 285 | | | |

| Thr | Tyr | Phe | Gln | Thr | Thr | Arg | Gly | Ala | Ile | Glu | Asp | Leu | Phe | Val | Tyr |
|---|---|---|---|---|---|---|---|---|---|---|---|---|---|---|---|
| | 290 | | | | | 295 | | | | | 300 | | | | |

| Cys | Leu | Ala | Asn | Asp | Pro | Glu | Phe | Gly | Ala | His | Asn | Arg | Thr | Phe | Leu |
|---|---|---|---|---|---|---|---|---|---|---|---|---|---|---|---|
| 305 | | | | | 310 | | | | | 315 | | | | | 320 |

| Asn | Ala | Trp | Thr | Glu | His | Tyr | Leu | Ala | Arg | Ser | Val | Thr | Ala | Leu | Lys |
|---|---|---|---|---|---|---|---|---|---|---|---|---|---|---|---|
| | | | | 325 | | | | | 330 | | | | | 335 | |

| Asp | Phe | Val | Gly | Ile | Tyr | Ala | Lys | Val | Glu | Lys | Val | Ala | Gly | Ala | Thr |
|---|---|---|---|---|---|---|---|---|---|---|---|---|---|---|---|
| | | | 340 | | | | | 345 | | | | | 350 | | |

| Asp | Arg | Ala | Gly | Val | Ser | Glu | Ala | Leu | Gln | Arg | Val | Phe | Gly | Asp | Trp |
|---|---|---|---|---|---|---|---|---|---|---|---|---|---|---|---|
| | | 355 | | | | | 360 | | | | | 365 | | | |

| Lys | Val | Asp | Tyr | Ala | Asp | Lys | Ile | Gly | Phe | Asn | Ile | Asp | Val | Asp | Gln |
|---|---|---|---|---|---|---|---|---|---|---|---|---|---|---|---|
| 370 | | | | | 375 | | | | | 380 | | | | | |

```
Lys Val Asp Ala Val Leu Ala Gly Phe Lys Asn
385                 390                 395

<210> SEQ ID NO 26
<211> LENGTH: 395
<212> TYPE: PRT
<213> ORGANISM: Methylocystis sp.
<220> FEATURE:
<221> NAME/KEY: VARIANT
<222> LOCATION: 163, 175, 335, 356, 386
<223> OTHER INFORMATION: Xaa = Any Amino Acid

<400> SEQUENCE: 26

Met Ser Gln Pro Gln Ser Ser Gln Val Thr Lys Arg Gly Leu Thr Asp
1               5                   10                  15

Pro Glu Arg Ala Ala Ile Ile Ala Ala Val Pro Asp His Ala Leu
            20                  25                  30

Asp Thr Gln Arg Lys Tyr His Tyr Phe Ile Gln Pro Arg Trp Lys Arg
            35                  40                  45

Leu Ser Glu Tyr Glu Gln Leu Ser Val Tyr Ala Gln Pro Asn Pro Asp
50                  55                  60

Trp Ile Ala Gly Gly Leu Asp Trp Gly Asp Trp Thr Gln Lys Phe His
65                  70                  75                  80

Gly Gly Arg Pro Ser Trp Gly Asn Glu Ser Thr Glu Leu Arg Thr Thr
                85                  90                  95

Asp Trp Tyr Arg His Arg Asp Pro Ala Arg Arg Trp His Ala Pro Tyr
                100                 105                 110

Val Lys Asp Lys Ser Glu Glu Ala Arg Tyr Thr Gln Arg Phe Leu Glu
            115                 120                 125

Ala Tyr Ser Ser Glu Gly Ser Ile Arg Thr Ile Asp Pro Tyr Trp Arg
130                 135                 140

Asp Glu Ile Leu Asn Lys Tyr Tyr Gly Ala Leu Leu Phe Asn Glu Tyr
145                 150                 155                 160

Gly Leu Xaa Asn Ala His Ser Ser Val Gly Arg Asp Cys Leu Xaa Asp
                165                 170                 175

Thr Ile Arg Gln Ser Ala Thr Phe Ala Gly Leu Asp Lys Val Asp Asn
                180                 185                 190

Ala Gln Met Ile Gln Met Glu Arg Leu Phe Ile Ala Lys Leu Val Pro
            195                 200                 205

Gly Phe Asp Ala Ser Thr Asp Val Pro Lys Lys Ile Trp Thr Ser Asp
210                 215                 220

Pro Ile Tyr Ala Gly Ala Arg Gly Ala Val Glu Glu Ile Trp Gln Gly
225                 230                 235                 240

Ile Gln Asp Trp Asn Glu Ile Leu Trp Ala Gly His Ala Val Tyr Asp
                245                 250                 255

Ala Thr Phe Gly Gln Phe Ala Arg Arg Glu Phe Phe Gln Arg Leu Ala
            260                 265                 270

Thr Val Tyr Gly Asp Thr Leu Thr Pro Phe Phe Thr Ala Gln Ser Gln
            275                 280                 285

Thr Tyr Phe Gln Ile Thr Arg Gly Ala Ile Glu Asp Leu Phe Val Tyr
290                 295                 300

Ser Leu Ala Asn Asp Pro Glu Phe Gly Ala His Asn Arg Thr Phe Leu
305                 310                 315                 320

Asn Ala Trp Thr Asp His Tyr Leu Val Arg Ser Val Ser Ala Xaa Lys
                325                 330                 335

Asp Phe Val Gly Ile Tyr Ala Lys Val Glu Lys Val Ala Gly Ala Thr
```

```
                340                 345                 350
Asp Arg Ala Xaa Val Ser Glu Ala Leu Gln Arg Val Phe Gly Asp Trp
            355                 360                 365

Lys Ile Asp Tyr Ala Glu Lys Ile Gly Phe Lys Ile Asp Val Asp Glu
370                 375                 380

Lys Xaa Asp Ala Val Leu Ala Gly Tyr Lys Asn
385                 390                 395

<210> SEQ ID NO 27
<211> LENGTH: 389
<212> TYPE: PRT
<213> ORGANISM: Methylococcus capsulatus

<400> SEQUENCE: 27

Met Ser Met Leu Gly Glu Arg Arg Gly Leu Thr Asp Pro Glu Met
1               5                   10                  15

Ala Ala Val Ile Leu Lys Ala Leu Pro Glu Ala Pro Leu Asp Gly Asn
                20                  25                  30

Asn Lys Met Gly Tyr Phe Val Thr Pro Arg Trp Lys Arg Leu Thr Glu
            35                  40                  45

Tyr Glu Ala Leu Thr Val Tyr Ala Gln Pro Asn Ala Asp Trp Ile Ala
50                  55                  60

Gly Gly Leu Asp Trp Gly Asp Trp Thr Gln Lys Phe His Gly Arg
65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
130                 135                 140

Ile Asn Arg Tyr Trp Gly Ala Phe Leu Phe Asn Glu Tyr Gly Leu Phe
145                 150                 155                 160

Asn Ala His Ser Gln Gly Ala Arg Glu Ala Leu Ser Asp Val Thr Arg
                165                 170                 175

Val Ser Leu Ala Phe Trp Gly Phe Asp Lys Ile Asp Ile Ala Gln Met
            180                 185                 190

Ile Gln Leu Glu Arg Gly Phe Leu Ala Lys Ile Val Pro Gly Phe Asp
        195                 200                 205

Glu Ser Thr Ala Val Pro Lys Ala Glu Trp Thr Asn Gly Glu Val Tyr
210                 215                 220

Lys Ser Ala Arg Leu Ala Val Glu Gly Leu Trp Gln Glu Val Phe Asp
225                 230                 235                 240

Trp Asn Glu Ser Ala Phe Ser Val His Ala Val Tyr Asp Ala Leu Phe
                245                 250                 255

Gly Gln Phe Val Arg Arg Glu Phe Gln Arg Leu Ala Pro Arg Phe
            260                 265                 270

Gly Asp Asn Leu Thr Pro Phe Phe Ile Asn Gln Ala Gln Thr Tyr Phe
        275                 280                 285

Gln Ile Ala Lys Gln Gly Val Gln Asp Leu Tyr Tyr Asn Cys Leu Gly
        290                 295                 300

Asp Asp Pro Glu Phe Ser Asp Tyr Asn Arg Thr Val Met Arg Asn Trp
305                 310                 315                 320
```

```
Thr Gly Lys Trp Leu Glu Pro Thr Ile Ala Ala Leu Arg Asp Phe Met
            325                 330                 335

Gly Leu Phe Ala Lys Leu Pro Ala Gly Thr Thr Asp Lys Glu Glu Ile
        340                 345                 350

Thr Ala Ser Leu Tyr Arg Val Val Asp Asp Trp Ile Glu Asp Tyr Ala
            355                 360                 365

Ser Arg Ile Asp Phe Lys Ala Asp Arg Asp Gln Ile Val Lys Ala Val
    370                 375                 380

Leu Ala Gly Leu Lys
385

<210> SEQ ID NO 28
<211> LENGTH: 392
<212> TYPE: PRT
<213> ORGANISM: Methylovulum miyakonense

<400> SEQUENCE: 28

Met Ser Ile Glu Val Ser Gly Gly Arg Gly Leu Thr Asp Pro Ala
1               5                   10                  15

Leu Ala Ala Thr Ile Leu Ala Ala Ile Pro Asp Gln Pro Leu Glu Thr
            20                  25                  30

Gln Arg Lys Met Asn Tyr Phe Met Thr Pro Arg Gly Lys Arg Ile Asn
        35                  40                  45

Glu Tyr Glu Val Leu Cys Cys Tyr Thr Gln Pro Thr Pro Asp Trp Ile
50                  55                  60

Pro Gly Gly Leu Asp Trp Gly Asp Trp Thr Gln Lys Phe His Gly Gly
65                  70                  75                  80

Arg Pro Ser Trp Ser Asn Glu Ser Thr Glu Met Arg Ser Pro Asp Trp
                85                  90                  95

Leu Lys His Arg Asp Pro Ala Phe Arg Trp His Ala Leu Tyr Val Lys
            100                 105                 110

Asp Lys Ala Glu Glu Trp Arg Tyr Thr Asp Arg Phe Leu Lys Ala Tyr
        115                 120                 125

Ser Ala Asp Gly His Val Arg Ser Met Asp Pro Ile Trp Arg Asp Glu
    130                 135                 140

Val Leu Gly Asp Tyr Leu Gly Ala Phe Gly Phe Ser Glu Tyr Gly Leu
145                 150                 155                 160

Phe Asn Ala His Ser Ser Val Val Arg Asp Cys Leu Gly Asp Thr Leu
                165                 170                 175

Arg Met Ser Ser Ala Met Ile Gly Leu Asp Lys Val Asp Asn Ala Gln
            180                 185                 190

Met Ile Gln Met Glu Arg Thr Phe Leu Ala Lys Leu Val Pro Gly Phe
        195                 200                 205

Pro Glu Ser Thr Asp Ile Pro Lys Asn Glu Trp Thr Lys Gly Thr Ile
    210                 215                 220

Phe Lys Gly Ser Arg Glu Val Val Gln Gln Ile Trp Gln Glu Thr Tyr
225                 230                 235                 240

Asp Trp Asn Glu Ile Leu Phe Ser Gly His Met Ile Tyr Asp Pro Leu
                245                 250                 255

Phe Gly Gln Phe Val Arg Arg Glu Phe Phe Ser Arg Leu Ser Ser Tyr
            260                 265                 270

Tyr Gly Asp Thr Leu Thr Pro Phe Phe Ile Asn Gln Met Gln Leu Tyr
        275                 280                 285

Phe Ser Gln Thr Lys Gly Ile Thr Thr Asp Met Phe His Thr Cys Leu
    290                 295                 300
```

```
Ala Ala Asp Gly Gln Phe Gly Ala Tyr Asn Thr Arg Leu Met His Val
305                 310                 315                 320

Trp Ala Asn Lys Trp Leu Pro Arg Thr Ile Thr Ala Leu Lys Gly Phe
                325                 330                 335

Met Gly Ile Phe Ser Lys Ile Pro Glu Ile Lys Gly Val Thr Asp Lys
            340                 345                 350

Pro Ala Ile Glu Ala Ala Leu Asn Arg Val Phe Asp Asp Trp Lys His
        355                 360                 365

Asp Phe Ala Asp Pro Ile Gly Tyr Lys Ala Asp Thr Ala Ala Leu Ile
    370                 375                 380

Lys Thr Val Leu Thr Gly Leu Lys
385                 390

<210> SEQ ID NO 29
<211> LENGTH: 395
<212> TYPE: PRT
<213> ORGANISM: Methylosinus trichosporium

<400> SEQUENCE: 29

Met Ser Gln Pro Gln Ser Ser Gln Val Thr Lys Arg Gly Leu Thr Asp
1               5                   10                  15

Pro Glu Arg Ala Ala Ile Ile Ala Ala Val Pro Asp His Ala Leu
            20                  25                  30

Asp Thr Gln Arg Lys Tyr His Tyr Phe Ile Gln Pro Arg Trp Lys Arg
        35                  40                  45

Leu Ser Glu Tyr Glu Gln Leu Ser Cys Tyr Ala Gln Pro Asn Pro Asp
50                  55                  60

Trp Ile Ala Gly Gly Leu Asp Trp Gly Asp Trp Thr Gln Lys Phe His
65                  70                  75                  80

Gly Gly Arg Pro Ser Trp Gly Asn Glu Ser Thr Glu Leu Arg Thr Thr
                85                  90                  95

Asp Trp Phe Arg His Arg Asp Pro Ala Arg Arg Trp His His Pro Tyr
            100                 105                 110

Val Lys Asp Lys Ser Glu Glu Ala Arg Tyr Thr Gln Arg Phe Leu Ala
        115                 120                 125

Gly Tyr Ala Ser Glu Gly Ser Ile Arg Thr Ile Asp Pro Tyr Trp Arg
    130                 135                 140

Asp Glu Ile Leu Asn Lys Tyr Tyr Gly Ala Leu Ile Tyr Ser Glu Tyr
145                 150                 155                 160

Gly Leu Phe Asn Ser His Ser Ser Val Gly Arg Asp Cys Leu Ser Asp
                165                 170                 175

Thr Ile Arg Gln Ser Ala Val Phe Ala Ala Leu Asp Lys Val Asp Asn
            180                 185                 190

Ala Gln Met Ile Gln Met Glu Arg Leu Phe Ile Ala Lys Leu Val Pro
        195                 200                 205

Gly Phe Asp Ala Ser Thr Asp Val Pro Lys Lys Val Trp Thr Thr Asp
    210                 215                 220

Pro Ile Tyr Ala Gly Ala Arg Gly Thr Val Gln Ala Ile Trp Gln Gly
225                 230                 235                 240

Ile Gln Asp Trp Asn Glu Ile Leu Trp Ala Gly His Ala Val Tyr Asp
                245                 250                 255

Ala Thr Phe Gly Gln Phe Ala Arg Arg Glu Phe Phe Gln Arg Leu Ala
            260                 265                 270

Thr Val Tyr Gly Asp Thr Leu Thr Pro Phe Phe Thr Ala Gln Ser Gln
```

```
                275                 280                 285
Thr Tyr Phe Gln Thr Thr Arg Gly Ala Ile Asp Asp Leu Phe Val Tyr
    290                 295                 300

Cys Leu Ala Asn Asp Ser Glu Phe Gly Ala His Asn Arg Thr Phe Leu
305                 310                 315                 320

Asn Ala Trp Thr Glu His Tyr Leu Ala Ser Val Ala Ala Leu Lys
                325                 330                 335

Asp Phe Val Gly Leu Tyr Ala Lys Val Glu Lys Val Ala Gly Ala Thr
                340                 345                 350

Asp Arg Ala Gly Val Ser Glu Ala Leu Gln Arg Val Phe Gly Asp Trp
                355                 360                 365

Lys Val Asp Tyr Ala Asp Lys Ile Gly Phe Lys Val Asp Val Asp Gln
                370                 375                 380

Lys Val Asp Ala Val Leu Ala Gly Tyr Lys Asn
385                 390                 395

<210> SEQ ID NO 30
<211> LENGTH: 395
<212> TYPE: PRT
<213> ORGANISM: Methylocystis sp.

<400> SEQUENCE: 30

Met Ser Gln Pro Gln Ser Ser Gln Val Thr Lys Arg Gly Leu Thr Asp
1               5                   10                  15

Pro Glu Arg Ala Ala Ile Ile Ala Ala Val Pro Asp His Ala Leu
                20                  25                  30

Asp Thr Gln Arg Lys Tyr His Tyr Phe Ile Gln Pro Arg Trp Lys Arg
                35                  40                  45

Leu Ser Glu Tyr Glu Gln Leu Ser Cys Tyr Ala Gln Pro Asn Pro Asp
50                  55                  60

Trp Ile Ala Gly Gly Leu Asp Trp Gly Asp Trp Thr Gln Lys Phe His
65                  70                  75                  80

Gly Gly Arg Pro Ser Trp Gly Asn Glu Ser Thr Glu Leu Arg Thr Thr
                85                  90                  95

Asp Trp Tyr Arg His Arg Asp Pro Ala Arg Arg Trp His Ala Pro Tyr
                100                 105                 110

Val Lys Asp Lys Ser Glu Glu Ala Arg Tyr Thr Gln Arg Phe Leu Ala
                115                 120                 125

Ala Tyr Ser Ser Glu Gly Ser Ile Arg Thr Ile Asp Pro Tyr Trp Arg
130                 135                 140

Asp Glu Ile Leu Asn Lys Tyr Tyr Gly Ala Leu Leu Tyr Asn Glu Tyr
145                 150                 155                 160

Gly Leu Phe Asn Ala His Ser Ser Val Gly Arg Asp Cys Leu Ser Asp
                165                 170                 175

Thr Ile Arg Gln Ser Ala Thr Phe Ala Gly Leu Asp Lys Val Asp Asn
                180                 185                 190

Ala Gln Met Ile Gln Met Glu Arg Leu Phe Ile Ala Lys Leu Val Pro
                195                 200                 205

Gly Phe Asp Ala Ser Thr Asp Val Pro Lys Lys Ile Trp Thr Ser Asp
                210                 215                 220

Pro Ile Tyr Ala Gly Ala Arg Gly Ala Val Glu Glu Ile Trp Gln Gly
225                 230                 235                 240

Ile Gln Asp Trp Asn Glu Ile Leu Trp Ala Gly His Ala Val Tyr Asp
                245                 250                 255
```

```
Ala Thr Phe Gly Gln Phe Ala Arg Arg Glu Phe Phe Gln Arg Leu Ala
            260                 265                 270

Thr Val Tyr Gly Asp Thr Leu Thr Pro Phe Phe Thr Ala Gln Ser Gln
            275                 280                 285

Thr Tyr Phe Gln Thr Thr Arg Gly Ala Ile Asp Asp Leu Phe Val Tyr
            290                 295                 300

Cys Leu Ala Asn Asp Pro Glu Phe Gly Ala His Asn Arg Thr Phe Leu
305                 310                 315                 320

Asn Ala Trp Thr Glu His Tyr Leu Ala Arg Ser Val Thr Ala Leu Lys
                325                 330                 335

Asp Phe Val Gly Ile Tyr Ala Lys Val Glu Lys Val Ala Gly Ala Thr
            340                 345                 350

Asp Arg Ala Gly Val Ser Glu Ala Leu Gln Arg Val Phe Gly Asp Trp
            355                 360                 365

Lys Val Asp Tyr Ala Asp Lys Ile Gly Phe Lys Ile Asp Val Asp Glu
            370                 375                 380

Lys Val Ala Ala Val Leu Ala Gly Tyr Lys Asn
385                 390                 395

<210> SEQ ID NO 31
<211> LENGTH: 138
<212> TYPE: PRT
<213> ORGANISM: Methylosinus sporium

<400> SEQUENCE: 31

Met Ser Ser Ala His Asn Ala Tyr Asn Ala Gly Ile Met Gln Lys Thr
1               5                   10                  15

Gly Lys Ala Phe Ala Asp Glu Phe Phe Ala Glu Glu Asn Gln Val Val
            20                  25                  30

His Glu Ser Asn Ala Val Val Leu Val Leu Met Lys Ser Asp Glu Ile
            35                  40                  45

Asp Ala Ile Ile Glu Asp Met Val Leu Lys Gly Gly Lys Ala Lys Asn
        50                  55                  60

Pro Ser Ile Val Val Glu Asp Lys Ala Gly Phe Trp Trp Ile Lys Ala
65                  70                  75                  80

Asp Gly Ala Ile Glu Ile Asp Ala Ala Glu Ala Ser Asp Leu Leu Gly
                85                  90                  95

Lys Pro Phe Ser Val Tyr Asp Leu Leu Val Asn Val Ser Ser Thr Val
            100                 105                 110

Gly Arg Ala Tyr Thr Leu Gly Thr Lys Phe Thr Ile Thr Ser Glu Leu
            115                 120                 125

Met Gly Leu Asp Arg Ala Leu Thr Asp Ile
            130                 135

<210> SEQ ID NO 32
<211> LENGTH: 138
<212> TYPE: PRT
<213> ORGANISM: Methylocystis sp.
<220> FEATURE:
<221> NAME/KEY: VARIANT
<222> LOCATION: 29, 60
<223> OTHER INFORMATION: Xaa = Any Amino Acid

<400> SEQUENCE: 32

Met Thr Ser Ala His Asn Ala Tyr Asn Ala Gly Ile Met Gln Lys Thr
1               5                   10                  15

Gly Lys Ala Phe Ala Asp Glu Phe Phe Ala Glu Glu Xaa Gln Val Val
            20                  25                  30
```

His Glu Ser Asn Ala Val Val Leu Val Leu Met Lys Ser Asp Glu Ile
             35                  40                  45

Asp Ala Ile Ile Glu Asp Ile Val Leu Lys Gly Xaa Lys Ala Lys Asn
 50                  55                  60

Pro Ser Ile Val Val Glu Asp Lys Ala Gly Phe Trp Trp Ile Lys Ala
 65                  70                  75                  80

Asp Gly Ala Ile Glu Ile Asp Ala Ala Glu Ala Ser Asp Leu Leu Gly
                 85                  90                  95

Lys Pro Phe Ser Val Tyr Asp Leu Leu Val Asn Val Ser Ser Thr Val
             100                 105                 110

Gly Arg Ala Tyr Thr Leu Gly Thr Lys Phe Thr Ile Thr Ser Glu Leu
             115                 120                 125

Met Gly Leu Asp Arg Ala Leu Thr Asp Ile
             130                 135

<210> SEQ ID NO 33
<211> LENGTH: 141
<212> TYPE: PRT
<213> ORGANISM: Methylomonas sp.

<400> SEQUENCE: 33

Met Ser Lys Ser Ser Asn Ala Tyr Asn Ala Gly Ile Met Gln Lys Thr
 1               5                  10                  15

Gly Lys Ala Phe Ala Asp Glu Tyr Phe Ala Glu Asp Asn Gln Val Val
                 20                  25                  30

His Glu Ser His Glu Val Val Leu Val Leu Lys Lys Ser Asp Glu Leu
             35                  40                  45

Asn Thr Val Val Glu Glu Ile Leu Gln Gly Ser His Lys Ala Asp Asn
 50                  55                  60

Pro Thr Leu Val Val Glu Asp Arg Ala Gly Phe Trp Trp Leu Lys Ala
 65                  70                  75                  80

Thr Gly Lys Ile Glu Ile Asp Cys Val Glu Val Ser Glu Leu Leu Gly
                 85                  90                  95

Lys His Tyr Ser Val Tyr Asp Leu Leu Val Asp Val Ser Ser Thr Ile
             100                 105                 110

Gly Arg Ala Tyr Thr Leu Gly Glu Thr Phe Thr Ile Thr Ser Glu Leu
             115                 120                 125

Met Gly Leu Asp Val Lys Leu Lys Asp Leu Ala Ala Ala
             130                 135                 140

<210> SEQ ID NO 34
<211> LENGTH: 141
<212> TYPE: PRT
<213> ORGANISM: Methylococcus capsulatus

<400> SEQUENCE: 34

Met Ser Val Asn Ser Asn Ala Tyr Asp Ala Gly Ile Met Gly Leu Lys
 1               5                  10                  15

Gly Lys Asp Phe Ala Asp Gln Phe Phe Ala Asp Glu Asn Gln Val Val
                 20                  25                  30

His Glu Ser Asp Thr Val Val Leu Val Leu Lys Lys Ser Asp Glu Ile
             35                  40                  45

Asn Thr Phe Ile Glu Glu Ile Leu Leu Thr Asp Tyr Lys Lys Asn Val
 50                  55                  60

Asn Pro Thr Val Asn Val Glu Asp Arg Ala Gly Tyr Trp Trp Ile Lys
 65                  70                  75                  80

```
Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp Tyr His Ala
    130                 135                 140

<210> SEQ ID NO 35
<211> LENGTH: 141
<212> TYPE: PRT
<213> ORGANISM: Methylomicrobium japanense

<400> SEQUENCE: 35

Met Ser Leu Ser Ser Asn Ala Tyr Gly Ala Gly Ile Met Ala Lys Ser
1               5                   10                  15

Gly Lys Glu Phe Ala Asp Glu Tyr Phe Ala Glu Asn Gln Val Val
            20                  25                  30

His Glu Ser Asn Glu Val Val Leu Val Leu Lys Lys Ser Asp Glu Ile
            35                  40                  45

Asn Ile Ile Val Asp Glu Ile Leu Leu Gly Asp Arg Lys Asp Glu Asn
        50                  55                  60

Pro Thr Leu Val Val Glu Asp Arg Ala Gly Tyr Trp Trp Leu Lys Ala
65                  70                  75                  80

Thr Gly Lys Ile Glu Val Asp Cys Glu Glu Val Ser Glu Leu Leu Gly
                85                  90                  95

Arg Thr Phe Ser Val Tyr Asp Phe Leu Val Asp Val Ser Ser Thr Ile
            100                 105                 110

Gly Arg Ala Phe Thr Leu Gly Glu Lys Phe Thr Ile Thr Ser Glu Leu
        115                 120                 125

Met Gly Leu Asp Arg Lys Leu Glu Asp Leu Lys Ala Ala
    130                 135                 140

<210> SEQ ID NO 36
<211> LENGTH: 141
<212> TYPE: PRT
<213> ORGANISM: Methylococcus capsulatus

<400> SEQUENCE: 36

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Val Leu Val Leu Lys Lys Ser Asp Glu Ile
            35                  40                  45

Asn Thr Phe Ile Glu Glu Ile Leu Leu Thr Asp Tyr Lys Lys Asn Val
        50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125
```

```
Leu Met Gly Leu Asp Arg Lys Leu Glu Asp Tyr His Ala
        130                 135                 140

<210> SEQ ID NO 37
<211> LENGTH: 141
<212> TYPE: PRT
<213> ORGANISM: Methylovulum miyakonense

<400> SEQUENCE: 37

Met Thr Thr Ser Ser Asn Ala Tyr Gly Ala Gly Ile Met Ala Lys Thr
1               5                   10                  15

Gly Lys Ala Phe Ala Asp Glu Tyr Phe Ser Glu Glu Asn Gln Thr Val
            20                  25                  30

His Glu Ser Asn Glu Val Val Leu Val Leu Lys Lys Ser Asp Glu Ile
        35                  40                  45

Asn Ser Val Val His Glu Ile Leu Leu Gly Asp Arg Lys Ala Asp Asn
    50                  55                  60

Pro Thr Leu Ile Val Glu Asp Arg Ala Gly Tyr Trp Trp Leu Lys Ala
65                  70                  75                  80

Thr Gly Lys Ile Glu Ile Asp Cys Thr Glu Val Ser Glu Leu Leu Gly
                85                  90                  95

Lys His Phe Ser Val Tyr Asp Leu Leu Val Asp Val Ser Ser Thr Ile
            100                 105                 110

Gly Arg Ala Tyr Thr Leu Gly Glu Thr Phe Thr Ile Thr Ser Glu Leu
        115                 120                 125

Met Gly Leu Asp Val Lys Leu Gln Asp Leu Gln Thr Ala
    130                 135                 140

<210> SEQ ID NO 38
<211> LENGTH: 138
<212> TYPE: PRT
<213> ORGANISM: Methylosinus trichosporium

<400> SEQUENCE: 38

Met Thr Ser Ala His Asn Ala Tyr Asn Ala Gly Ile Met Gln Lys Thr
1               5                   10                  15

Gly Lys Ala Phe Ala Asp Glu Phe Phe Ala Glu Glu Asn Gln Val Val
            20                  25                  30

His Glu Ser Asn Ala Val Val Leu Val Leu Met Lys Ser Asp Glu Ile
        35                  40                  45

Asp Ala Ile Ile Glu Asp Ile Val Leu Lys Gly Gly Lys Ala Lys Asn
    50                  55                  60

Pro Ser Ile Val Val Glu Asp Lys Ala Gly Phe Trp Trp Ile Lys Ala
65                  70                  75                  80

Asp Gly Ala Ile Glu Ile Asp Ala Ala Glu Ala Gly Glu Leu Leu Gly
                85                  90                  95

Lys Pro Phe Ser Val Tyr Asp Leu Leu Ile Asn Val Ser Ser Thr Val
            100                 105                 110

Gly Arg Ala Tyr Thr Leu Gly Thr Lys Phe Thr Ile Thr Ser Glu Leu
        115                 120                 125

Met Gly Leu Asp Arg Ala Leu Thr Asp Ile
    130                 135

<210> SEQ ID NO 39
<211> LENGTH: 169
<212> TYPE: PRT
<213> ORGANISM: Methylosinus sporium
```

<400> SEQUENCE: 39

```
Met Ala Lys Arg Glu Pro Ile His Glu Asn Ser Thr Arg Thr Glu Trp
1               5                   10                  15

Glu Gly Lys Ile Ala Lys Leu Asn Ser Val Asp Gln Ala Thr Lys Phe
            20                  25                  30

Ile Gln Asp Phe Arg Val Ala Tyr Ser Ser Pro Phe Arg Lys Ser Tyr
        35                  40                  45

Asp Leu Asp Val Asp Tyr Gln Tyr Ile Glu Arg Lys Ile Glu Glu Arg
    50                  55                  60

Leu Ser Val Leu Lys Thr Glu Lys Leu Ser Val Ala Asp Leu Val Thr
65                  70                  75                  80

Lys Ala Thr Thr Gly Glu Asp Ala Ala Val Glu Ala Ala Trp Ile
                85                  90                  95

Ala Lys Met Lys Ala Ala Glu Ser Lys Tyr Ala Ala Glu Arg Ile His
                100                 105                 110

Ile Glu Phe Arg Gln Leu Tyr Lys Pro Pro Val Leu Pro Val Asn Val
            115                 120                 125

Phe Leu Arg Thr Asp Ala Ala Leu Gly Thr Ile Leu Met Glu Leu Arg
130                 135                 140

Asn Thr Asp Tyr Tyr Ala Thr Pro Leu Glu Gly Leu Arg Lys Glu Arg
145                 150                 155                 160

Gly Val Lys Val Leu His Leu Gln Ala
                165
```

<210> SEQ ID NO 40
<211> LENGTH: 169
<212> TYPE: PRT
<213> ORGANISM: Methylocystis sp.
<220> FEATURE:
<221> NAME/KEY: VARIANT
<222> LOCATION: 11
<223> OTHER INFORMATION: Xaa = Any Amino Acid

<400> SEQUENCE: 40

```
Met Gly Lys Arg Glu Pro Ile His Asp Asn Xaa Thr Arg Ala Glu Trp
1               5                   10                  15

Glu Ala Lys Ile Gln Lys Leu Asn Ser Val Asp Gln Ala Thr Lys Phe
            20                  25                  30

Ile Gln Asp Phe Arg Val Asn Tyr Ser Ser Pro Phe Arg Lys Ser Tyr
        35                  40                  45

Asp Leu Asp Val Asp Tyr Gln Tyr Ile Glu Arg Lys Ile Glu Glu Arg
    50                  55                  60

Leu Ser Val Leu Lys Thr Glu Lys Leu Ser Val Ala Glu Leu Met Thr
65                  70                  75                  80

Lys Ala Thr Thr Gly Glu Asp Ala Ala Val Glu Ala Ala Trp Ile
                85                  90                  95

Ala Lys Met Gln Ser Ala Lys Ser Lys Tyr Glu Ala Glu Arg Ile His
                100                 105                 110

Ile Glu Phe Arg Gln Leu Tyr Lys Pro Pro Val Leu Pro Val Asn Val
            115                 120                 125

Phe Leu Arg Thr Asp Ala Ala Leu Gly Thr Ile Leu Met Glu Leu Arg
130                 135                 140

Asn Thr Asp Tyr Tyr Ala Thr Pro Leu Glu Gly Leu Arg Lys Glu Arg
145                 150                 155                 160

Gly Val Lys Val Leu His Leu Gln Ala
```

<210> SEQ ID NO 41
<211> LENGTH: 170
<212> TYPE: PRT
<213> ORGANISM: Methylococcus capsulatus

<400> SEQUENCE: 41

Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
    50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
                85                  90                  95

Lys Met Asn Ala Ala Lys Asp Lys Trp Glu Ala Glu Lys Ile His Ile
            100                 105                 110

Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
    130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro His
                165                 170

<210> SEQ ID NO 42
<211> LENGTH: 170
<212> TYPE: PRT
<213> ORGANISM: Methylococcus capsulatus

<400> SEQUENCE: 42

Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
    50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
                85                  90                  95

Lys Met Asn Ala Ala Lys Asp Lys Trp Glu Ala Glu Lys Ile His Ile
            100                 105                 110

Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
    130                 135                 140

Leu Asn Tyr Tyr Asp Thr Pro Leu Glu Glu Leu Arg Lys Gln Arg Gly

Val Arg Val Val His Leu Gln Ser Pro His
145                 150                 155                 160

<210> SEQ ID NO 43
<211> LENGTH: 169
<212> TYPE: PRT
<213> ORGANISM: Methylococcus capsulatus

<400> SEQUENCE: 43

Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
            85                  90                  95

Lys Met Asn Ala Ala Lys Asp Lys Trp Glu Ala Glu Lys Ile His Ile
        100                 105                 110

Gly Phe Arg Gln Ala Tyr Lys Pro Pro Ile Met Pro Val Asn Tyr Phe
    115                 120                 125

Leu Asp Gly Glu Arg Gln Leu Gly Thr Arg Leu Met Glu Leu Arg Asn
130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro
                165

<210> SEQ ID NO 44
<211> LENGTH: 165
<212> TYPE: PRT
<213> ORGANISM: Methylovulum miyakonense

<400> SEQUENCE: 44

Met Pro Asn Ile His Asp Asn Pro Lys Arg Ala Glu Trp Ala Asn Lys
1               5                   10                  15

Ile Ala Gly Leu Lys Thr Leu Ala Gln Gly His Ala Phe Leu Lys Asp
            20                  25                  30

Phe Arg Ala Gln His Val Ser Val Phe Lys Thr Asp Phe Ser Leu Glu
        35                  40                  45

Leu Asp Trp Leu Trp Ile Glu Leu Lys Ile Glu Glu Lys Val Ala Val
50                  55                  60

Leu Lys Gln Ala Glu Phe Ser Asp His Gln Leu Leu Asn Val Cys Thr
65                  70                  75                  80

Cys Gly Thr Asp Ala Gln Lys Val Ala Asn Asp Ala Leu Ala Ala Met
            85                  90                  95

Ala Ala Cys Glu Asp Met Tyr Glu Ala Glu Arg Ile His Ile Asn Phe
        100                 105                 110

Arg Leu Ala Cys Lys Pro Pro Val Met Pro Val Asn Val Phe Leu Asp
    115                 120                 125

Thr Asp Arg Gln Leu Gly Thr Lys Leu Met Glu Leu Arg Asn Thr Asp

```
                130                 135                 140
Tyr Tyr Ala Leu Pro Leu Glu Glu Leu Arg Lys Ala Arg Gly Val Arg
145                 150                 155                 160

Val Val Thr Leu Gln
            165
```

<210> SEQ ID NO 45
<211> LENGTH: 169
<212> TYPE: PRT
<213> ORGANISM: Methylosinus trichosporium

<400> SEQUENCE: 45

```
Met Ala Lys Arg Glu Pro Ile His Asp Asn Ser Thr Arg Thr Glu Trp
1               5                   10                  15

Glu Ala Lys Ile Ala Lys Leu Thr Ser Val Asp Gln Ala Thr Lys Phe
            20                  25                  30

Ile Gln Asp Phe Arg Val Ala Tyr Thr Ser Pro Phe Arg Lys Ser Tyr
        35                  40                  45

Asp Ile Asp Val Asp Tyr Gln Tyr Ile Glu Arg Lys Ile Glu Glu Lys
    50                  55                  60

Leu Ser Val Leu Lys Thr Glu Lys Leu Pro Val Ala Asp Leu Ile Thr
65                  70                  75                  80

Lys Ala Ser Thr Gly Glu Asp Ala Ala Val Glu Ala Ala Trp Ile
                85                  90                  95

Ala Lys Ile Lys Ala Ala Lys Thr Lys Tyr Glu Ala Glu Arg Val His
            100                 105                 110

Ile Glu Phe Arg Gln Leu Tyr Lys Pro Pro Val Leu Pro Val Asn Val
        115                 120                 125

Phe Leu Arg Thr Asp Ala Ala Leu Gly Thr Val Leu Met Glu Ile Arg
    130                 135                 140

Asn Thr Asp Tyr Tyr Ala Thr Pro Leu Glu Gly Leu Arg Lys Glu Arg
145                 150                 155                 160

Gly Val Lys Val Leu His Leu Gln Ala
                165
```

<210> SEQ ID NO 46
<211> LENGTH: 343
<212> TYPE: PRT
<213> ORGANISM: Methylosinus sporium

<400> SEQUENCE: 46

```
Met Tyr Gln Ile Val Ile Glu Thr Glu Asp Gly Glu Thr Cys Ser Phe
1               5                   10                  15

Glu Cys Gly Pro Ser Glu Asp Val Ile Ser Ala Gly Leu Arg Gln Ser
            20                  25                  30

Val Ile Leu Leu Ala Ser Cys Arg Ala Gly Gly Cys Ala Thr Cys Lys
        35                  40                  45

Ala Asp Cys Thr Asp Gly Glu Tyr Glu Leu Ile Asp Val Lys Val Gln
    50                  55                  60

Ala Leu Pro Pro Asp Glu Glu Asp Gly Lys Val Leu Leu Cys Arg
65                  70                  75                  80

Thr Phe Pro Arg Ser Asp Leu His Leu Ile Val Pro Tyr Thr Tyr Asp
                85                  90                  95

Arg Ile Ser Phe Glu Ala Ile Gln Thr Asn Trp Leu Ala Glu Ile Val
            100                 105                 110

Glu Cys Asp Arg Val Ser Ser Asn Val Val Arg Leu Leu Leu Gln Pro
```

```
            115                 120                 125
Leu Thr Ala Asp Gly Ala Ala Pro Ile Ser Leu Asn Phe Ala Pro Gly
        130                 135                 140

Gln Phe Val Asp Ile Glu Ile Pro Gly Thr His Thr Arg Arg Ser Tyr
145                 150                 155                 160

Ser Met Ala Ser Val Ala Glu Asp Gly Arg Leu Glu Phe Phe Ile Arg
                165                 170                 175

Leu Leu Pro Asp Gly Ala Phe Ser Asn Tyr Leu Arg Thr Gln Ala Ser
            180                 185                 190

Val Gly Gln Arg Val Ala Leu Arg Gly Pro Ala Gly Ser Phe Phe Leu
        195                 200                 205

His Lys Ser Glu Arg Pro Arg Phe Phe Val Ala Gly Thr Gly Leu
    210                 215                 220

Ser Pro Val Leu Ser Met Ile Arg Gln Leu Lys Lys Glu Ala Asp Pro
225                 230                 235                 240

Gln Pro Ala Thr Leu Phe Phe Gly Val Thr Asn Tyr Glu Glu Leu Phe
                245                 250                 255

Tyr Val Glu Glu Leu Arg Ala Leu Gln Lys Ala Met Pro Ser Leu Asp
            260                 265                 270

Val Gln Val Ala Val Asn Ala Thr Glu Ala Asn Gly Val Ala Lys
        275                 280                 285

Gly Thr Val Ile Asp Leu Met Arg Ala Glu Leu Glu Lys Leu Arg Gly
    290                 295                 300

Ala Pro Asp Ile Tyr Leu Cys Gly Pro Pro Gly Met Ile Glu Ala Ala
305                 310                 315                 320

Phe Asp Ala Ala Ala Thr Ala Gly Val Pro Lys Glu Gln Val Tyr Leu
                325                 330                 335

Glu Lys Phe Leu Ala Ser Gly
            340

<210> SEQ ID NO 47
<211> LENGTH: 333
<212> TYPE: PRT
<213> ORGANISM: Methylocystis sp.
<220> FEATURE:
<221> NAME/KEY: VARIANT
<222> LOCATION: 231
<223> OTHER INFORMATION: Xaa = Any Amino Acid

<400> SEQUENCE: 47

Met Tyr Gln Ile Val Ile Glu Thr Asp Gly Glu Thr Cys Ser Phe
1               5                   10                  15

Glu Cys Gly Pro Ser Glu Asp Val Ile Ser Ala Gly Leu Arg Gln Ser
                20                  25                  30

Val Ile Leu Leu Ala Ser Cys Arg Ala Gly Gly Cys Ala Thr Cys Lys
            35                  40                  45

Ala Asp Cys Thr Asp Gly Asp Tyr Glu Leu Ile Asp Val Lys Val Gln
        50                  55                  60

Ala Leu Pro Pro Asp Glu Glu Asp Gly Lys Val Leu Leu Cys Arg
65                  70                  75                  80

Thr Phe Pro Arg Ser Asp Leu His Ile Val Pro Tyr Thr Tyr Asp
                85                  90                  95

Arg Ile Ser Phe Gln Ala Ile Gln Thr Asn Trp Leu Ala Glu Ile Thr
            100                 105                 110

Glu Cys Asp Arg Val Ser Ser Asn Val Val Arg Leu Val Leu Gln Pro
        115                 120                 125
```

```
Leu Thr Ala Asp Gly Ala Ala Pro Ile Ser Leu Asn Phe Met Pro Gly
            130                 135                 140

Gln Phe Val Asp Ile Glu Ile Pro Gly Thr His Thr Arg Arg Ser Tyr
145                 150                 155                 160

Ser Met Ala Ser Val Ala Glu Asp Gly Ser Leu Glu Phe Phe Ile Arg
                165                 170                 175

Leu Leu Pro Asp Gly Ala Phe Ser Asn Tyr Leu Arg Ser Gln Ala Arg
            180                 185                 190

Val Gly Gln Arg Val Ala Leu Arg Gly Pro Ala Gly Ser Phe Ser Leu
        195                 200                 205

His Lys Ser Glu Arg Pro Arg Phe Phe Val Ala Gly Thr Gly Leu
    210                 215                 220

Ser Pro Val Leu Ser Met Xaa Arg Gln Leu Lys Lys Glu Ser Asp Pro
225                 230                 235                 240

Leu Pro Ala Thr Leu Phe Phe Gly Val Thr Asn Tyr Asp Glu Leu Phe
                245                 250                 255

Tyr Val Glu Glu Leu Lys Ala Leu Gln His Ala Met Pro Ser Leu Asp
            260                 265                 270

Val Gln Ile Ala Val Val Asn Val Ser Glu Gly Asn Gly Val Ala Lys
        275                 280                 285

Gly Thr Val Ile Asp Leu Leu Gln Asp Glu Leu Gly Arg Arg Ala Glu
    290                 295                 300

Lys Pro Asp Ile Tyr Leu Cys Gly Pro Pro Gly Met Ile Asp Ala Ala
305                 310                 315                 320

Phe Ala Ala Ala Ser Ser Ala Gly Val Pro Lys Glu Gln
                325                 330

<210> SEQ ID NO 48
<211> LENGTH: 340
<212> TYPE: PRT
<213> ORGANISM: Methylosinus trichosporium

<400> SEQUENCE: 48

Met Tyr Gln Ile Val Ile Glu Thr Glu Asp Gly Glu Thr Cys Arg Arg
1               5                   10                  15

Met Arg Pro Ser Glu Asp Trp Ile Ser Arg Ala Glu Ala Glu Arg Asn
            20                  25                  30

Leu Leu Ala Ser Cys Arg Ala Gly Cys Ala Thr Cys Lys Ala Asp Cys
        35                  40                  45

Thr Asp Gly Asp Tyr Glu Leu Ile Asp Val Lys Val Gln Ala Val Pro
    50                  55                  60

Pro Asp Glu Glu Glu Asp Gly Lys Val Leu Leu Cys Arg Thr Phe Pro
65                  70                  75                  80

Arg Ser Asp Leu His Leu Leu Val Pro Tyr Thr Tyr Asp Arg Ile Ser
                85                  90                  95

Phe Glu Ala Ile Gln Thr Asn Trp Leu Ala Glu Ile Leu Ala Cys Asp
            100                 105                 110

Arg Val Ser Ser Asn Val Val Arg Leu Val Leu Gln Arg Ser Arg Pro
        115                 120                 125

Met Ala Ala Arg Ile Ser Leu Asn Phe Val Pro Gly Gln Phe Val Asp
    130                 135                 140

Ile Glu Ile Pro Gly Thr His Thr Arg Arg Ser Tyr Ser Met Ala Ser
145                 150                 155                 160

Val Ala Glu Asp Gly Gln Leu Glu Phe Ile Ile Arg Leu Leu Pro Asp
```

```
                    165                 170                 175
Gly Ala Phe Ser Lys Phe Leu Gln Thr Glu Ala Lys Val Gly Met Arg
                180                 185                 190

Val Asp Leu Arg Gly Pro Ala Gly Ser Phe Phe Leu His Asp His Gly
            195                 200                 205

Gly Arg Ser Arg Val Phe Val Ala Gly Gly Thr Gly Leu Ser Pro Val
        210                 215                 220

Leu Ser Met Ile Arg Gln Leu Gly Lys Ala Ser Asp Pro Ser Pro Ala
225                 230                 235                 240

Thr Leu Leu Phe Gly Val Thr Asn Arg Glu Glu Leu Phe Tyr Val Asp
                245                 250                 255

Glu Leu Lys Thr Leu Ala Gln Ser Met Pro Thr Leu Gly Val Arg Ile
            260                 265                 270

Ala Val Val Asn Asp Asp Gly Gly Asn Gly Val Asp Lys Gly Thr Val
        275                 280                 285

Ile Asp Leu Leu Arg Ala Glu Leu Glu Ile Asp Leu Leu Gly His
290                 295                 300

Ala Arg Arg Arg Arg Arg Glu Thr Ala Arg Ser Cys Arg Glu Asp
305                 310                 315                 320

His Arg Asp Arg Cys Pro Ala Trp Arg Ser Asp Phe Leu Glu Lys Phe
                325                 330                 335

Leu Ala Ser Gly
            340

<210> SEQ ID NO 49
<211> LENGTH: 348
<212> TYPE: PRT
<213> ORGANISM: Methylococcus capsulatus

<400> SEQUENCE: 49

Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
                20                  25                  30

Arg Gln Asn Ile Phe Leu Met Ser Ser Cys Arg Glu Gly Gly Cys Ala
            35                  40                  45

Thr Cys Lys Ala Leu Cys Ser Glu Gly Asp Tyr Asp Leu Lys Gly Cys
        50                  55                  60

Ser Val Gln Ala Leu Pro Pro Glu Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Glu Val Gly Ser Phe Glu Ala Glu
            100                 105                 110

Val Val Gly Leu Asn Trp Val Ser Ser Asn Thr Val Gln Phe Leu Leu
        115                 120                 125

Gln Lys Arg Pro Asp Glu Cys Gly Asn Arg Gly Val Lys Phe Glu Pro
    130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190
```

```
Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
        210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
            260                 265                 270

Asn Leu Thr Val Lys Ala Cys Val Trp His Pro Ser Gly Asp Trp Glu
        275                 280                 285

Gly Glu Gln Gly Ser Pro Ile Asp Ala Leu Arg Glu Asp Leu Glu Ser
    290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345
```

<210> SEQ ID NO 50
<211> LENGTH: 340
<212> TYPE: PRT
<213> ORGANISM: Methylosinus trichosporium

<400> SEQUENCE: 50

```
Met Tyr Gln Ile Val Ile Glu Thr Glu Asp Gly Glu Thr Cys Arg Arg
1               5                   10                  15

Met Arg Pro Ser Glu Asp Trp Ile Ser Arg Ala Glu Ala Glu Arg Asn
            20                  25                  30

Leu Leu Ala Ser Cys Arg Ala Gly Cys Ala Thr Cys Lys Ala Asp Cys
        35                  40                  45

Thr Asp Gly Asp Tyr Glu Leu Ile Asp Val Lys Val Gln Ala Val Pro
    50                  55                  60

Pro Asp Glu Glu Glu Asp Gly Lys Val Leu Leu Cys Arg Thr Phe Pro
65                  70                  75                  80

Arg Ser Asp Leu His Leu Leu Val Pro Tyr Thr Tyr Asp Arg Ile Ser
                85                  90                  95

Phe Glu Ala Ile Gln Thr Asn Trp Leu Ala Glu Ile Leu Ala Cys Asp
            100                 105                 110

Arg Val Ser Ser Asn Val Val Arg Leu Val Leu Gln Arg Ser Arg Pro
        115                 120                 125

Met Ala Ala Arg Ile Ser Leu Asn Phe Val Pro Gly Gln Phe Val Asp
    130                 135                 140

Ile Glu Ile Pro Gly Thr His Thr Arg Arg Ser Tyr Ser Met Ala Ser
145                 150                 155                 160

Val Ala Glu Asp Gly Gln Leu Glu Phe Ile Ile Arg Leu Leu Pro Asp
                165                 170                 175

Gly Ala Phe Ser Lys Phe Leu Gln Thr Glu Ala Lys Val Gly Met Arg
            180                 185                 190

Val Asp Leu Arg Gly Pro Ala Gly Ser Phe Phe Leu His Asp His Gly
        195                 200                 205

Gly Arg Ser Arg Val Phe Val Ala Gly Gly Thr Gly Leu Ser Pro Val
    210                 215                 220
```

```
Leu Ser Met Ile Arg Gln Leu Gly Lys Ala Ser Asp Pro Ser Pro Ala
225                 230                 235                 240

Thr Leu Leu Phe Gly Val Thr Asn Arg Glu Glu Leu Phe Tyr Val Asp
                245                 250                 255

Glu Leu Lys Thr Leu Ala Gln Ser Met Pro Thr Leu Gly Val Arg Ile
            260                 265                 270

Ala Val Val Asn Asp Asp Gly Gly Asn Gly Val Asp Lys Gly Thr Val
            275                 280                 285

Ile Asp Leu Leu Arg Ala Glu Leu Glu Ile Asp Leu Leu Leu Gly His
290                 295                 300

Ala Arg Arg Arg Arg Arg Glu Thr Ala Arg Ser Cys Arg Glu Asp
305                 310                 315                 320

His Arg Asp Arg Cys Pro Ala Trp Arg Ser Asp Phe Leu Glu Lys Phe
                325                 330                 335

Leu Ala Ser Gly
            340

<210> SEQ ID NO 51
<211> LENGTH: 348
<212> TYPE: PRT
<213> ORGANISM: Methylococcus capsulatus

<400> SEQUENCE: 51

Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
    50                  55                  60

Ser Val Gln Ala Leu Pro Pro Glu Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Glu Val Gly Ser Phe Glu Ala Glu
            100                 105                 110

Val Val Gly Leu Asn Trp Val Ser Asn Thr Val Gln Phe Leu Leu
        115                 120                 125

Gln Lys Arg Pro Asp Glu Cys Gly Asn Arg Gly Val Lys Phe Glu Pro
    130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190

Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
    210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
```

-continued

```
                245                 250                 255
Glu Leu Phe Tyr Ile Asp Glu Leu Lys Ser Leu Glu Arg Ser Met Arg
            260                 265                 270

Asn Leu Thr Val Lys Ala Cys Val Trp His Pro Ser Gly Asp Trp Glu
        275                 280                 285

Gly Glu Gln Gly Ser Pro Ile Asp Ala Leu Arg Glu Asp Leu Glu Ser
    290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345
```

<210> SEQ ID NO 52
<211> LENGTH: 348
<212> TYPE: PRT
<213> ORGANISM: Methylococcus capsulatus

<400> SEQUENCE: 52

```
Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
    50                  55                  60

Ser Val Gln Ala Leu Pro Pro Glu Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Glu Val Gly Ser Phe Glu Ala Glu
            100                 105                 110

Val Val Gly Leu Asn Trp Val Ser Ser Asn Thr Val Gln Phe Leu Leu
        115                 120                 125

Gln Lys Arg Pro Asp Glu Cys Gly Asn Arg Gly Val Lys Phe Glu Pro
    130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190

Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
    210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
            260                 265                 270
```

Asn Leu Thr Val Lys Ala Cys Val Trp His Pro Ser Gly Asp Trp Glu
            275                 280                 285

Gly Glu Gln Gly Ser Pro Ile Asp Ala Leu Arg Glu Asp Leu Glu Ser
        290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345

<210> SEQ ID NO 53
<211> LENGTH: 343
<212> TYPE: PRT
<213> ORGANISM: Methylosinus trichosporium

<400> SEQUENCE: 53

Met Tyr Gln Ile Val Ile Glu Thr Asp Gly Glu Thr Cys Ser Phe
1               5                   10                  15

Glu Cys Gly Pro Ser Glu Asp Val Ile Ser Ala Gly Leu Arg Gln Ser
            20                  25                  30

Val Ile Leu Leu Ala Ser Cys Arg Ala Gly Gly Cys Ala Thr Cys Lys
        35                  40                  45

Gly Asp Cys Thr Asp Gly Asp Tyr Glu Leu Ile Asp Val Lys Val Gln
50                  55                  60

Ala Leu Pro Pro Asp Glu Glu Asn Gly Lys Val Leu Leu Cys Arg
65                  70                  75                  80

Thr Phe Pro Arg Ser Asp Leu His Ile Leu Val Pro Tyr Thr Phe Asp
                85                  90                  95

Arg Ile Ser Phe Gln Ala Ile Gln Thr Asn Trp Leu Ala Glu Ile Val
            100                 105                 110

Ala Cys Asp Lys Val Ser Ser Asn Val Ala Arg Leu Val Leu Gln Cys
        115                 120                 125

Leu Thr Ala Asp Gly Ser Thr Pro Ile Ala Leu Asp Phe Val Pro Gly
130                 135                 140

Gln Phe Val Asp Ile Glu Ile Pro Gly Thr His Thr Arg Arg Ser Tyr
145                 150                 155                 160

Ser Met Ala Ser Val Ala Glu Asp Gly Arg Leu Glu Phe Phe Ile Arg
                165                 170                 175

Leu Leu Pro Asp Gly Ala Phe Ser Asn Tyr Leu Gln Thr Gly Ala Lys
            180                 185                 190

Val Gly Gln Arg Val Ala Leu Arg Gly Pro Ala Gly Ser Phe Ser Leu
        195                 200                 205

His Lys Ser Glu Arg Ala Arg Phe Phe Val Ala Gly Gly Thr Gly Leu
210                 215                 220

Ser Pro Val Leu Ser Met Ile Arg Gln Leu Lys Lys Glu Ser Ala Ser
225                 230                 235                 240

Gln Pro Ala Thr Leu Phe Phe Gly Val Thr Asn His Glu Glu Leu Phe
                245                 250                 255

Tyr Val Asp Glu Leu Lys Ala Leu Gln Glu Ala Met Pro Ser Leu Asp
            260                 265                 270

Val Arg Val Ala Val Val Asn Ala Ala Glu Gly Asn Gly Val Ala Lys
        275                 280                 285

Gly Thr Val Ile Asp Leu Met Arg Ala Glu Leu Ala Lys Ser Gly Glu
290                 295                 300

```
Lys Pro Asp Ile Tyr Leu Cys Gly Pro Pro Gly Met Ile Glu Ala Ala
305                 310                 315                 320

Phe Ala Ala Ala Ala Thr Ala Gly Val Pro Lys Glu Gln Val Tyr Leu
                325                 330                 335

Glu Lys Phe Leu Ala Ser Gly
            340

<210> SEQ ID NO 54
<211> LENGTH: 111
<212> TYPE: PRT
<213> ORGANISM: Methylosinus sporium

<400> SEQUENCE: 54

Met Ala His Ser Ala Glu Pro Thr Thr Glu Ala Ser Arg Ile Leu Ile
1               5                   10                  15

His Ser Asp Ala Arg Tyr Glu Ala Phe Thr Val Asp Leu Asp Tyr Met
                20                  25                  30

Trp Arg Trp Glu Ile Leu Arg Asp Gly Glu Phe Val Gln Glu Gly Cys
            35                  40                  45

Ser Leu Ser Phe Asp Ser Ser Arg Lys Ala Val Ala His Val Leu Ser
    50                  55                  60

His Phe Lys Arg Gln Asp Glu Ala Ala Gln Arg Pro Gly Asp Asn Ser
65                  70                  75                  80

Ala Glu Ile Lys Arg Leu Leu Gln Ser Leu Gly Thr Pro Ile Pro Val
                85                  90                  95

Asn Glu Gln Asn Asp Ser Thr Lys Asn Glu Leu Ala Gln Pro Glu
            100                 105                 110

<210> SEQ ID NO 55
<211> LENGTH: 103
<212> TYPE: PRT
<213> ORGANISM: Methylococcus capsulatus

<400> SEQUENCE: 55

Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
                20                  25                  30

His Leu Leu Lys Arg Asp Glu Thr Tyr Ala Ala Tyr Ala Lys Asp Leu
            35                  40                  45

Asp Phe Met Trp Arg Trp Val Ile Val Arg Glu Glu Arg Ile Val Gln
    50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100

<210> SEQ ID NO 56
<211> LENGTH: 102
<212> TYPE: PRT
<213> ORGANISM: Methylosinus trichosporium

<400> SEQUENCE: 56

Met Asp Gln Gln Thr Ala His Glu Val Arg Gln Thr Leu Ile His Ala
1               5                   10                  15
```

Asp Glu Arg Tyr Gln Ala Tyr Thr Met Asp Leu Glu Tyr Met Leu Arg
                20                  25                  30

Trp Glu Ile Leu Arg Asp Gly Glu Phe Val Gln Glu Gly Cys Ser Leu
            35                  40                  45

Ser Gln Glu Ser Ala Arg Glu Ala Val Ala His Val Leu Ser His Phe
50                  55                  60

Arg Arg Gln Met Leu Arg Arg Thr Thr Ala Gly Lys Ala Lys Leu
65                  70                  75                  80

Arg Ala Leu Leu Ala Ile Gly Thr Pro Ser Pro Glu Gly Arg Glu Arg
                85                  90                  95

Arg Gly Glu Arg Asp Ile
            100

<210> SEQ ID NO 57
<211> LENGTH: 103
<212> TYPE: PRT
<213> ORGANISM: Methylococcus capsulatus

<400> SEQUENCE: 57

Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
                20                  25                  30

His Leu Leu Lys Arg Asp Glu Thr Tyr Ala Ala Tyr Ala Lys Asp Leu
            35                  40                  45

Asp Phe Met Trp Arg Trp Val Ile Val Arg Glu Glu Arg Ile Val Gln
50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100

<210> SEQ ID NO 58
<211> LENGTH: 103
<212> TYPE: PRT
<213> ORGANISM: Methylococcus capsulatus

<400> SEQUENCE: 58

Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
                20                  25                  30

His Leu Leu Lys Arg Asp Glu Thr Tyr Ala Ala Tyr Ala Lys Asp Leu
            35                  40                  45

Asp Phe Met Trp Arg Trp Val Ile Val Arg Glu Glu Arg Ile Val Gln
50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100

<210> SEQ ID NO 59
<211> LENGTH: 95

```
<212> TYPE: PRT
<213> ORGANISM: Methylocella silvestris

<400> SEQUENCE: 59

Met Asn Val Asp Gln Lys Glu Glu Asn Val Leu Thr Pro Ser Pro Ile
1               5                   10                  15

Asp Arg Gly Ser Phe Thr Gln Ala Thr Arg Val Glu Ile Phe Ser
            20                  25                  30

Glu Gly Arg Tyr Arg Ala Phe Val Gln Asp Leu Glu Cys Met Trp Arg
            35                  40                  45

Trp Glu Ile His Arg Asp Gly Asp Phe Val Gln Glu Gly Cys Ser Leu
        50                  55                  60

Ser Glu Ser Ser Ser Arg Glu Ala Val Gly His Val Val Ser Phe Tyr
65                  70                  75                  80

Gln His Arg Asp Arg Gly Asp Val Ser Arg Ala Asp Ala Gln Tyr
                85                  90                  95

<210> SEQ ID NO 60
<211> LENGTH: 381
<212> TYPE: PRT
<213> ORGANISM: Bacillus methanolicus

<400> SEQUENCE: 60

Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
                100                 105                 110

Gly Arg Ile Asn Asp Tyr Gln Gly Val Asn Ser Val Glu Lys Pro Val
            115                 120                 125

Val Pro Val Val Ala Ile Thr Thr Thr Ala Gly Thr Gly Ser Glu Thr
    130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Ala Lys Gly Ala Thr Pro
        195                 200                 205

Val Thr Asp Ala Phe Ala Ile Gln Ala Met Lys Leu Ile Asn Glu Tyr
    210                 215                 220

Leu Pro Lys Ala Val Ala Asn Gly Glu Asp Ile Glu Ala Arg Glu Ala
225                 230                 235                 240

Met Ala Tyr Ala Gln Tyr Met Ala Gly Val Ala Phe Asn Asn Gly Gly
                245                 250                 255
```

-continued

```
Leu Gly Leu Val His Ser Ile Ser His Gln Val Gly Val Tyr Lys
            260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
    290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Glu Asp Ile Glu Leu Leu Ala
            340                 345                 350

Lys Asn Ala Phe Glu Asp Val Cys Thr Gln Ser Asn Pro Arg Val Ala
        355                 360                 365

Thr Val Gln Asp Ile Ala Gln Ile Ile Lys Asn Ala Leu
    370                 375                 380
```

<210> SEQ ID NO 61
<211> LENGTH: 382
<212> TYPE: PRT
<213> ORGANISM: Bacillus methanolicus

<400> SEQUENCE: 61

```
Met Thr Thr Asn Phe Phe Ile Pro Pro Ala Ser Val Ile Gly Arg Gly
1               5                   10                  15

Ala Val Lys Glu Val Gly Thr Arg Leu Lys Gln Ile Gly Ala Lys Lys
            20                  25                  30

Ala Leu Ile Val Thr Asp Ala Phe Leu His Ser Thr Gly Leu Ser Glu
        35                  40                  45

Glu Val Ala Lys Asn Ile Arg Glu Ala Gly Val Asp Val Ala Ile Phe
    50                  55                  60

Pro Lys Ala Gln Pro Asp Pro Ala Asp Thr Gln Val His Glu Gly Val
65                  70                  75                  80

Asp Val Phe Lys Gln Glu Asn Cys Asp Ser Leu Val Ser Ile Gly Gly
                85                  90                  95

Gly Ser Ser His Asp Thr Ala Lys Ala Ile Gly Leu Val Ala Ala Asn
            100                 105                 110

Gly Gly Arg Ile Asn Asp Tyr Gln Gly Val Asn Ser Val Glu Lys Pro
        115                 120                 125

Val Val Pro Val Ala Ile Thr Thr Thr Ala Gly Thr Gly Ser Glu
    130                 135                 140

Thr Thr Ser Leu Ala Val Ile Thr Asp Ser Ala Arg Lys Val Lys Met
145                 150                 155                 160

Pro Val Ile Asp Glu Lys Ile Thr Pro Thr Val Ala Ile Val Asp Pro
                165                 170                 175

Glu Leu Met Val Lys Lys Pro Ala Gly Leu Thr Ile Ala Thr Gly Met
            180                 185                 190

Asp Ala Leu Ser His Ala Ile Glu Ala Tyr Val Ala Lys Gly Ala Thr
        195                 200                 205

Pro Val Thr Asp Ala Phe Ala Ile Gln Ala Met Lys Leu Ile Asn Glu
    210                 215                 220

Tyr Leu Pro Lys Ala Val Ala Asn Gly Glu Asp Ile Glu Ala Arg Glu
225                 230                 235                 240

Lys Met Ala Tyr Ala Gln Tyr Met Ala Gly Val Ala Phe Asn Asn Gly
                245                 250                 255
```

```
Gly Leu Gly Leu Val His Ser Ile Ser His Gln Val Gly Val Tyr
            260                 265                 270

Lys Leu Gln His Gly Ile Cys Asn Ser Val Asn Met Pro His Val Cys
        275                 280                 285

Ala Phe Asn Leu Ile Ala Lys Thr Glu Arg Phe Ala His Ile Ala Glu
    290                 295                 300

Leu Leu Gly Glu Asn Val Ala Gly Leu Ser Thr Ala Ala Ala Glu
305                 310                 315                 320

Arg Ala Ile Val Ala Leu Glu Arg Ile Asn Lys Ser Phe Gly Ile Pro
                325                 330                 335

Ser Gly Tyr Ala Glu Met Gly Val Lys Glu Asp Ile Glu Leu Leu
            340                 345                 350

Ala Lys Asn Ala Tyr Glu Asp Val Cys Thr Gln Ser Asn Pro Arg Val
        355                 360                 365

Pro Thr Val Gln Asp Ile Ala Gln Ile Lys Asn Ala Met
    370                 375                 380

<210> SEQ ID NO 62
<211> LENGTH: 383
<212> TYPE: PRT
<213> ORGANISM: Bacillus methanolicus

<400> SEQUENCE: 62

Met Thr Gln Arg Asn Phe Phe Ile Pro Pro Ala Ser Val Ile Gly Arg
1               5                   10                  15

Gly Ala Val Lys Glu Val Gly Thr Arg Leu Lys Gln Ile Gly Ala Thr
            20                  25                  30

Lys Ala Leu Ile Val Thr Asp Ala Phe Leu His Gly Thr Gly Leu Ser
        35                  40                  45

Glu Glu Val Ala Lys Asn Ile Arg Glu Ala Gly Leu Asp Ala Val Ile
    50                  55                  60

Phe Pro Lys Ala Gln Pro Asp Pro Ala Asp Thr Gln Val His Glu Gly
65                  70                  75                  80

Val Asp Ile Phe Lys Gln Glu Lys Cys Asp Ala Leu Val Ser Ile Gly
                85                  90                  95

Gly Gly Ser Ser His Asp Thr Ala Lys Ala Ile Gly Leu Val Ala Ala
            100                 105                 110

Asn Gly Gly Arg Ile Asn Asp Tyr Gln Gly Val Asn Ser Val Glu Lys
        115                 120                 125

Pro Val Val Pro Val Val Ala Ile Thr Thr Thr Ala Gly Thr Gly Ser
    130                 135                 140

Glu Thr Thr Ser Leu Ala Val Ile Thr Asp Ser Ala Arg Lys Val Lys
145                 150                 155                 160

Met Pro Val Ile Asp Glu Lys Ile Thr Pro Thr Val Ala Ile Val Asp
                165                 170                 175

Pro Glu Leu Met Val Lys Lys Pro Ala Gly Leu Thr Ile Ala Thr Gly
            180                 185                 190

Met Asp Ala Leu Ser His Ala Ile Glu Ala Tyr Val Ala Lys Arg Ala
        195                 200                 205

Thr Pro Val Thr Asp Ala Phe Ala Ile Gln Ala Met Lys Leu Ile Asn
    210                 215                 220

Glu Tyr Leu Pro Arg Ala Val Ala Asn Gly Glu Asp Ile Glu Ala Arg
225                 230                 235                 240

Glu Ala Met Ala Tyr Ala Gln Tyr Met Ala Gly Val Ala Phe Asn Asn
```

```
            245                 250                 255
Gly Gly Leu Gly Leu Val His Ser Ile Ser His Gln Val Gly Gly Val
            260                 265                 270

Tyr Lys Leu Gln His Gly Ile Cys Asn Ser Val Asn Met Pro His Val
            275                 280                 285

Cys Gln Phe Asn Leu Ile Ala Arg Thr Glu Arg Phe Ala His Ile Ala
            290                 295                 300

Glu Leu Leu Gly Glu Asn Val Ser Gly Leu Ser Thr Ala Ser Ala Ala
305                 310                 315                 320

Glu Arg Ala Ile Val Ala Leu Gln Arg Tyr Asn Lys Asn Phe Gly Ile
            325                 330                 335

Pro Ser Gly Tyr Ala Glu Met Gly Val Lys Glu Asp Ile Glu Leu
            340                 345                 350

Leu Ala Asn Asn Ala Tyr Gln Asp Val Cys Thr Leu Asp Asn Pro Arg
            355                 360                 365

Val Pro Thr Val Gln Asp Ile Ala Gln Ile Ile Lys Asn Ala Leu
            370                 375                 380

<210> SEQ ID NO 63
<211> LENGTH: 381
<212> TYPE: PRT
<213> ORGANISM: Bacillus sp.

<400> SEQUENCE: 63

Met Thr Asn Phe Phe Ile Pro Pro Ala Ser Val Ile Gly Arg Gly Ala
1               5                   10                  15

Val Lys Glu Val Gly Thr Arg Leu Lys Gln Ile Gly Ala Lys Lys Ala
            20                  25                  30

Leu Ile Val Thr Asp Ala Phe Leu His Ser Thr Gly Leu Ser Glu Glu
        35                  40                  45

Val Ala Lys Asn Ile Arg Glu Ala Gly Leu Asp Val Ala Ile Phe Pro
    50                  55                  60

Lys Ala Gln Pro Asp Pro Ala Asp Thr Gln Val His Glu Gly Val Asp
65                  70                  75                  80

Val Phe Lys Gln Glu Asn Cys Asp Ala Leu Val Ser Ile Gly Gly Gly
                85                  90                  95

Ser Ser His Asp Thr Ala Lys Ala Ile Gly Leu Val Ala Ala Asn Gly
            100                 105                 110

Gly Arg Ile Asn Asp Tyr Gln Gly Val Asn Ser Val Glu Lys Pro Val
        115                 120                 125

Val Pro Val Val Ala Ile Thr Thr Ala Gly Thr Gly Ser Glu Thr
    130                 135                 140

Thr Ser Leu Ala Val Ile Thr Asp Ser Ala Arg Lys Val Lys Met Pro
145                 150                 155                 160

Val Ile Asp Glu Lys Ile Thr Pro Thr Val Ala Ile Val Asp Pro Glu
                165                 170                 175

Leu Met Val Lys Lys Pro Ala Gly Leu Thr Ile Ala Thr Gly Met Asp
            180                 185                 190

Ala Leu Ser His Ala Ile Glu Ala Tyr Val Ala Lys Gly Ala Thr Pro
        195                 200                 205

Val Thr Asp Ala Phe Ala Ile Gln Ala Met Lys Leu Ile Asn Glu Tyr
    210                 215                 220

Leu Pro Lys Ala Val Ala Asn Gly Glu Asp Ile Glu Ala Arg Glu Ala
225                 230                 235                 240
```

```
Met Ala Tyr Ala Gln Tyr Met Ala Gly Val Ala Phe Asn Asn Gly Gly
                245                 250                 255

Leu Gly Leu Val His Ser Ile Ser His Gln Val Gly Gly Val Tyr Lys
            260                 265                 270

Leu Gln His Gly Ile Cys Asn Ser Val Asn Met Pro His Val Cys Ala
        275                 280                 285

Phe Asn Leu Ile Ala Lys Thr Glu Arg Phe Ala His Ile Ala Glu Leu
    290                 295                 300

Leu Gly Glu Asn Val Ser Gly Leu Ser Thr Ala Ala Ala Glu Arg
305                 310                 315                 320

Ala Ile Val Ala Leu Glu Arg Tyr Asn Lys Asn Phe Gly Ile Pro Ser
                325                 330                 335

Gly Tyr Ala Glu Met Gly Val Lys Glu Glu Asp Ile Glu Leu Leu Ala
            340                 345                 350

Lys Asn Ala Phe Glu Asp Val Cys Thr Gln Ser Asn Pro Arg Val Ala
        355                 360                 365

Thr Val Gln Asp Ile Ala Gln Ile Ile Lys Asn Ala Leu
    370                 375                 380

<210> SEQ ID NO 64
<211> LENGTH: 185
<212> TYPE: PRT
<213> ORGANISM: Bacillus methanolicus

<400> SEQUENCE: 64

Met Gly Lys Leu Phe Glu Glu Lys Thr Ile Lys Thr Glu Gln Ile Phe
1               5                   10                  15

Ser Gly Arg Val Val Lys Leu Gln Val Asp Asp Val Glu Leu Pro Asn
            20                  25                  30

Gly Gln Thr Ser Lys Arg Glu Ile Val Arg His Pro Gly Ala Val Ala
        35                  40                  45

Val Ile Ala Ile Thr Asn Glu Asn Lys Ile Val Met Val Glu Gln Tyr
    50                  55                  60

Arg Lys Pro Leu Glu Lys Ser Ile Val Glu Ile Pro Ala Gly Lys Leu
65                  70                  75                  80

Glu Lys Gly Glu Asp Pro Arg Val Thr Ala Leu Arg Glu Leu Glu Glu
                85                  90                  95

Glu Thr Gly Tyr Glu Cys Glu Gln Met Glu Trp Leu Ile Ser Phe Ala
            100                 105                 110

Thr Ser Pro Gly Phe Ala Asp Glu Ile Ile His Leu Tyr Val Ala Lys
        115                 120                 125

Gly Leu Ser Lys Lys Glu Asn Ala Ala Gly Leu Asp Glu Asp Glu Phe
    130                 135                 140

Val Asp Leu Ile Glu Leu Thr Leu Asp Glu Ala Leu Gln Tyr Ile Lys
145                 150                 155                 160

Glu Lys Arg Ile Tyr Asp Ser Lys Thr Val Ile Ala Val Gln Tyr Leu
                165                 170                 175

Gln Leu Gln Glu Ala Leu Lys His Lys
            180                 185

<210> SEQ ID NO 65
<211> LENGTH: 375
<212> TYPE: PRT
<213> ORGANISM: Homo sapiens

<400> SEQUENCE: 65
```

```
Met Ser Thr Ala Gly Lys Val Ile Lys Cys Lys Ala Ala Val Leu Trp
1               5                   10                  15
Glu Leu Lys Lys Pro Phe Ser Ile Glu Glu Val Glu Val Ala Pro Pro
            20                  25                  30
Lys Ala His Glu Val Arg Ile Lys Met Val Ala Val Gly Ile Cys Gly
            35                  40                  45
Thr Asp Asp His Val Val Ser Gly Thr Met Val Thr Pro Leu Pro Val
50                  55                  60
Ile Leu Gly His Glu Ala Ala Gly Ile Val Glu Ser Val Gly Glu Gly
65                  70                  75                  80
Val Thr Thr Val Lys Pro Gly Asp Lys Val Ile Pro Leu Ala Ile Pro
                85                  90                  95
Gln Cys Gly Lys Cys Arg Ile Cys Lys Asn Pro Glu Ser Asn Tyr Cys
            100                 105                 110
Leu Lys Asn Asp Val Ser Asn Pro Gln Gly Thr Leu Gln Asp Gly Thr
            115                 120                 125
Ser Arg Phe Thr Cys Arg Arg Lys Pro Ile His Phe Leu Gly Ile
            130                 135                 140
Ser Thr Phe Ser Gln Tyr Thr Val Val Asp Glu Asn Ala Val Ala Lys
145                 150                 155                 160
Ile Asp Ala Ala Ser Pro Leu Glu Lys Val Cys Leu Ile Gly Cys Gly
                165                 170                 175
Phe Ser Thr Gly Tyr Gly Ser Ala Val Asn Val Ala Lys Val Thr Pro
                180                 185                 190
Gly Ser Thr Cys Ala Val Phe Gly Leu Gly Gly Val Gly Leu Ser Ala
            195                 200                 205
Ile Met Gly Cys Lys Ala Ala Gly Ala Ala Arg Ile Ile Ala Val Asp
            210                 215                 220
Ile Asn Lys Asp Lys Phe Ala Lys Ala Lys Glu Leu Gly Ala Thr Glu
225                 230                 235                 240
Cys Ile Asn Pro Gln Asp Tyr Lys Lys Pro Ile Gln Glu Val Leu Lys
                245                 250                 255
Glu Met Thr Asp Gly Gly Val Asp Phe Ser Phe Glu Val Ile Gly Arg
                260                 265                 270
Leu Asp Thr Met Met Ala Ser Leu Leu Cys Cys His Glu Ala Cys Gly
            275                 280                 285
Thr Ser Val Ile Val Gly Val Pro Pro Asp Ser Gln Asn Leu Ser Met
            290                 295                 300
Asn Pro Met Leu Leu Leu Thr Gly Arg Thr Trp Lys Gly Ala Ile Leu
305                 310                 315                 320
Gly Gly Phe Lys Ser Lys Glu Cys Val Pro Lys Leu Val Ala Asp Phe
                325                 330                 335
Met Ala Lys Lys Phe Ser Leu Asp Ala Leu Ile Thr His Val Leu Pro
            340                 345                 350
Phe Glu Lys Ile Asn Glu Gly Phe Asp Leu Leu His Ser Gly Lys Ser
            355                 360                 365
Ile Arg Thr Ile Leu Met Phe
370                 375

<210> SEQ ID NO 66
<211> LENGTH: 375
<212> TYPE: PRT
<213> ORGANISM: Homo sapiens

<400> SEQUENCE: 66
```

```
Met Ser Thr Ala Gly Lys Val Ile Lys Cys Lys Ala Ala Val Leu Trp
1               5                   10                  15

Glu Leu Lys Lys Pro Phe Ser Ile Glu Val Glu Val Ala Pro Pro
            20                  25                  30

Lys Ala His Glu Val Arg Ile Lys Met Val Ala Val Gly Ile Cys Gly
            35                  40                  45

Thr Asp Asp His Val Val Ser Gly Thr Met Val Thr Pro Leu Pro Val
50                  55                  60

Ile Leu Gly His Glu Ala Ala Gly Ile Val Glu Ser Val Gly Glu Gly
65                  70                  75                  80

Val Thr Thr Val Lys Pro Gly Asp Lys Val Ile Pro Leu Ala Ile Pro
                85                  90                  95

Gln Cys Gly Lys Cys Arg Ile Cys Lys Asn Pro Glu Ser Asn Tyr Cys
            100                 105                 110

Leu Lys Asn Asp Val Ser Asn Pro Gln Gly Thr Leu Gln Asp Gly Thr
            115                 120                 125

Ser Arg Phe Thr Cys Arg Arg Lys Pro Ile His His Phe Leu Gly Ile
130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Asn Val Ala Lys Val Thr Pro
                180                 185                 190

Gly Ser Thr Cys Ala Val Phe Gly Leu Gly Gly Val Gly Leu Ser Ala
            195                 200                 205

Ile Met Gly Cys Lys Ala Ala Gly Ala Ala Arg Ile Ile Ala Val Asp
            210                 215                 220

Ile Asn Lys Asp Lys Phe Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
                260                 265                 270

Leu Asp Thr Met Met Ala Ser Leu Leu Cys Cys His Glu Ala Cys Gly
            275                 280                 285

Thr Ser Val Ile Val Gly Val Pro Pro Asp Ser Gln Asn Leu Ser Met
290                 295                 300

Asn Pro Met Leu Leu Leu Thr Gly Arg Thr Trp Lys Gly Ala Ile Leu
305                 310                 315                 320

Gly Gly Phe Lys Ser Lys Glu Cys Val Pro Lys Leu Val Ala Asp Phe
                325                 330                 335

Met Ala Lys Lys Phe Ser Leu Asp Ala Leu Ile Thr His Val Leu Pro
            340                 345                 350

Phe Glu Lys Ile Asn Glu Gly Phe Asp Leu Leu His Ser Gly Lys Ser
            355                 360                 365

Ile Arg Thr Ile Leu Met Phe
370                 375
```

<210> SEQ ID NO 67
<211> LENGTH: 375
<212> TYPE: PRT
<213> ORGANISM: Homo sapiens

```
<400> SEQUENCE: 67

Met Ser Thr Ala Gly Lys Val Ile Lys Cys Lys Ala Ala Val Leu Trp
1               5                   10                  15

Glu Val Lys Lys Pro Phe Ser Ile Glu Asp Val Glu Val Ala Pro Pro
            20                  25                  30

Lys Ala Tyr Glu Val Arg Ile Lys Met Val Ala Val Gly Ile Cys His
        35                  40                  45

Thr Asp Asp His Val Val Ser Gly Asn Leu Val Thr Pro Leu Pro Val
    50                  55                  60

Ile Leu Gly His Glu Ala Ala Gly Ile Val Glu Ser Val Gly Glu Gly
65                  70                  75                  80

Val Thr Thr Val Lys Pro Gly Asp Lys Val Ile Pro Leu Phe Thr Pro
                85                  90                  95

Gln Cys Gly Lys Cys Arg Val Cys Lys Asn Pro Glu Ser Asn Tyr Cys
            100                 105                 110

Leu Lys Asn Asp Leu Gly Asn Pro Arg Gly Thr Leu Gln Asp Gly Thr
        115                 120                 125

Arg Arg Phe Thr Cys Arg Gly Lys Pro Ile His His Phe Leu Gly Thr
    130                 135                 140

Ser Thr Phe Ser Gln Tyr Thr Val Val Asp Glu Asn Ala Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Asn Val Ala Lys Val Thr Pro
            180                 185                 190

Gly Ser Thr Cys Ala Val Phe Gly Leu Gly Gly Val Gly Leu Ser Ala
        195                 200                 205

Val Met Gly Cys Lys Ala Ala Gly Ala Ala Arg Ile Ile Ala Val Asp
    210                 215                 220

Ile Asn Lys Asp Lys Phe Ala Lys Ala Lys Glu Leu Gly Ala Thr Glu
225                 230                 235                 240

Cys Ile Asn Pro Gln Asp Tyr Lys Lys Pro Ile Gln Glu Val Leu Lys
                245                 250                 255

Glu Met Thr Asp Gly Gly Val Asp Phe Ser Phe Glu Val Ile Gly Arg
            260                 265                 270

Leu Asp Thr Met Met Ala Ser Leu Leu Cys Cys His Glu Ala Cys Gly
        275                 280                 285

Thr Ser Val Ile Val Gly Val Pro Pro Ala Ser Gln Asn Leu Ser Ile
    290                 295                 300

Asn Pro Met Leu Leu Leu Thr Gly Arg Thr Trp Lys Gly Ala Val Tyr
305                 310                 315                 320

Gly Gly Phe Lys Ser Lys Glu Gly Ile Pro Lys Leu Val Ala Asp Phe
                325                 330                 335

Met Ala Lys Lys Phe Ser Leu Asp Ala Leu Ile Thr His Val Leu Pro
            340                 345                 350

Phe Glu Lys Ile Asn Glu Gly Phe Asp Leu Leu His Ser Gly Lys Ser
        355                 360                 365

Ile Arg Thr Val Leu Thr Phe
    370                 375

<210> SEQ ID NO 68
<211> LENGTH: 375
<212> TYPE: PRT
<213> ORGANISM: Homo sapiens
```

<400> SEQUENCE: 68

```
Met Ser Thr Ala Gly Lys Val Ile Lys Cys Lys Ala Ala Val Leu Trp
1               5                   10                  15
Glu Leu Lys Lys Pro Phe Ser Ile Glu Glu Val Glu Val Ala Pro Pro
            20                  25                  30
Lys Ala His Glu Val Arg Ile Lys Met Val Ala Ala Gly Ile Cys Arg
        35                  40                  45
Ser Asp Glu His Val Val Ser Gly Asn Leu Val Thr Pro Leu Pro Val
50                  55                  60
Ile Leu Gly His Glu Ala Ala Gly Ile Val Glu Ser Val Gly Glu Gly
65                  70                  75                  80
Val Thr Thr Val Lys Pro Gly Asp Lys Val Ile Pro Leu Phe Thr Pro
                85                  90                  95
Gln Cys Gly Lys Cys Arg Ile Cys Lys Asn Pro Glu Ser Asn Tyr Cys
            100                 105                 110
Leu Lys Asn Asp Leu Gly Asn Pro Arg Gly Thr Leu Gln Asp Gly Thr
        115                 120                 125
Arg Arg Phe Thr Cys Ser Gly Lys Pro Ile His His Phe Val Gly Val
130                 135                 140
Ser Thr Phe Ser Gln Tyr Thr Val Val Asp Glu Asn Ala Val Ala Lys
145                 150                 155                 160
Ile Asp Ala Ala Ser Pro Leu Glu Lys Val Cys Leu Ile Gly Cys Gly
                165                 170                 175
Phe Ser Thr Gly Tyr Gly Ser Ala Val Lys Val Ala Lys Val Thr Pro
            180                 185                 190
Gly Ser Thr Cys Ala Val Phe Gly Leu Gly Gly Val Gly Leu Ser Val
        195                 200                 205
Val Met Gly Cys Lys Ala Ala Gly Ala Ala Arg Ile Ile Ala Val Asp
210                 215                 220
Ile Asn Lys Asp Lys Phe Ala Lys Ala Lys Glu Leu Gly Ala Thr Glu
225                 230                 235                 240
Cys Ile Asn Pro Gln Asp Tyr Lys Lys Pro Ile Gln Glu Val Leu Lys
                245                 250                 255
Glu Met Thr Asp Gly Gly Val Asp Phe Ser Phe Glu Val Ile Gly Arg
            260                 265                 270
Leu Asp Thr Met Met Ala Ser Leu Leu Cys Cys His Glu Ala Cys Gly
        275                 280                 285
Thr Ser Val Ile Val Gly Val Pro Pro Asp Ser Gln Asn Leu Ser Ile
290                 295                 300
Asn Pro Met Leu Leu Leu Thr Gly Arg Thr Trp Lys Gly Ala Ile Phe
305                 310                 315                 320
Gly Gly Phe Lys Ser Lys Glu Ser Val Pro Lys Leu Val Ala Asp Phe
                325                 330                 335
Met Ala Lys Lys Phe Ser Leu Asp Ala Leu Ile Thr Asn Ile Leu Pro
            340                 345                 350
Phe Glu Lys Ile Asn Glu Gly Phe Asp Leu Leu Arg Ser Gly Lys Ser
        355                 360                 365
Ile Arg Thr Val Leu Thr Phe
370                 375
```

<210> SEQ ID NO 69
<211> LENGTH: 215
<212> TYPE: PRT

<213> ORGANISM: Methylococcus capsulatus

<400> SEQUENCE: 69

```
Met Ala Arg Pro Leu Ile Gln Leu Ala Leu Asp Thr Leu Asp Ile Pro
1               5                   10                  15

Gln Thr Leu Lys Leu Ala Ser Leu Thr Ala Pro Tyr Val Asp Ile Phe
            20                  25                  30

Glu Ile Gly Thr Pro Ser Ile Lys His Asn Gly Ile Ala Leu Val Lys
        35                  40                  45

Glu Phe Lys Lys Arg Phe Pro Asn Lys Leu Leu Val Asp Leu Lys
    50                  55                  60

Thr Met Asp Ala Gly Glu Tyr Glu Ala Thr Pro Phe Phe Ala Ala Gly
65                  70                  75                  80

Ala Asp Ile Thr Thr Val Leu Gly Val Ala Gly Leu Ala Thr Ile Lys
                85                  90                  95

Gly Val Ile Asn Ala Ala Asn Lys His Asn Ala Glu Val Gln Val Asp
            100                 105                 110

Leu Ile Asn Val Pro Asp Lys Ala Ala Cys Ala Arg Glu Ser Ala Lys
        115                 120                 125

Ala Gly Ala Gln Ile Val Gly Ile His Thr Gly Leu Asp Ala Gln Ala
    130                 135                 140

Ala Gly Gln Thr Pro Phe Ala Asp Leu Gln Ala Ile Ala Lys Leu Gly
145                 150                 155                 160

Leu Pro Val Arg Ile Ser Val Ala Gly Gly Ile Lys Ala Ser Thr Ala
                165                 170                 175

Gln Gln Val Val Lys Thr Gly Ala Asn Ile Ile Val Val Gly Ala Ala
            180                 185                 190

Ile Tyr Gly Ala Ala Ser Pro Ala Asp Ala Ala Arg Glu Ile Tyr Glu
        195                 200                 205

Gln Val Val Ala Ala Ser Ala
    210                 215
```

<210> SEQ ID NO 70
<211> LENGTH: 226
<212> TYPE: PRT
<213> ORGANISM: Clavibacter michiganensis subsp.

<400> SEQUENCE: 70

```
Met Thr Asp Gly His Pro Ile Pro Thr Thr Thr His His Asp Arg Lys
1               5                   10                  15

Arg Asn His Met Lys Leu Gln Val Ala Met Asp Val Leu Thr Thr Ala
            20                  25                  30

Asp Ala Leu Glu Leu Ala Gly Lys Ala Ala Pro His Val Asp Ile Ile
        35                  40                  45

Glu Leu Gly Thr Pro Leu Ile Lys Ala Glu Gly Leu Ser Ala Ile Thr
    50                  55                  60

Ala Ile Lys Glu Ala His Pro Asp Lys Ile Val Phe Ala Asp Leu Lys
65                  70                  75                  80

Thr Met Asp Ala Gly Glu Leu Glu Ala Asp Ile Ala Phe Ser Ala Gly
                85                  90                  95

Ala Asp Leu Val Thr Val Leu Gly Val Ala Gly Asp Ser Thr Ile Ala
            100                 105                 110

Gly Ala Val Lys Ala Ala Lys Lys His Gly Lys Gly Ile Val Val Asp
        115                 120                 125

Leu Ile Gly Val Pro Asp Lys Ala Lys Arg Ala Lys Glu Val Thr Glu
```

```
                130                 135                 140
Leu Gly Ala Glu Phe Val Glu Met His Ala Gly Leu Asp Glu Gln Ala
145                 150                 155                 160

Glu Asp Gly Tyr Thr Phe Gly Asn Leu Leu Glu Asp Gly Lys Ala Ser
                165                 170                 175

Gly Val Ala Phe Ser Val Ala Gly Gly Val Lys Ala Ser Thr Ile Ala
                180                 185                 190

Asp Val Gln Ala Ala Gly Ala Val Ala Val Ala Gly Gly Ala Ile
                195                 200                 205

Tyr Ser Ala Asp Asp Pro Ala Ala Ala Ala Glu Leu Arg Ala Ala
            210                 215                 220

Ile Arg
225

<210> SEQ ID NO 71
<211> LENGTH: 215
<212> TYPE: PRT
<213> ORGANISM: Methylococcus capsulatus str.

<400> SEQUENCE: 71

Met Ala Arg Pro Leu Ile Gln Leu Ala Leu Asp Thr Leu Asp Ile Pro
1               5                   10                  15

Gln Thr Leu Lys Leu Ala Ser Leu Thr Ala Pro Tyr Val Asp Ile Phe
                20                  25                  30

Glu Ile Gly Thr Pro Ser Ile Lys His Asn Gly Ile Ala Leu Val Lys
            35                  40                  45

Glu Phe Lys Lys Arg Phe Pro Asn Lys Leu Leu Val Asp Leu Lys
50                  55                  60

Thr Met Asp Ala Gly Glu Tyr Glu Ala Thr Pro Phe Phe Ala Ala Gly
65                  70                  75                  80

Ala Asp Ile Thr Thr Val Leu Gly Val Ala Gly Leu Ala Thr Ile Lys
                85                  90                  95

Gly Val Ile Asn Ala Ala Asn Lys His Asn Ala Glu Val Gln Val Asp
            100                 105                 110

Leu Ile Asn Val Pro Asp Lys Ala Ala Cys Ala Arg Glu Ser Ala Lys
        115                 120                 125

Ala Gly Ala Gln Ile Val Gly Ile His Thr Gly Leu Asp Ala Gln Ala
    130                 135                 140

Ala Gly Gln Thr Pro Phe Ala Asp Leu Gln Ala Ile Ala Lys Leu Gly
145                 150                 155                 160

Leu Pro Val Arg Ile Ser Val Ala Gly Gly Ile Lys Ala Ser Thr Ala
                165                 170                 175

Gln Gln Val Lys Thr Gly Ala Asn Ile Ile Val Val Gly Ala Ala
                180                 185                 190

Ile Tyr Gly Ala Ala Ser Pro Ala Asp Ala Ala Arg Glu Ile Tyr Glu
        195                 200                 205

Gln Val Val Ala Ala Ser Ala
    210                 215

<210> SEQ ID NO 72
<211> LENGTH: 226
<212> TYPE: PRT
<213> ORGANISM: Clavibacter michiganensis subsp.

<400> SEQUENCE: 72

Met Thr Asp Gly His Pro Ile Pro Thr Thr Thr His His Asp Arg Lys
```

-continued

```
              1               5                   10                  15
            Arg Asn His Met Lys Leu Gln Val Ala Met Asp Val Leu Thr Thr Ala
                            20                  25                  30
            Asp Ala Leu Glu Leu Ala Gly Lys Ala Ala Pro His Val Asp Ile Ile
                            35                  40                  45
            Glu Leu Gly Thr Pro Leu Ile Lys Ala Glu Gly Leu Ser Ala Ile Thr
                            50                  55                  60
            Ala Ile Lys Glu Ala His Pro Asp Lys Ile Val Phe Ala Asp Leu Lys
             65                 70                  75                  80
            Thr Met Asp Ala Gly Glu Leu Glu Ala Asp Ile Ala Phe Ser Ala Gly
                            85                  90                  95
            Ala Asp Leu Val Thr Val Leu Gly Val Ala Gly Asp Ser Thr Ile Ala
                            100                 105                 110
            Gly Ala Val Lys Ala Ala Lys Lys His Gly Lys Gly Ile Val Val Asp
                            115                 120                 125
            Leu Ile Gly Val Pro Asp Lys Ala Lys Arg Ala Lys Glu Val Thr Glu
                        130                 135                 140
            Leu Gly Ala Glu Phe Val Glu Met His Ala Gly Leu Asp Glu Gln Ala
            145                 150                 155                 160
            Glu Asp Gly Tyr Thr Phe Gly Asn Leu Leu Glu Asp Gly Lys Ala Ser
                            165                 170                 175
            Gly Val Ala Phe Ser Val Ala Gly Gly Val Lys Ala Ser Thr Ile Ala
                            180                 185                 190
            Asp Val Gln Ala Ala Gly Ala Val Val Ala Val Ala Gly Gly Ala Ile
                            195                 200                 205
            Tyr Ser Ala Asp Asp Pro Ala Ala Ala Ala Glu Leu Arg Ala Ala
                            210                 215                 220
            Ile Arg
            225

<210> SEQ ID NO 73
<211> LENGTH: 210
<212> TYPE: PRT
<213> ORGANISM: Staphylococcus aureus subsp.

<400> SEQUENCE: 73

Met Glu Leu Gln Leu Ala Ile Asp Leu Leu Asn Lys Glu Asp Ala Ala
             1               5                   10                  15
            Glu Leu Ala Asn Lys Val Lys Asp Tyr Val Asp Ile Val Glu Ile Gly
                            20                  25                  30
            Thr Pro Ile Ile Tyr Asn Glu Gly Leu Pro Ala Val Lys His Met Ala
                            35                  40                  45
            Asp Asn Ile Ser Asn Val Lys Val Leu Ala Asp Met Lys Ile Met Asp
             50                 55                  60
            Ala Ala Asp Tyr Glu Val Ser Gln Ala Ile Lys Phe Gly Ala Asp Val
             65                 70                  75                  80
            Ile Thr Ile Leu Gly Val Ala Glu Asp Ala Ser Ile Lys Ala Ala Ile
                            85                  90                  95
            Glu Glu Ala His Lys Asn Asn Lys Gln Leu Leu Val Asp Met Ile Ala
                            100                 105                 110
            Val Gln Asp Leu Glu Lys Arg Ala Lys Glu Leu Asp Glu Met Gly Ala
                            115                 120                 125
            Asp Tyr Ile Ala Val His Thr Gly Tyr Asp Leu Gln Ala Glu Gly Gln
                            130                 135                 140
```

```
Ser Pro Leu Glu Ser Leu Arg Thr Val Lys Ser Val Ile Lys Asn Ser
145                 150                 155                 160

Lys Val Ala Val Ala Gly Gly Ile Lys Pro Asp Thr Ile Lys Glu Ile
                165                 170                 175

Val Ala Glu Ser Pro Asp Leu Val Ile Val Gly Gly Ile Ala Asn
                180                 185                 190

Ala Asp Asp Pro Val Glu Ala Ala Lys Gln Cys Arg Ala Ala Ile Glu
                195                 200                 205

Gly Lys
    210

<210> SEQ ID NO 74
<211> LENGTH: 210
<212> TYPE: PRT
<213> ORGANISM: Staphylococcus aureus subsp.

<400> SEQUENCE: 74

Met Glu Leu Gln Leu Ala Ile Asp Leu Leu Asn Lys Glu Asp Ala Ala
1               5                   10                  15

Glu Leu Ala Asn Lys Val Lys Asp Tyr Val Asp Ile Val Glu Ile Gly
                20                  25                  30

Thr Pro Ile Ile Tyr Asn Glu Gly Leu Pro Ala Val Lys His Met Ala
            35                  40                  45

Asp Asn Ile Ser Asn Val Lys Val Leu Ala Asp Met Lys Ile Met Asp
    50                  55                  60

Ala Ala Asp Tyr Glu Val Ser Gln Ala Ile Lys Phe Gly Ala Asp Val
65                  70                  75                  80

Ile Thr Ile Leu Gly Val Ala Glu Asp Ala Ser Ile Lys Ala Ala Ile
                85                  90                  95

Glu Glu Ala His Lys Asn Asn Lys Gln Leu Leu Val Asp Met Ile Ala
                100                 105                 110

Val Gln Asp Leu Glu Lys Arg Ala Lys Glu Leu Asp Glu Met Gly Ala
                115                 120                 125

Asp Tyr Ile Ala Val His Thr Gly Tyr Asp Leu Gln Ala Glu Gly Gln
    130                 135                 140

Ser Pro Leu Glu Ser Leu Arg Thr Val Lys Ser Val Ile Lys Asn Ser
145                 150                 155                 160

Lys Val Ala Val Ala Gly Gly Ile Lys Pro Asp Thr Ile Lys Asp Ile
                165                 170                 175

Val Ala Glu Ser Pro Asp Leu Val Ile Val Gly Gly Ile Ala Asn
                180                 185                 190

Ala Asp Asp Pro Val Glu Ala Ala Lys Gln Cys Arg Ala Ala Ile Glu
                195                 200                 205

Gly Lys
    210

<210> SEQ ID NO 75
<211> LENGTH: 216
<212> TYPE: PRT
<213> ORGANISM: Salmonella enterica subsp.

<400> SEQUENCE: 75

Met Ser Leu Pro Met Leu Gln Val Ala Leu Asp Asn Gln Thr Met Asp
1               5                   10                  15

Ser Ala Tyr Glu Thr Thr Arg Leu Ile Ala Glu Glu Val Asp Ile Ile
                20                  25                  30
```

```
Glu Val Gly Thr Ile Leu Cys Val Gly Gly Val Arg Ala Val Arg
         35                  40                  45

Asp Leu Lys Ala Leu Tyr Pro His Lys Ile Val Leu Ala Asp Ala Lys
 50                  55                  60

Ile Ala Asp Ala Gly Lys Ile Leu Ser Arg Met Cys Phe Glu Ala Asn
 65                  70                  75                  80

Ala Asp Trp Val Thr Val Ile Cys Cys Ala Asp Ile Asn Thr Ala Lys
                 85                  90                  95

Gly Ala Leu Asp Val Ala Lys Glu Phe Asn Gly Asp Val Gln Ile Glu
                100                 105                 110

Leu Thr Gly Tyr Trp Thr Trp Glu Gln Ala Gln Gln Trp Arg Asp Ala
            115                 120                 125

Gly Ile Gln Gln Val Val Tyr His Arg Ser Arg Asp Ala Gln Ala Ala
130                 135                 140

Gly Val Ala Trp Gly Glu Ala Asp Ile Thr Ala Ile Lys Arg Leu Ser
145                 150                 155                 160

Asp Met Gly Phe Lys Val Thr Val Thr Gly Gly Leu Ala Leu Glu Asp
                165                 170                 175

Leu Pro Leu Phe Lys Gly Ile Pro Ile His Val Phe Ile Ala Gly Arg
            180                 185                 190

Ser Ile Arg Asp Ala Glu Ser Pro Val Glu Ala Arg Gln Phe Lys
        195                 200                 205

Arg Ser Ile Ala Gln Leu Trp Gly
        210                 215

<210> SEQ ID NO 76
<211> LENGTH: 220
<212> TYPE: PRT
<213> ORGANISM: Salmonella enterica subsp.

<400> SEQUENCE: 76

Met Ser Arg Pro Leu Leu Gln Leu Ala Leu Asp His Thr Ser Leu Glu
 1               5                  10                  15

Ala Ala Gln Arg Asp Val Ala Leu Leu Gln Asp His Val Asp Ile Val
                 20                  25                  30

Glu Ala Gly Thr Ile Leu Cys Leu Thr Glu Gly Leu Ser Ala Val Lys
             35                  40                  45

Ala Leu Arg Ala Gln Cys Pro Glu Lys Ile Ile Val Ala Asp Trp Lys
 50                  55                  60

Val Ala Asp Ala Gly Glu Thr Leu Ala Gln Gln Ala Phe Ser Ala Gly
 65                  70                  75                  80

Ala Asn Trp Met Thr Ile Ile Cys Ala Ala Pro Leu Ala Thr Val Glu
                 85                  90                  95

Lys Gly His Ala Val Ala Gln Ser Cys Gly Gly Glu Ile Gln Met Glu
                100                 105                 110

Leu Phe Gly Asn Trp Thr Leu Asp Asp Ala Arg Asp Trp Tyr Arg Val
            115                 120                 125

Gly Val Arg Gln Ala Ile Tyr His Arg Gly Arg Asp Ala Gln Ala Ser
130                 135                 140

Gly Gln Gln Trp Gly Glu Ala Asp Leu Thr Arg Met Lys Ala Leu Ser
145                 150                 155                 160

Asp Ile Gly Leu Glu Leu Ser Ile Thr Gly Gly Ile Thr Pro Ala Asp
                165                 170                 175

Leu Pro Leu Phe Arg Asp Ile Asn Val Lys Ala Phe Ile Ala Gly Arg
            180                 185                 190
```

Ala Leu Ala Gly Ala Ala His Pro Ala Gln Val Ala Ala Glu Phe His
        195                 200                 205

Ala Gln Ile Asp Ala Ile Trp Gly Glu Lys His Ala
        210                 215                 220

<210> SEQ ID NO 77
<211> LENGTH: 211
<212> TYPE: PRT
<213> ORGANISM: Bacillus sp.

<400> SEQUENCE: 77

Met Met Lys Val Gln Leu Ala Leu Asp Arg Leu Thr Asn Glu Glu Cys
1               5                   10                  15

Phe Arg Ile Val Lys Glu Ala Tyr Glu Asn Ile Asp Trp Ile Glu Ile
                20                  25                  30

Gly Thr Gly Val Ile Lys Glu Tyr Gly Met Asp Ile Ile Arg Ser Met
            35                  40                  45

Lys Lys Glu Phe Pro Glu Lys Val Leu Val Ala Asp Met Lys Thr Cys
        50                  55                  60

Asp Ala Gly Arg His Glu Ala Asn Gln Ala Phe Gly Ala Gly Ala Asp
65                  70                  75                  80

Ile Val Thr Val Met Gly Phe Ser His Asn Gly Thr Ile Lys Glu Thr
                85                  90                  95

Leu Glu Ala Ala Glu Ala Tyr Gly Lys Arg Ile Met Ile Asp Leu Leu
            100                 105                 110

Gly Ile His Asp Ser Ala Arg Ala Arg Glu Ile His Gln Leu Gly Ala
        115                 120                 125

Arg Leu Phe Cys Leu His Ile Gly Lys Asp Met Gln Lys Glu Gly Gln
130                 135                 140

Leu Ala Asp Pro Ala Leu Phe Gln Ala Asp Gly Leu Glu Asp Ser
145                 150                 155                 160

Glu Ile Ala Ile Ala Gly Gly Ile Ser Glu Lys Thr Ile Gly Thr Leu
                165                 170                 175

Lys Asn Ser Ile Val Asp Ile Ala Ile Val Gly Ser Ala Ile Thr Gly
            180                 185                 190

Ser Glu Lys Pro Gly Ala Ser Ser Leu Ser Leu Lys Arg Leu Ile Gly
        195                 200                 205

Ala Asp Leu
        210

<210> SEQ ID NO 78
<211> LENGTH: 211
<212> TYPE: PRT
<213> ORGANISM: Bacillus methanolicus

<400> SEQUENCE: 78

Met Glu Leu Gln Leu Ala Leu Asp Leu Val Asn Ile Glu Glu Ala Lys
1               5                   10                  15

Gln Val Val Ala Glu Val Gln Glu Tyr Val Asp Ile Val Glu Ile Gly
                20                  25                  30

Thr Pro Val Ile Lys Ile Trp Gly Leu Gln Ala Val Lys Ala Val Lys
            35                  40                  45

Asp Ala Phe Pro His Leu Gln Val Leu Ala Asp Met Lys Thr Met Asp
        50                  55                  60

Ala Ala Ala Tyr Glu Val Ala Lys Ala Ala Glu His Gly Ala Asp Ile
65                  70                  75                  80

-continued

```
Val Thr Ile Leu Ala Ala Glu Asp Val Ser Ile Lys Gly Ala Val
                85                  90                  95

Glu Glu Ala Lys Lys Leu Gly Lys Lys Ile Leu Val Asp Met Ile Ala
            100                 105                 110

Val Lys Asn Leu Glu Glu Arg Ala Lys Gln Val Asp Glu Met Gly Val
        115                 120                 125

Asp Tyr Ile Cys Val His Ala Gly Tyr Asp Leu Gln Ala Val Gly Lys
    130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
        195                 200                 205

Gln Gly Leu
    210

<210> SEQ ID NO 79
<211> LENGTH: 177
<212> TYPE: PRT
<213> ORGANISM: Methylomonas methanica

<400> SEQUENCE: 79

Met His Gln Glu Leu Val Ile Ser Lys Ile Ser Ser Ile Leu Glu Ala
1               5                   10                  15

Thr Pro Asp Gly His Asp Lys Ala Leu Val Asp Met Leu Asp Gln Ala
            20                  25                  30

Lys Arg Ile Phe Ile Ser Gly Ala Gly Arg Ser Lys Leu Val Gly Asn
        35                  40                  45

Phe Phe Ala Met Arg Leu Met His Gly Gly Tyr Asp Val Ser Val Val
    50                  55                  60

Gly Glu Ile Val Thr Pro Ser Ile Lys Ala Gly Asp Leu Leu Ile Ile
65                  70                  75                  80

Ile Ser Gly Ser Gly Glu Thr Glu Gln Leu Ile Ala Phe Thr Lys Lys
                85                  90                  95

Ala Lys Glu Ile Gly Ala Lys Ile Val Leu Ile Ser Ala Lys Asp Asp
            100                 105                 110

Ser Thr Ile Gly Asp Met Ala Asp Val Thr Leu Gln Ile Gly Arg Ala
        115                 120                 125

Glu Gln Tyr Gly Lys Val Lys Gly Met Pro Met Gly Thr Val Phe Glu
    130                 135                 140

Leu Ser Thr Leu Leu Phe Leu Glu Ala Thr Ile Ser His Val Ile His
145                 150                 155                 160

Asp Lys Gly Ile Glu Glu Ile Met Arg Ser Arg His Ala Asn Leu
                165                 170                 175

Glu

<210> SEQ ID NO 80
<211> LENGTH: 177
<212> TYPE: PRT
<213> ORGANISM: Methylococcus capsulatus str.

<400> SEQUENCE: 80
```

```
Met His Gln Lys Leu Ile Ile Asp Lys Ile Ser Gly Ile Leu Ala Ala
1               5                   10                  15

Thr Asp Ala Gly Tyr Asp Ala Lys Leu Thr Ala Met Leu Asp Gln Ala
            20                  25                  30

Ser Arg Ile Phe Val Ala Gly Ala Gly Arg Ser Gly Leu Val Ala Lys
        35                  40                  45

Phe Phe Ala Met Arg Leu Met His Gly Gly Tyr Asp Val Phe Val Val
    50                  55                  60

Gly Glu Ile Val Thr Pro Ser Ile Arg Lys Gly Asp Leu Leu Ile Val
65                  70                  75                  80

Ile Ser Gly Ser Gly Glu Thr Glu Thr Met Leu Ala Phe Thr Lys Lys
                85                  90                  95

Ala Lys Glu Gln Gly Ala Ser Ile Ala Leu Ile Ser Thr Arg Asp Ser
            100                 105                 110

Ser Ser Leu Gly Asp Leu Ala Asp Ser Val Phe Arg Ile Gly Ser Pro
        115                 120                 125

Glu Leu Phe Gly Lys Val Val Gly Met Pro Met Gly Thr Val Phe Glu
    130                 135                 140

Leu Ser Thr Leu Leu Phe Leu Glu Ala Thr Ile Ser His Ile Ile His
145                 150                 155                 160

Glu Lys Gly Ile Pro Glu Glu Met Arg Thr Arg His Ala Asn Leu
                165                 170                 175

Glu

<210> SEQ ID NO 81
<211> LENGTH: 201
<212> TYPE: PRT
<213> ORGANISM: Desulfurococcus fermentans

<400> SEQUENCE: 81

Met Val Ser Gly Val Thr Arg Asp Ala Met Leu Gly Ile Ile Asp Phe
1               5                   10                  15

Ala Leu Lys Ala Val Asp Leu Ile Ser Asp Asp Glu Lys Glu Lys Met
            20                  25                  30

Ile Asp Thr Leu Ile Asp Ala Leu Arg Asn Asn Lys Lys Val Phe Val
        35                  40                  45

Ile Gly Ala Gly Arg Ser Gly Leu Val Gly Lys Ala Phe Ala Met Arg
    50                  55                  60

Leu Leu His Leu Gly Phe Asn Thr Tyr Ile Val Gly Glu Thr Ile Leu
65                  70                  75                  80

Pro Arg Ala Ser Pro Gly Asp Val Leu Val Ser Ile Ser Gly Ser Gly
                85                  90                  95

Arg Thr Arg Leu Val Val Ala Ala Glu Val Ala Lys Ser Val Gly
            100                 105                 110

Val Lys Val Ile Ala Ile Thr Thr Tyr Pro Asp Ser Pro Leu Gly Lys
        115                 120                 125

Leu Ala Asp Ile Val Val Arg Ile Pro Gly Arg Thr Lys Met Ala Ala
    130                 135                 140

Glu Glu Asp Tyr Ile Ser Arg Gln Ile Leu Gly Leu His Glu Pro Leu
145                 150                 155                 160

Ala Pro Leu Gly Thr Leu Phe Glu Asp Thr Leu Leu Ile Phe Leu Asp
                165                 170                 175

Gly Val Ile Ala Glu Leu Met Asp Lys Leu Gly Val Thr Glu Glu Glu
            180                 185                 190
```

Leu Arg Asn Arg His Ala Asn Ile Glu
        195                 200

<210> SEQ ID NO 82
<211> LENGTH: 196
<212> TYPE: PRT
<213> ORGANISM: Archaeoglobus veneficus

<400> SEQUENCE: 82

Met Ala Glu Ala Arg Gly Arg Leu Met Gly Glu Met Leu Ile Arg Phe
1               5                   10                  15

Leu Asp Thr Leu Gly Glu Gln Ile Asn Ser Leu Lys Arg Glu Leu Asp
            20                  25                  30

Pro Ser Gln Val Glu Glu Leu Ile Lys Ala Ile Glu Gly Ala Asn Lys
        35                  40                  45

Ile Phe Val Met Gly Ala Gly Arg Ser Gly Phe Val Ala Lys Ala Phe
50                  55                  60

Ala Met Arg Leu Met His Leu Gly Tyr Asn Val Tyr Val Val Gly Glu
65                  70                  75                  80

Thr Val Thr Pro Arg Ile Gly Arg Asp Asp Val Leu Ile Ser Ile Ser
            85                  90                  95

Gly Ser Gly Glu Thr Thr Ser Val Val Asn Ile Ser Arg Lys Ala Lys
        100                 105                 110

Glu Leu Ile Gly Ser Lys Leu Val Ala Ile Thr Gln Asn Lys Asp Ser
    115                 120                 125

Thr Leu Ala Arg Met Ser Asp Val Val Leu Leu Arg Ala Lys Asp
130                 135                 140

Lys Thr Gln Lys Asp Glu Asn Leu Ser Ser Ile Ala Pro Leu Gly Thr
145                 150                 155                 160

Met Phe Glu Leu Thr Ala Leu Ile Phe Leu Asp Gly Leu Val Ala Glu
            165                 170                 175

Leu Met Ser Leu Lys Ser Leu Thr Glu Arg Asp Leu Glu Gln Arg His
        180                 185                 190

Ala Val Leu Glu
    195

<210> SEQ ID NO 83
<211> LENGTH: 200
<212> TYPE: PRT
<213> ORGANISM: Methanoplanus limicola

<400> SEQUENCE: 83

Met Thr Glu Cys Glu Asn Val Gln Asp Met Ile Arg Leu Met Ala Ser
1               5                   10                  15

Lys Leu Glu Glu Met Ala Asp Ser Leu Ser Asp Lys Gly Val Lys Gln
            20                  25                  30

Phe Ile Asp Glu Ile Leu Gly Ala Arg Ser Ile Tyr Val Met Gly Ala
        35                  40                  45

Gly Arg Ser Gly Leu Val Ala Lys Ser Phe Ala Met Arg Leu Met His
50                  55                  60

Leu Gly Leu Lys Ser Tyr Val Ile Gly Glu Thr Ile Thr Pro Ala Met
65                  70                  75                  80

Lys Asp Gly Asp Thr Val Val Ala Phe Ser Gly Ser Gly Glu Thr Lys
            85                  90                  95

Thr Ile Ala Glu Leu Cys Glu Thr Ala Lys Ala Leu Asn Gly Arg Ile
        100                 105                 110

```
Cys Leu Val Thr Ser Lys Lys Asp Ser Arg Ile Gly Lys Ile Ala Asn
            115                 120                 125

Ser Thr Val Val Ile Glu Ser His Arg Asp Gln Val Asp Asp Glu Ser
130                 135                 140

Ala Glu Tyr Glu Ile Arg Gln Met Met Gly Asp His Lys Ser Phe Ala
145                 150                 155                 160

Pro Leu Gly Thr Leu Phe Glu Thr Gly Ser Met Val Phe Ala Asp Ser
                165                 170                 175

Ile Ile Ser Ala Val Met Glu Ile Glu Cys Glu Ser Asp Leu
            180                 185                 190

Lys Cys Arg His Ala Asn Ile Glu
        195                 200

<210> SEQ ID NO 84
<211> LENGTH: 180
<212> TYPE: PRT
<213> ORGANISM: Lactobacillus brevis

<400> SEQUENCE: 84

Met Thr Leu Ile Asp Gln Val Thr Gln Glu Val Asn Glu Val Met Gly
1               5                   10                  15

Met Ile Asp Glu Ser Gln Leu Asp Gln Ala Glu Lys Leu Ile Gln Lys
            20                  25                  30

Asp Arg Arg Ile Phe Val Leu Gly Ala Gly Arg Ser Gly Leu Met Ala
        35                  40                  45

Lys Gly Phe Ala Met Arg Leu Met His Ile Gly Tyr Thr Val Phe Val
50                  55                  60

Ile Gly Glu Thr Ile Thr Pro Ser Ile Gln Ala Gly Asp Val Leu Leu
65                  70                  75                  80

Ala Val Ser Gly Ser Gly Lys Thr Ala Ser Ile Leu Glu Leu Ala Glu
                85                  90                  95

Lys Ala Ala Ala Ser Gly Val Thr Val Ile Ala Val Thr Ser His Ala
            100                 105                 110

Asp Ser Pro Leu Gly Lys Val Gly Gln Ala Val Ile Val Pro Gly
        115                 120                 125

Ala Thr Lys Thr Gly Asp Gly Val Lys Ser Ile Gln Leu Leu Ser Thr
130                 135                 140

Leu Phe Asp Gln Ser Val His Leu Thr Leu Asp Val Leu Cys Leu Lys
145                 150                 155                 160

Leu Ser Arg Arg Asp Lys Val Ser Asn Asp Ala Ala Ala Thr His
                165                 170                 175

Ser Asn Met Glu
            180

<210> SEQ ID NO 85
<211> LENGTH: 193
<212> TYPE: PRT
<213> ORGANISM: Methanobacterium sp.

<400> SEQUENCE: 85

Met Glu Tyr Ile Lys Lys Thr Ala Glu Gly Ile Ala Lys His Ala Leu
1               5                   10                  15

Glu Val Ile Gly Arg Ile Asp Glu Glu Gln Val Glu Leu Met Ile Gln
            20                  25                  30

Cys Ile Thr Asp Ser Asn Ser Thr Phe Ile Val Gly Ser Gly Arg Ser
        35                  40                  45
```

-continued

```
Glu Leu Val Gly Lys Ser Phe Ala Met Arg Leu Met His Leu Gly Phe
 50                  55                  60
Lys Val Tyr Val Val Gly Asp Val Thr Thr Pro Ala Leu Thr Glu Lys
 65                  70                  75                  80
Asp Cys Leu Ile Ala Ile Ser Gly Ser Gly Glu Thr Lys Thr Val Thr
                 85                  90                  95
Leu Ala Ala Glu Thr Ala Arg Glu Val Gly Thr Lys Val Val Gly Val
                100                 105                 110
Thr Thr Asp Leu Glu Ser Thr Leu Ser Lys Asn Ser Asp Val Val Val
                115                 120                 125
Asn Ile Asp Ser Lys Ser Lys Val Pro Trp Lys Tyr Tyr Thr Ser His
130                 135                 140
Val Leu Lys Gly Asn Tyr Asp Asp Leu Thr Pro Met Gly Thr Leu Phe
145                 150                 155                 160
Glu Asp Ser Thr His Leu Phe Leu Asp Gly Leu Ile Ala Glu Phe Met
                165                 170                 175
Val Arg Leu Gly Lys Lys Glu Asn Asp Leu Gln Lys Leu His Ala Arg
                180                 185                 190
Asp

<210> SEQ ID NO 86
<211> LENGTH: 434
<212> TYPE: PRT
<213> ORGANISM: Pyrococcus furiosus

<400> SEQUENCE: 86

Met Ala Ser Pro Val Asp Gly Tyr Tyr Gln Ile Leu Trp Ser Ser Lys
 1               5                  10                  15
Phe Phe Ser Leu Phe Ser Tyr Leu Ser Pro Ser Asp Asn Thr Thr Asn
                 20                  25                  30
Ile Lys Thr Leu Lys Glu His Pro Leu Lys Gln Lys Arg Val Cys Val
                 35                  40                  45
Met Ile Leu Gln Val Ala Leu Asp Leu Thr Asp Ile Glu Gln Ala Ile
 50                  55                  60
Ser Ile Ala Glu Lys Ala Arg Gly Gly Ala His Trp Leu Glu Val
 65                  70                  75                  80
Gly Thr Pro Leu Ile Lys Lys Glu Gly Met Arg Ala Val Glu Leu Met
                 85                  90                  95
Lys Arg Arg Phe Pro Asp Arg Lys Ile Val Ala Asp Leu Lys Thr Met
                100                 105                 110
Asp Thr Gly Ala Leu Glu Val Glu Met Ala Ala Arg His Gly Ala Asp
                115                 120                 125
Val Val Ser Ile Leu Gly Val Ala Asp Asp Lys Thr Ile Lys Asp Ala
130                 135                 140
Leu Ala Val Ala Arg Lys Tyr Gly Ile Lys Val Met Val Asp Leu Ile
145                 150                 155                 160
Gly Val Lys Asp Lys Val Lys Arg Ala Lys Glu Leu Glu Glu Met Gly
                165                 170                 175
Val His Tyr Ile Leu Val His Thr Gly Ile Asp Glu Gln Ala Gln Gly
                180                 185                 190
Lys Ser Pro Leu Glu Asp Leu Glu Lys Val Val Lys Ala Val Lys Ile
                195                 200                 205
Pro Val Ala Val Ala Gly Gly Leu Asn Leu Glu Thr Ile Pro Lys Val
210                 215                 220
```

```
Ile Glu Leu Gly Ala Thr Ile Ile Val Val Gly Ser Ala Ile Thr Lys
225                 230                 235                 240

Ala Lys Asp Pro Glu Glu Val Thr Arg Lys Ile Ile Asp Leu Phe Trp
            245                 250                 255

Asp Glu Tyr Met Arg Thr Ile Lys Lys Ala Met Lys Asp Ile Thr Glu
            260                 265                 270

His Ile Asn Glu Val Ala Asp Lys Leu Lys Leu Glu Glu Val Arg Gly
        275                 280                 285

Leu Val Asp Ala Met Ile Gly Ala Asn Lys Ile Phe Ile Tyr Gly Ala
    290                 295                 300

Gly Arg Ser Gly Leu Val Gly Lys Ala Phe Ala Met Arg Leu Met His
305                 310                 315                 320

Leu Asp Phe Asn Val Tyr Val Gly Glu Thr Ile Thr Pro Ala Phe
            325                 330                 335

Glu Glu Gly Asp Leu Leu Ile Ala Ile Ser Gly Ser Gly Glu Thr Lys
            340                 345                 350

Thr Ile Val Asp Ala Ala Glu Ile Ala Lys Gln Gln Gly Gly Lys Val
            355                 360                 365

Val Ala Ile Thr Ser Tyr Arg Asp Ser Thr Leu Gly Lys Leu Ala Asp
370                 375                 380

Val Val Glu Ile Pro Gly Arg Thr Lys Thr Asp Val Pro Thr Asp
385                 390                 395                 400

Tyr Ile Ala Arg Gln Met Leu Thr Gln Tyr Lys Trp Thr Ala Pro Met
                405                 410                 415

Gly Thr Leu Phe Glu Asp Ser Thr Met Val Phe Leu Asp Gly Val Ile
            420                 425                 430

Ala Cys

<210> SEQ ID NO 87
<211> LENGTH: 409
<212> TYPE: PRT
<213> ORGANISM: Methanosarcina mazei

<400> SEQUENCE: 87

Met Glu Ile Ala Lys Glu Ala Val Ala Gly Gly Ala Asp Trp Ile Glu
1               5                   10                  15

Ile Gly Thr Pro Leu Ile Lys Ser Glu Gly Met Asn Ala Ile Arg Thr
            20                  25                  30

Met Arg Lys Ala Phe Pro Asp Arg Thr Ile Leu Ala Asp Met Lys Thr
        35                  40                  45

Val Asp Thr Gly Ala Met Glu Val Met Ala Ala Lys Ala Gly Ala
    50                  55                  60

Asp Val Ala Ile Val Leu Gly Ser Ala Asp Ser Thr Ile Leu Asp
65                  70                  75                  80

Ala Leu Arg Ser Ala His Lys Tyr Gly Val Arg Leu Met Ala Asp Leu
                85                  90                  95

Ile Ser Ala Pro Asp Pro Val Lys Arg Ala Val Glu Leu Glu Ala Leu
            100                 105                 110

Gly Val Asp Tyr Ile Asn Val His Val Gly Ile Asp Gln Gln Met Ile
        115                 120                 125

Gly Lys Asp Pro Val Ser Ile Leu Met Glu Ile Ser Glu Lys Val Gly
    130                 135                 140

Val Gln Leu Ala Val Ala Gly Gly Leu Asp Ser Glu Ser Ala Ala Gln
145                 150                 155                 160
```

```
Ala Val Arg Ala Gly Ala Arg Ile Val Val Gly Gly Asn Ile Thr
            165                 170                 175

Arg Ser Asp Asn Val Thr Glu Ala Ala Lys Lys Ile Arg Lys Ser Val
        180                 185                 190

Asp Ser Pro Glu Ser Val Asp Ile Arg Asp Arg Gly Thr Val Asp Gln
        195                 200                 205

Glu Ile Arg Glu Ile Phe Lys Glu Val Ser Thr Ser Asn Ile Ser Asp
        210                 215                 220

Ala Met His Arg Lys Gly Ala Met Lys Gly Ile His Pro Leu Val Arg
225                 230                 235                 240

Gly Lys Met Val Gly Pro Ala Val Thr Val Gln Cys Phe Pro Gly Asp
                245                 250                 255

Trp Ala Lys Thr Val Glu Ala Ile Asp Leu Ala Lys Pro Gly Asp Val
                260                 265                 270

Ile Val Ile Tyr Asn Glu Ser Lys Asp Ile Ala Cys Trp Gly Gly Leu
            275                 280                 285

Ala Thr Leu Ser Ser Leu Asn Lys Gly Ile Ala Gly Val Val Ile Glu
            290                 295                 300

Gly Ala Val Arg Asp Ile Asp Glu Val Glu Asn Leu Gly Leu Pro Ile
305                 310                 315                 320

Tyr Thr Ser Asn Thr Val Pro Asn Ala Gly Asp Pro Lys Gly Phe Gly
                325                 330                 335

Glu Ile Asn Ala Glu Ile Thr Cys Gly Ser Gln Ala Val Lys Pro Gly
                340                 345                 350

Asp Tyr Ile Ile Gly Asp Glu Ser Gly Val Val Val Pro Lys Glu
            355                 360                 365

Arg Ala Tyr Glu Leu Ala Arg Arg Ala Lys Glu Val Asn Lys Glu Glu
            370                 375                 380

Lys Arg Leu Phe Asp Glu Ile Arg Arg Gly Gly Thr Leu Ser Glu Ile
385                 390                 395                 400

Leu Lys Leu Lys Lys Trp Glu Lys Ile
                405

<210> SEQ ID NO 88
<211> LENGTH: 427
<212> TYPE: PRT
<213> ORGANISM: Methanocorpusculum labreanum

<400> SEQUENCE: 88

Met Gln Ser Pro Ile Leu Gln Val Ala Leu Asp Val Thr Glu Leu Thr
1               5                   10                  15

Arg Ala Gln Lys Ile Ala Glu Glu Ala Leu Ala Gly Gly Ala Asp Trp
                20                  25                  30

Ile Glu Ile Gly Thr Pro Leu Val Lys Ser Glu Gly Met Gln Ala Val
            35                  40                  45

Arg Ala Leu Arg Ala Gln Phe Pro Thr Thr Thr Leu Val Ala Asp Leu
        50                  55                  60

Lys Thr Ala Asp Thr Gly Gly Met Glu Val Glu Met Ala Ala Lys Ala
65                  70                  75                  80

Gly Ala Asn Ile Val Cys Val Leu Ala Asn Thr Asp Asn Ala Val Ile
                85                  90                  95

Ile Asp Ala Leu Arg Gly Ala Ser Leu Tyr Gly Val Gln Ile Met Ala
            100                 105                 110

Asp Met Met Asn Val Glu Asp Val Val Thr Arg Ala Lys Glu Leu Ala
        115                 120                 125
```

```
Asp Leu Gly Val Gln Ile Ile Asn Ala His Val Gly Ile Asp Gln Gln
            130                 135                 140

Met Glu Gly Lys Asp Pro Leu Asp Ile Leu Asp Lys Leu Gly Asp Leu
145                 150                 155                 160

Pro Leu Glu Ile Ala Val Ala Gly Gly Leu Asn Ala Glu Thr Ala Ser
                165                 170                 175

Lys Ala Ala Ala Arg Gly Ala Asp Ile Val Ile Val Gly Gly Ser Ile
            180                 185                 190

Ile Lys Ala Ala Asp Val Thr Lys Ala Ala Arg Asn Val Arg Asp Ala
            195                 200                 205

Ile Asp His Pro Ala Glu Gly Thr Thr Val Lys Thr Ser Leu Asp Asp
            210                 215                 220

Thr Ile Arg Glu Leu Leu Glu Gln Val Ser Ala Pro Asn Val Thr Asp
225                 230                 235                 240

Ala Leu Tyr Arg Lys Gly Ala Met Ser Gly Leu Thr Val Gln Tyr Val
                245                 250                 255

Pro Lys Lys Met Ile Gly Lys Ala Val Thr Val Gln Thr Phe Gly Gly
                260                 265                 270

Asp Trp Ser Lys Pro Val Gln Ala Ile Asp Glu Cys Ile Pro Gly Asp
            275                 280                 285

Val Leu Val Ile Ser Asn Asp Lys Arg Thr Asp Ile Ala Pro Trp Gly
290                 295                 300

Glu Leu Ala Thr Arg Ser Ala Glu Asn Lys Gly Val Ala Gly Ile Ile
305                 310                 315                 320

Ile Asp Gly Ala Val Arg Asp Trp Asp Ile Val Thr Leu Glu Thr
                325                 330                 335

Pro Val Tyr Ala Thr Gly Ile Gln Pro Asn Ala Gly Glu Pro Lys Gly
                340                 345                 350

Phe Gly Glu Ile Asn Ala Asp Ile Ser Cys Cys Gly Gln Thr Val Arg
            355                 360                 365

Pro Gly Asp Trp Leu Ile Gly Asp Gln Ser Gly Val Val Val Ile Pro
370                 375                 380

Arg Glu Arg Ala Tyr Glu Val Ala Arg Ala Val Glu Val Gln Lys
385                 390                 395                 400

Thr Glu Val Arg Ile Arg Glu Glu Ile Arg Arg Gly Gly Thr Leu Gly
                405                 410                 415

Ser Leu Ser Gln Leu Leu Arg Trp Glu Lys Lys
            420                 425

<210> SEQ ID NO 89
<211> LENGTH: 420
<212> TYPE: PRT
<213> ORGANISM: Methanocorpusculum labreanum

<400> SEQUENCE: 89

Met Lys Ser Leu Tyr Pro Pro Gly Ala Asn Thr Thr Ala Glu Ile Ile
1               5                   10                  15

Pro Met Phe Leu Ile Gly Glu Ala Leu Val Gly Asp Gly Ala Glu Leu
            20                  25                  30

Ala His Ile Asp Leu Met Ile Gly Asp Lys Asn Gly Pro Val Gly Met
        35                  40                  45

Ser Phe Ala Asn Gly Leu Thr Gln Leu Ser Ala Gly His Thr Pro Leu
    50                  55                  60

Leu Gly Val Ile Arg Pro Asn Leu Leu Pro Lys Pro Ala Val Leu Ile
```

```
                65                  70                  75                  80
Val Pro Lys Val Thr Leu Lys His Thr Glu Gln Val Thr Gln Ile Phe
                    85                  90                  95

Gly Pro Ala Gln Ala Ala Val Ser Lys Ala Ile Ala Asp Ala Leu Glu
                100                 105                 110

Asp Gly Val Phe Ala Gly Met Asp Val Glu Glu Asn Val Ile Val Ala
                115                 120                 125

Ser Val Phe Ile Asp Pro Ser Ala Lys Asp Phe Asn Lys Leu Tyr Arg
130                 135                 140

Phe Asn Tyr Gly Ala Thr Arg Leu Ala Leu Ser Arg Ala Leu Asp Lys
145                 150                 155                 160

Phe Pro Asp Thr Thr Thr Val Leu Lys Glu Lys Asp Arg Ala Ala His
                165                 170                 175

Gly Val Met Gly Phe Lys Val Gln Arg Leu Trp Asn Pro Pro Tyr Leu
                180                 185                 190

Gln Val Ala Met Asp Leu Val Asp Met Lys Gln Val Glu Arg Val Leu
                195                 200                 205

Thr Gly Val Pro Gln Asn Asp His Val Ile Phe Glu Ala Gly Thr Pro
                210                 215                 220

Leu Ile Lys Gln Phe Gly Leu Ser Val Ile Asn Glu Ile Arg Lys Ile
225                 230                 235                 240

Arg Pro Asn Cys Phe Ile Val Ala Asp Leu Lys Thr Leu Asp Thr Gly
                245                 250                 255

Asn Leu Glu Ala Arg Met Val Ser Asn Ala Gly Gly Asp Ala Ala Val
                260                 265                 270

Val Ser Gly Leu Ala Pro Val Glu Thr Ile Ala Ala Phe Ile Lys Glu
                275                 280                 285

Ala Lys Lys Cys Gly Ile Tyr Ala Ile Ile Asp Met Leu Asn Val Glu
                290                 295                 300

Glu Pro Ala Lys Leu Ile Glu Ser Leu Gly Gln Met Gly Gly Ala Ala
305                 310                 315                 320

Leu Leu Pro Gln Tyr Val Glu Met His Arg Ala Ile Asp Lys Glu Ser
                325                 330                 335

Thr Gly Asp Tyr Ser Trp Gly Asp Ile Lys Lys Ile Lys Glu Val Ala
                340                 345                 350

Lys Thr Tyr Asp Ala Lys Ile Leu Val Ala Thr Ala Gly Gly Ile Arg
                355                 360                 365

Gln Pro Val Val Lys Lys Ala Ile Ala Ala Gly Ala Asp Ile Val Val
                370                 375                 380

Val Gly Arg Ala Ile Thr Ala Ser Lys Asp Ile Lys Asn Ala Ala Glu
385                 390                 395                 400

Ser Phe Leu Glu Glu Leu Asp Ser Glu Glu Ile Asp Gln Phe Arg Ile
                405                 410                 415

Met Thr Asp Phe
                420

<210> SEQ ID NO 90
<211> LENGTH: 391
<212> TYPE: PRT
<213> ORGANISM: Methylomicrobium alcaliphilum

<400> SEQUENCE: 90

Met Ala Lys Pro Leu Ile Gln Leu Ala Leu Asp Ser Leu Asp Phe Asp
1               5                   10                  15
```

Lys Thr Leu Glu Leu Ala Ser Gln Ala Ala Pro Tyr Val Asp Ile Ile
            20                  25                  30

Glu Ile Gly Thr Pro Cys Ile Lys Phe Asn Gly Leu Glu Leu Val Lys
        35                  40                  45

Glu Ile Lys Arg Arg Phe Pro Asp Lys Leu Leu Leu Val Asp Leu Lys
    50                  55                  60

Thr Met Asp Ala Gly Glu Tyr Glu Ala Ser Pro Phe Tyr Glu Ala Gly
65                  70                  75                  80

Ala Asp Ile Cys Thr Val Leu Gly Thr Ser Gly Ile Ser Thr Ile Lys
                85                  90                  95

Gly Val Ile Asn Ala Ala Lys Lys Tyr Asn Ala Glu Val Gln Val Asp
            100                 105                 110

Leu Ile Asn Val Glu Asp Lys Ala Ser Cys Ala Glu Glu Ala Val Ala
        115                 120                 125

Ala Gly Ala Gln Ile Ile Gly Ile His Thr Gly Ile Asp Ala Gln Ala
130                 135                 140

Ala Gly Gln Thr Pro Phe Ala Asp Leu Gln Asp Leu Leu Arg Leu Gly
145                 150                 155                 160

Leu Asn Thr Arg Val Ser Val Ala Gly Gly Ile Lys Pro Glu Thr Val
                165                 170                 175

Arg Asp Val Val Glu Ala Gly Val Asp Ile Ile Val Val Gly Gly Ala
            180                 185                 190

Ile Thr Gly Ala Pro Ser Pro Val Asn Ala Ala Arg Lys Ile Gln Arg
        195                 200                 205

Leu Val Asn Ser Lys Gly Thr His Arg Glu Phe Val Val Asp Lys Ile
    210                 215                 220

Ser Asp Val Leu Tyr Ala Thr Asp Asp Ser Tyr Asp Arg Lys Leu Thr
225                 230                 235                 240

Asn Met Leu Asp Gln Ala Arg Arg Ile Phe Val Ser Gly Ala Gly Arg
                245                 250                 255

Ser Gly Leu Ile Gly Arg Phe Phe Ala Met Arg Leu Met His Ser Gly
            260                 265                 270

Tyr Asp Thr Ser Val Val Gly Glu Ile Val Thr Pro Ser Ile Lys Gln
        275                 280                 285

Gly Asp Leu Leu Ile Ile Ile Ser Gly Ser Gly Glu Thr Glu Gln Leu
    290                 295                 300

Val Ala Phe Thr Lys Arg Ala Arg Glu Ile Gly Ala Lys Ile Val Leu
305                 310                 315                 320

Ile Ser Ala Lys Ser Glu Ser Thr Ile Gly Asp Met Ala Asp Ala Val
                325                 330                 335

Phe Arg Val Gly Ser Pro Glu Gln Tyr Gly Lys Val Val Gly Met Pro
            340                 345                 350

Met Gly Thr Val Phe Glu Leu Ser Thr Leu Ala Phe Leu Glu Ala Thr
        355                 360                 365

Ile Ser His Val Ile His Glu Lys Gly Ile Pro Glu Glu Glu Met Arg
    370                 375                 380

Ser Arg His Ala Asn Leu Glu
385                 390

<210> SEQ ID NO 91
<211> LENGTH: 391
<212> TYPE: PRT
<213> ORGANISM: Methylomicrobium alcaliphilum

<400> SEQUENCE: 91

-continued

```
Met Ala Lys Pro Leu Ile Gln Leu Ala Leu Asp Ser Leu Asp Phe Asp
1               5                   10                  15

Lys Thr Leu Glu Leu Ala Ser Gln Ala Ala Pro Tyr Val Asp Ile Ile
                20                  25                  30

Glu Ile Gly Thr Pro Cys Ile Lys Phe Asn Gly Leu Glu Leu Val Lys
            35                  40                  45

Glu Ile Lys Arg Arg Phe Pro Asp Lys Leu Leu Leu Val Asp Leu Lys
50                      55                  60

Thr Met Asp Ala Gly Glu Tyr Glu Ala Ser Pro Phe Tyr Glu Ala Gly
65                  70                  75                  80

Ala Asp Ile Cys Thr Val Leu Gly Thr Ser Gly Ile Ser Thr Ile Lys
                85                  90                  95

Gly Val Ile Asn Ala Ala Lys Lys Tyr Asn Ala Glu Val Gln Val Asp
                100                 105                 110

Leu Ile Asn Val Glu Asp Lys Ala Ser Cys Ala Glu Glu Ala Val Ala
            115                 120                 125

Ala Gly Ala Gln Ile Ile Gly Ile His Thr Gly Ile Asp Ala Gln Ala
130                 135                 140

Ala Gly Gln Thr Pro Phe Ala Asp Leu Gln Asp Leu Leu Arg Leu Gly
145                 150                 155                 160

Leu Asn Thr Arg Val Ser Val Ala Gly Gly Ile Lys Pro Glu Thr Val
                165                 170                 175

Arg Asp Val Val Glu Ala Gly Val Asp Ile Ile Val Val Gly Gly Ala
                180                 185                 190

Ile Thr Gly Ala Pro Ser Pro Val Asn Ala Ala Arg Lys Ile Gln Arg
            195                 200                 205

Leu Val Asn Ser Lys Gly Thr His Arg Glu Phe Val Val Asp Lys Ile
210                 215                 220

Ser Asp Val Leu Tyr Ala Thr Asp Asp Ser Tyr Asp Arg Lys Leu Thr
225                 230                 235                 240

Asn Met Leu Asp Gln Ala Arg Arg Ile Phe Val Ser Gly Ala Gly Arg
                245                 250                 255

Ser Gly Leu Ile Gly Arg Phe Phe Ala Met Arg Leu Met His Ser Gly
                260                 265                 270

Tyr Asp Thr Ser Val Val Gly Glu Ile Val Thr Pro Ser Ile Lys Gln
            275                 280                 285

Gly Asp Leu Leu Ile Ile Ile Ser Gly Ser Gly Glu Thr Glu Gln Leu
            290                 295                 300

Val Ala Phe Thr Lys Arg Ala Arg Glu Ile Gly Ala Lys Ile Val Leu
305                 310                 315                 320

Ile Ser Ala Lys Ser Glu Ser Thr Ile Gly Asp Met Ala Asp Ala Val
                325                 330                 335

Phe Arg Val Gly Ser Pro Glu Gln Tyr Gly Lys Val Val Gly Met Pro
                340                 345                 350

Met Gly Thr Val Phe Glu Leu Ser Thr Leu Ala Phe Leu Glu Ala Thr
            355                 360                 365

Ile Ser His Val Ile His Glu Lys Gly Ile Pro Glu Glu Glu Met Arg
            370                 375                 380

Ser Arg His Ala Asn Leu Glu
385                 390
```

<210> SEQ ID NO 92
<211> LENGTH: 382

<212> TYPE: PRT
<213> ORGANISM: Bacillus methanolicus

<400> SEQUENCE: 92

| | | | | | | | | | | | | | | |
|---|---|---|---|---|---|---|---|---|---|---|---|---|---|---|
| Met | Thr | Thr | Asn | Phe | Phe | Ile | Pro | Pro | Ala | Ser | Val | Ile | Gly | Arg | Gly |
| 1 | | | | 5 | | | | | 10 | | | | | 15 | |
| Ala | Val | Lys | Glu | Val | Gly | Thr | Arg | Leu | Lys | Gln | Ile | Gly | Ala | Lys | Lys |
| | | | 20 | | | | | 25 | | | | | 30 | | |
| Ala | Leu | Ile | Val | Thr | Asp | Ala | Phe | Leu | His | Ser | Thr | Gly | Leu | Ser | Glu |
| | | | 35 | | | | 40 | | | | | 45 | | | |
| Glu | Val | Ala | Lys | Asn | Ile | Arg | Glu | Ala | Gly | Val | Asp | Val | Ala | Ile | Phe |
| | 50 | | | | | 55 | | | | | 60 | | | | |
| Pro | Lys | Ala | Gln | Pro | Asp | Pro | Ala | Asp | Thr | Gln | Val | His | Glu | Gly | Val |
| 65 | | | | | 70 | | | | | 75 | | | | | 80 |
| Asp | Val | Phe | Lys | Gln | Glu | Asn | Cys | Asp | Ser | Leu | Val | Ser | Ile | Gly | Gly |
| | | | | 85 | | | | | 90 | | | | | 95 | |
| Gly | Ser | Ser | His | Asp | Thr | Ala | Lys | Ala | Ile | Gly | Leu | Val | Ala | Ala | Asn |
| | | | 100 | | | | | 105 | | | | | 110 | | |
| Gly | Gly | Arg | Ile | Asn | Asp | Tyr | Gln | Gly | Val | Asn | Ser | Val | Glu | Lys | Pro |
| | | 115 | | | | | 120 | | | | | 125 | | | |
| Val | Val | Pro | Val | Val | Ala | Ile | Thr | Thr | Thr | Ala | Gly | Thr | Gly | Ser | Glu |
| | 130 | | | | | 135 | | | | | 140 | | | | |
| Thr | Thr | Ser | Leu | Ala | Val | Ile | Thr | Asp | Ser | Ala | Arg | Lys | Val | Lys | Met |
| 145 | | | | | 150 | | | | | 155 | | | | | 160 |
| Pro | Val | Ile | Asp | Glu | Lys | Ile | Thr | Pro | Thr | Val | Ala | Ile | Val | Asp | Pro |
| | | | | 165 | | | | | 170 | | | | | 175 | |
| Glu | Leu | Met | Val | Lys | Lys | Pro | Ala | Gly | Leu | Thr | Ile | Ala | Thr | Gly | Met |
| | | | 180 | | | | | 185 | | | | | 190 | | |
| Asp | Ala | Leu | Ser | His | Ala | Ile | Glu | Ala | Tyr | Val | Ala | Lys | Gly | Ala | Thr |
| | | | 195 | | | | | 200 | | | | | 205 | | |
| Pro | Val | Thr | Asp | Ala | Phe | Ala | Ile | Gln | Ala | Met | Lys | Leu | Ile | Asn | Glu |
| | 210 | | | | | 215 | | | | | 220 | | | | |
| Tyr | Leu | Pro | Lys | Ala | Val | Ala | Asn | Gly | Glu | Asp | Ile | Glu | Ala | Arg | Glu |
| 225 | | | | | 230 | | | | | 235 | | | | | 240 |
| Lys | Met | Ala | Tyr | Ala | Gln | Tyr | Met | Ala | Gly | Val | Ala | Phe | Asn | Asn | Gly |
| | | | | 245 | | | | | 250 | | | | | 255 | |
| Gly | Leu | Gly | Leu | Val | His | Ser | Ile | Ser | His | Gln | Val | Gly | Gly | Val | Tyr |
| | | | 260 | | | | | 265 | | | | | 270 | | |
| Lys | Leu | Gln | His | Gly | Ile | Cys | Asn | Ser | Val | Asn | Met | Pro | His | Val | Cys |
| | | 275 | | | | | 280 | | | | | 285 | | | |
| Ala | Phe | Asn | Leu | Ile | Ala | Lys | Thr | Glu | Arg | Phe | Ala | His | Ile | Ala | Glu |
| | 290 | | | | | 295 | | | | | 300 | | | | |
| Leu | Leu | Gly | Glu | Asn | Val | Ala | Gly | Leu | Ser | Thr | Ala | Ala | Ala | Ala | Glu |
| 305 | | | | | 310 | | | | | 315 | | | | | 320 |
| Arg | Ala | Ile | Val | Ala | Leu | Glu | Arg | Ile | Asn | Lys | Ser | Phe | Gly | Ile | Pro |
| | | | | 325 | | | | | 330 | | | | | 335 | |
| Ser | Gly | Tyr | Ala | Glu | Met | Gly | Val | Lys | Glu | Glu | Asp | Ile | Glu | Leu | Leu |
| | | | 340 | | | | | 345 | | | | | 350 | | |
| Ala | Lys | Asn | Ala | Tyr | Glu | Asp | Val | Cys | Thr | Gln | Ser | Asn | Pro | Arg | Val |
| | | 355 | | | | | 360 | | | | | 365 | | | |
| Pro | Thr | Val | Gln | Asp | Ile | Ala | Gln | Ile | Ile | Lys | Asn | Ala | Met | | |
| | 370 | | | | | 375 | | | | | 380 | | | | |

<210> SEQ ID NO 93

```
<211> LENGTH: 211
<212> TYPE: PRT
<213> ORGANISM: Bacillus methanolicus

<400> SEQUENCE: 93

Met Glu Leu Gln Leu Ala Leu Asp Leu Val Asn Ile Glu Glu Ala Lys
1               5                   10                  15

Gln Val Val Ala Glu Val Gln Glu Tyr Val Asp Ile Val Glu Ile Gly
            20                  25                  30

Thr Pro Val Ile Lys Ile Trp Gly Leu Gln Ala Val Lys Ala Val Lys
        35                  40                  45

Asp Ala Phe Pro His Leu Gln Val Leu Ala Asp Met Lys Thr Met Asp
    50                  55                  60

Ala Ala Ala Tyr Glu Val Ala Lys Ala Ala Glu His Gly Ala Asp Ile
65                  70                  75                  80

Val Thr Ile Leu Ala Ala Ala Glu Asp Val Ser Ile Lys Gly Ala Val
                85                  90                  95

Glu Glu Ala Lys Lys Leu Gly Lys Lys Ile Leu Val Asp Met Ile Ala
            100                 105                 110

Val Lys Asn Leu Glu Glu Arg Ala Lys Gln Val Asp Glu Met Gly Val
        115                 120                 125

Asp Tyr Ile Cys Val His Ala Gly Tyr Asp Leu Gln Ala Val Gly Lys
    130                 135                 140

Asn Pro Leu Asp Asp Leu Lys Arg Ile Lys Ala Val Val Lys Asn Ala
145                 150                 155                 160

Lys Thr Ala Ile Ala Gly Gly Ile Lys Leu Glu Thr Leu Pro Glu Val
                165                 170                 175

Ile Lys Ala Glu Pro Asp Leu Val Ile Val Gly Gly Gly Ile Ala Asn
            180                 185                 190

Gln Thr Asp Lys Lys Ala Ala Ala Glu Lys Ile Asn Lys Leu Val Lys
    195                 200                 205

Gln Gly Leu
    210

<210> SEQ ID NO 94
<211> LENGTH: 406
<212> TYPE: PRT
<213> ORGANISM: Pyrococcus horikoshii

<400> SEQUENCE: 94

Met Ile Leu Gln Val Ala Leu Asp Leu Thr Asp Ile Glu Gln Ala Ile
1               5                   10                  15

Ser Ile Ala Glu Lys Ala Ala Arg Gly Gly Ala His Trp Leu Glu Val
            20                  25                  30

Gly Thr Pro Leu Ile Lys Lys Gly Met Arg Ala Val Glu Leu Leu
        35                  40                  45

Lys Arg Arg Phe Pro Asp Arg Lys Ile Val Ala Asp Leu Lys Thr Met
    50                  55                  60

Asp Thr Gly Ala Leu Glu Val Glu Met Ala Arg His Gly Ala Asp
65                  70                  75                  80

Val Val Ser Ile Leu Gly Val Ala Asp Lys Thr Ile Lys Asp Ala
                85                  90                  95

Leu Ala Val Ala Arg Lys Tyr Gly Val Lys Ile Met Val Asp Leu Ile
            100                 105                 110

Gly Val Lys Asp Lys Val Gln Arg Ala Lys Glu Leu Glu Gln Met Gly
    115                 120                 125
```

```
Val His Tyr Ile Leu Val His Thr Gly Ile Asp Glu Gln Ala Gln Gly
    130                 135                 140

Lys Thr Pro Leu Glu Asp Leu Glu Lys Val Val Lys Ala Val Lys Ile
145                 150                 155                 160

Pro Val Ala Val Ala Gly Gly Leu Asn Leu Glu Thr Ile Pro Lys Val
                165                 170                 175

Ile Glu Leu Gly Ala Thr Ile Val Val Gly Ser Ala Ile Thr Lys
            180                 185                 190

Ser Lys Asp Pro Glu Gly Val Thr Arg Lys Ile Ile Asp Leu Phe Trp
            195                 200                 205

Asp Glu Tyr Met Lys Thr Ile Arg Lys Ala Met Lys Asp Ile Thr Asp
    210                 215                 220

His Ile Asn Glu Val Ala Asp Lys Leu Arg Leu Asp Glu Val Arg Gly
225                 230                 235                 240

Leu Val Asp Ala Met Ile Gly Ala Asn Lys Ile Phe Ile Tyr Gly Ala
                245                 250                 255

Gly Arg Ser Gly Leu Val Gly Lys Ala Phe Ala Met Arg Leu Met His
            260                 265                 270

Leu Asp Phe Asn Val Tyr Val Val Gly Glu Thr Ile Thr Pro Ala Phe
    275                 280                 285

Glu Glu Gly Asp Leu Leu Ile Ala Ile Ser Gly Ser Gly Glu Thr Lys
    290                 295                 300

Thr Ile Val Asp Ala Ala Glu Ile Ala Lys Gln Gln Gly Lys Val
305                 310                 315                 320

Val Ala Ile Thr Ser Tyr Lys Asp Ser Thr Leu Gly Arg Leu Ala Asp
                325                 330                 335

Val Val Val Glu Ile Pro Gly Arg Thr Lys Thr Asp Val Pro Thr Asp
                340                 345                 350

Tyr Ile Ala Arg Gln Met Leu Thr Lys Tyr Lys Trp Thr Ala Pro Met
    355                 360                 365

Gly Thr Leu Phe Glu Asp Ser Thr Met Ile Phe Leu Asp Gly Ile Ile
    370                 375                 380

Ala Leu Leu Met Ala Thr Phe Gln Lys Thr Glu Lys Asp Met Arg Lys
385                 390                 395                 400

Lys His Ala Thr Leu Glu
            405

<210> SEQ ID NO 95
<211> LENGTH: 187
<212> TYPE: PRT
<213> ORGANISM: Bacillus methanolicus

<400> SEQUENCE: 95

Met Ile Ser Met Leu Thr Thr Glu Phe Leu Ala Glu Ile Val Lys Glu
1               5                   10                  15

Leu Asn Ser Ser Val Asn Gln Ile Ala Asp Glu Glu Ala Glu Ala Leu
            20                  25                  30

Val Asn Gly Ile Leu Gln Ser Lys Lys Val Phe Val Ala Gly Ala Gly
        35                  40                  45

Arg Ser Gly Phe Met Ala Lys Ser Phe Ala Met Arg Met Met His Met
    50                  55                  60

Gly Ile Asp Ala Tyr Val Val Gly Glu Thr Val Thr Pro Asn Tyr Glu
65                  70                  75                  80

Lys Glu Asp Ile Leu Ile Ile Gly Ser Gly Ser Gly Glu Thr Lys Ser
            85                  90                  95
```

-continued

```
Leu Val Ser Met Ala Gln Lys Ala Lys Ser Ile Gly Gly Thr Ile Ala
            100                 105                 110

Ala Val Thr Ile Asn Pro Glu Ser Thr Ile Gly Gln Leu Ala Asp Ile
            115                 120                 125

Val Ile Lys Met Pro Gly Ser Pro Lys Asp Lys Ser Glu Ala Arg Glu
        130                 135                 140

Thr Ile Gln Pro Met Gly Ser Leu Phe Glu Gln Thr Leu Leu Leu Phe
145                 150                 155                 160

Tyr Asp Ala Val Ile Leu Arg Phe Met Glu Lys Lys Gly Leu Asp Thr
                165                 170                 175

Lys Thr Met Tyr Gly Arg His Ala Asn Leu Glu
            180                 185
```